US010188136B2

(12) United States Patent
Britto et al.

(10) Patent No.: US 10,188,136 B2
(45) Date of Patent: Jan. 29, 2019

(54) HYDROPHOBIN MIMICS: PROCESS FOR PREPARATION THEREOF

(71) Applicant: **

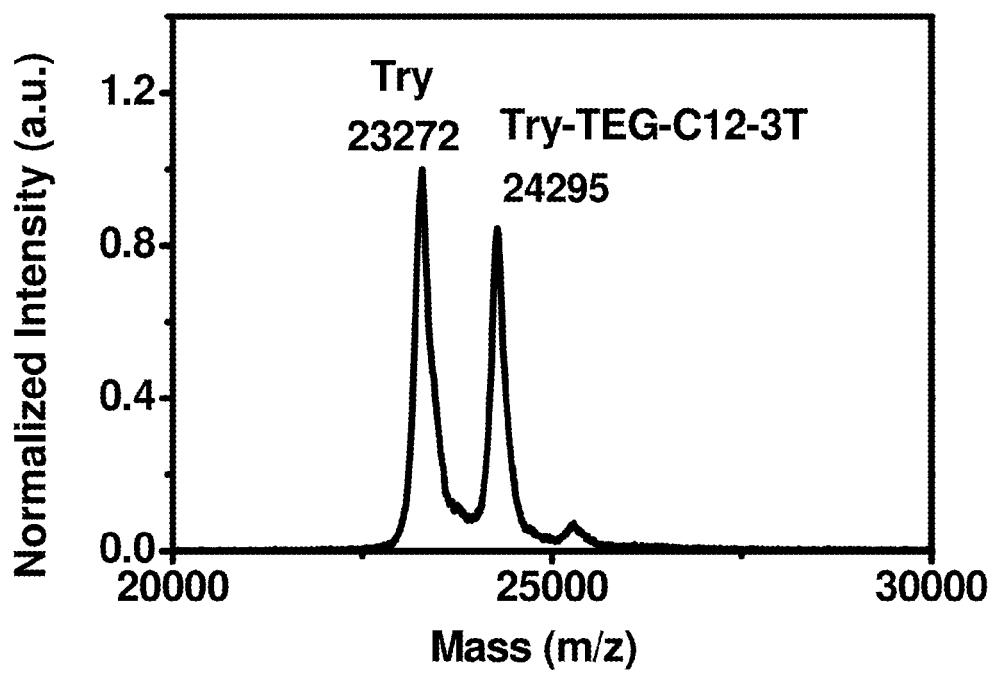
FIG. 2.1A
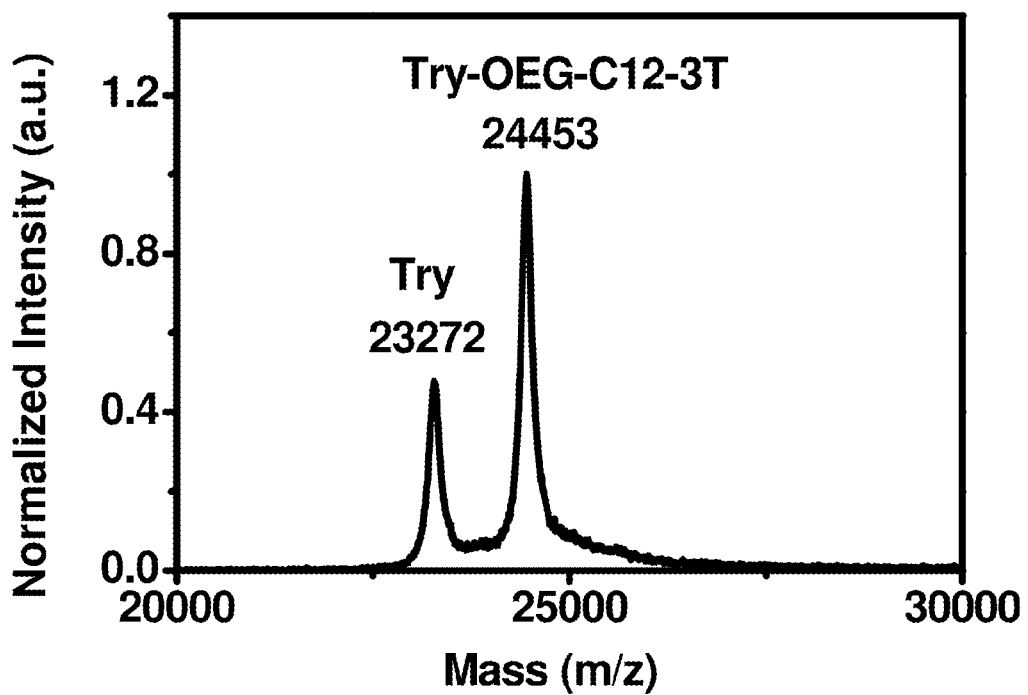
FIG. 2.1B

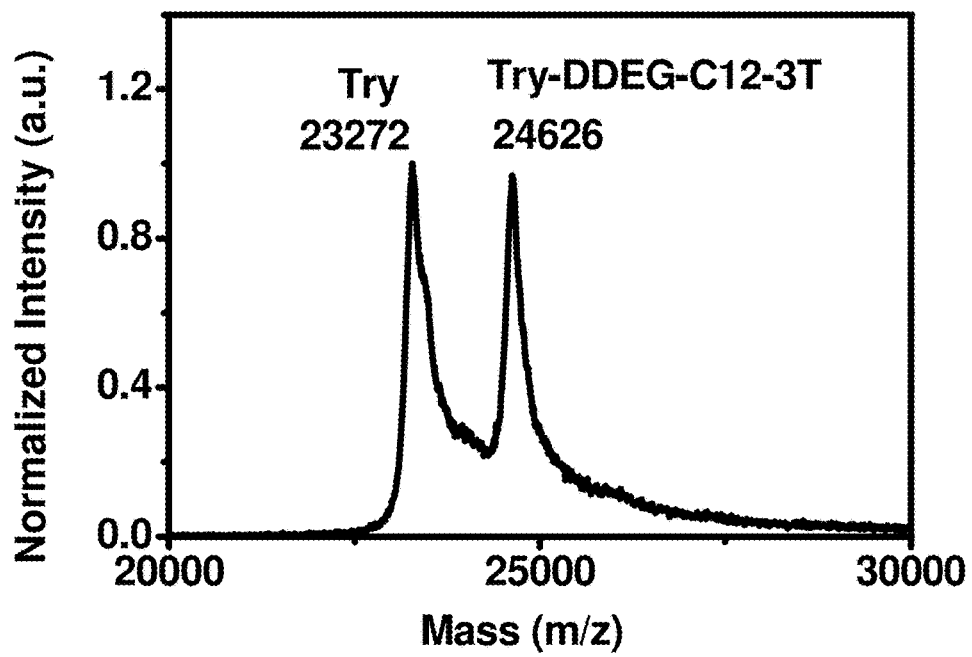
FIG. 2.1C
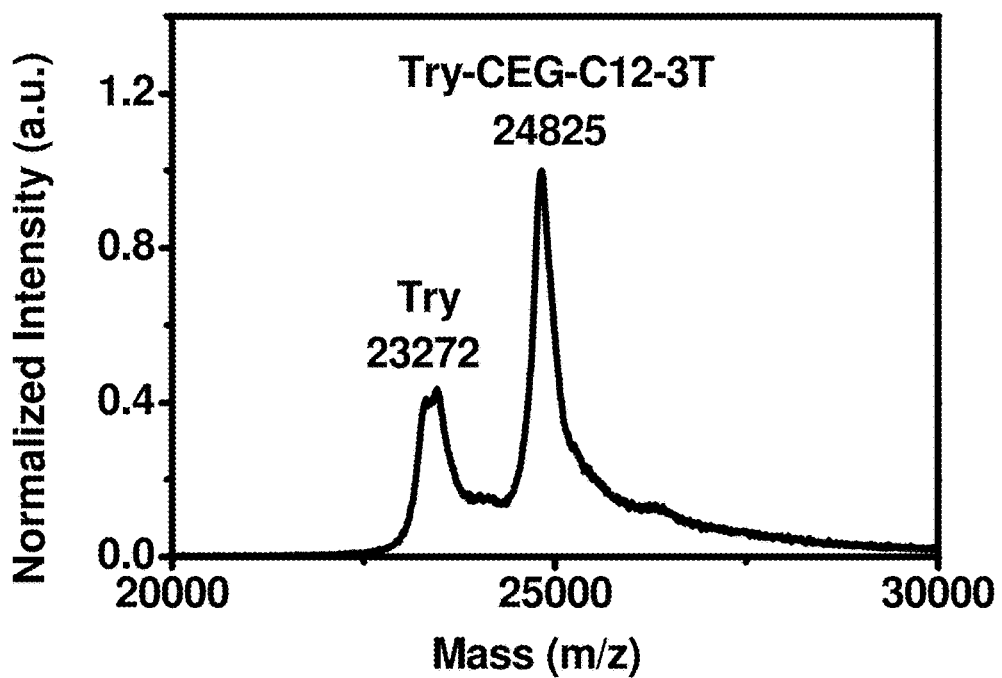
FIG. 2.1D

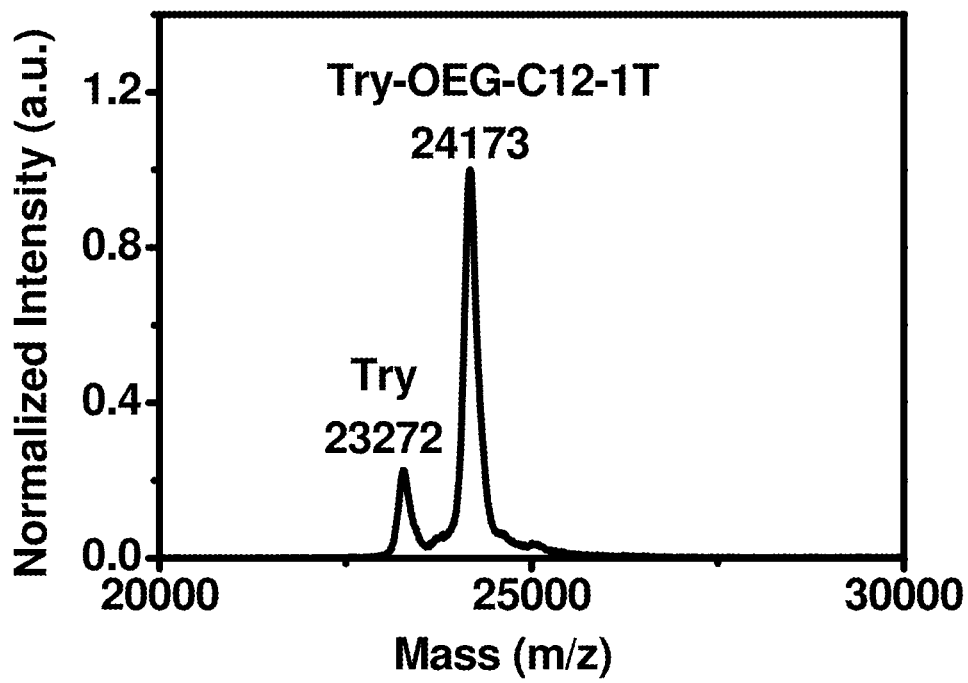
FIG. 2.2A
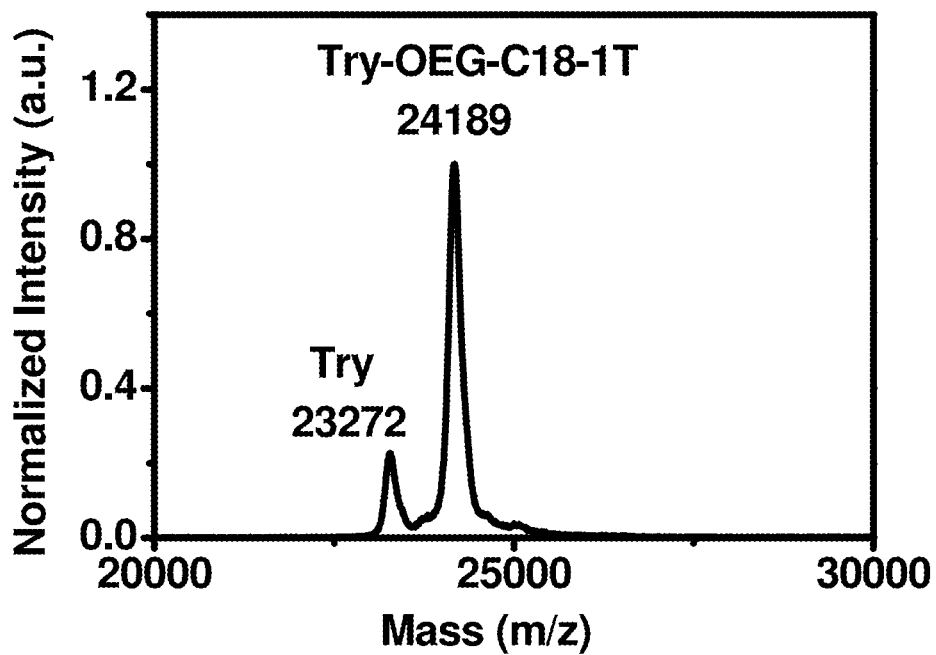
FIG. 2.2B

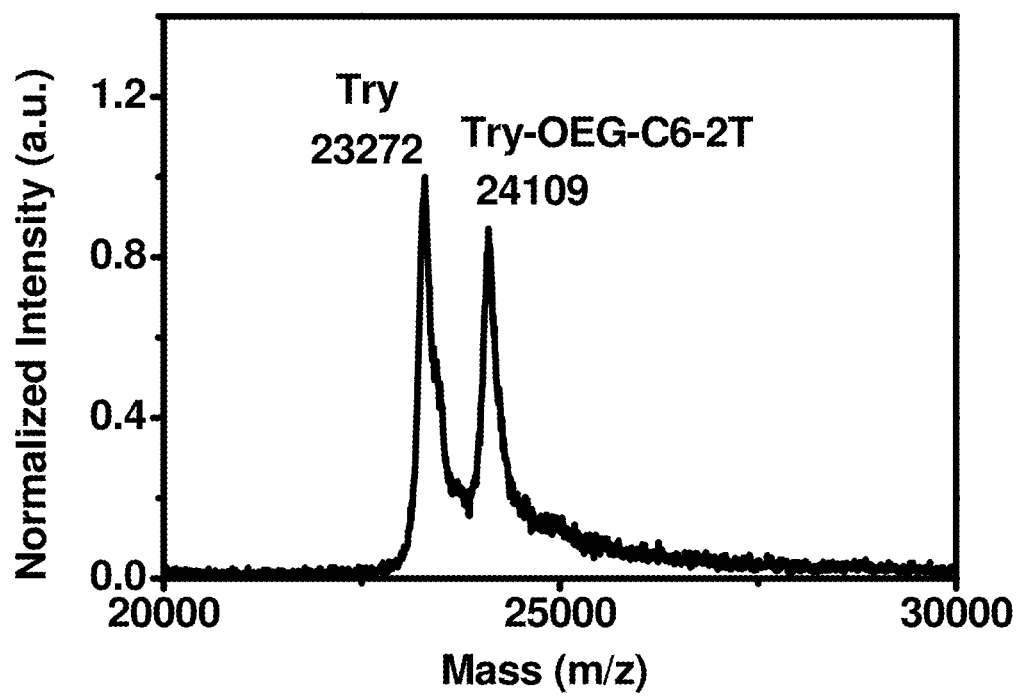
FIG. 2.2C
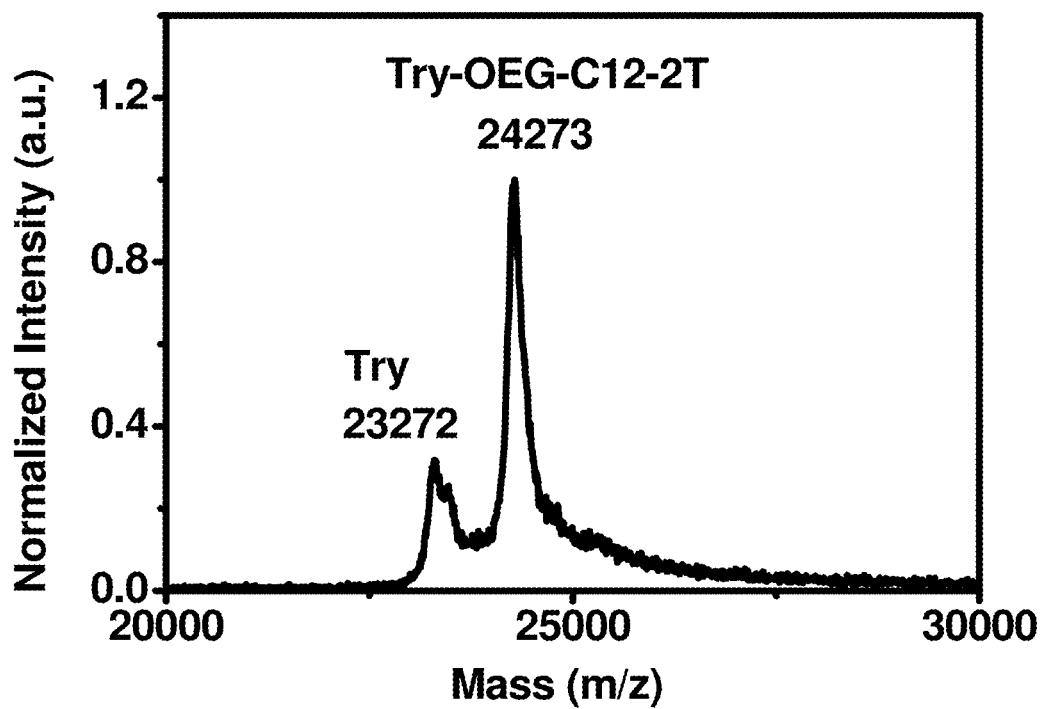
FIG. 2.2D

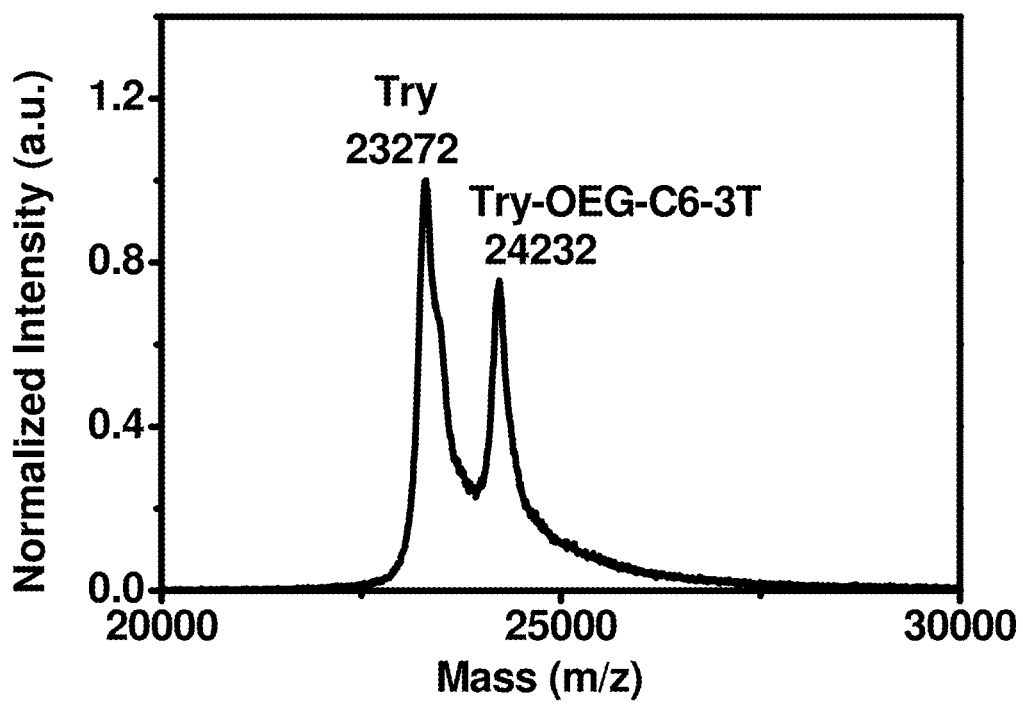
FIG. 2.3A
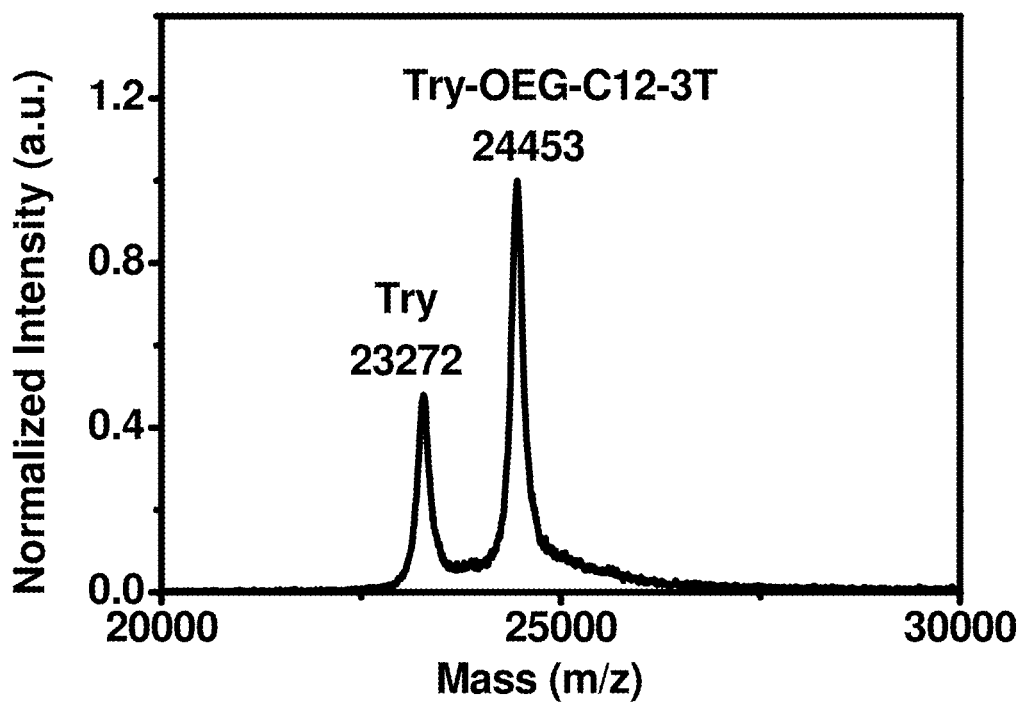
FIG. 2.3B

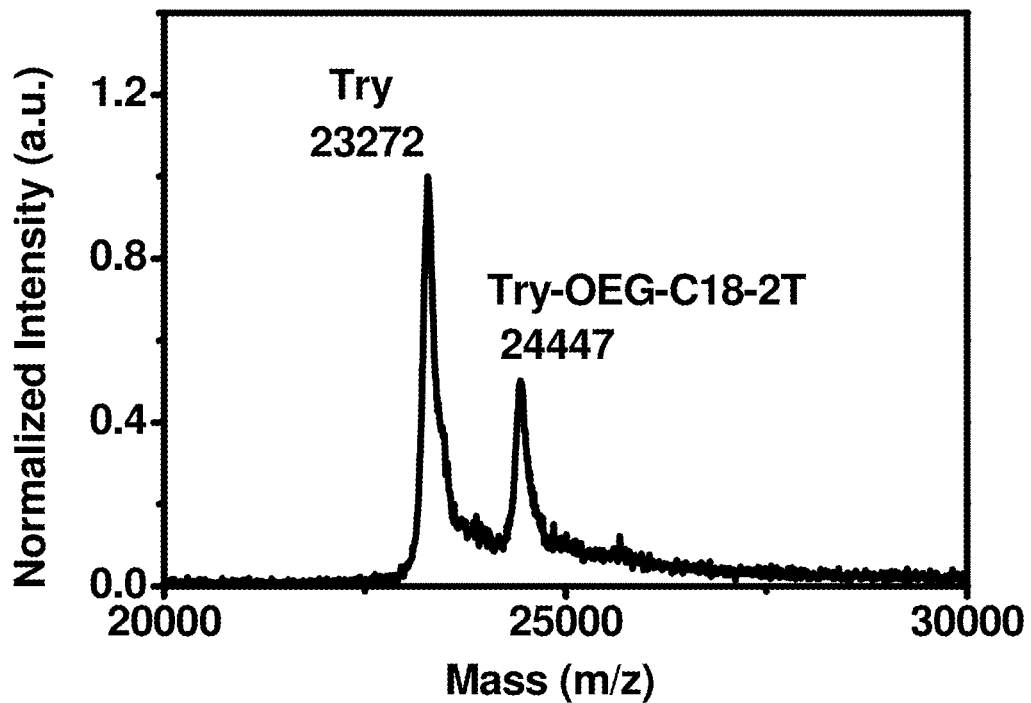
FIG. 2.3C
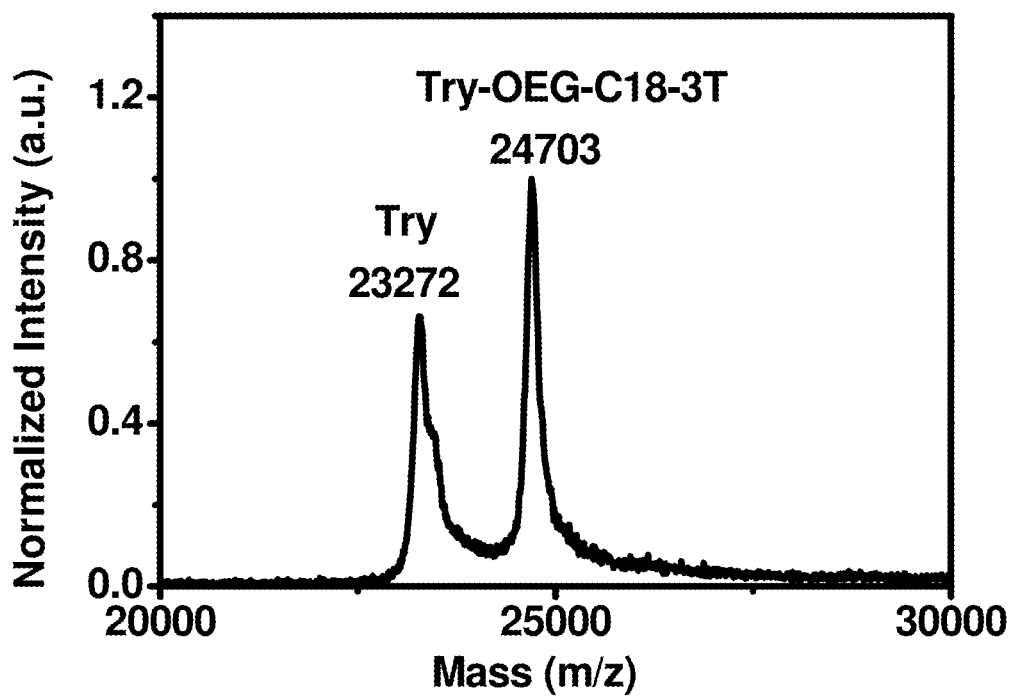
FIG. 2.3D

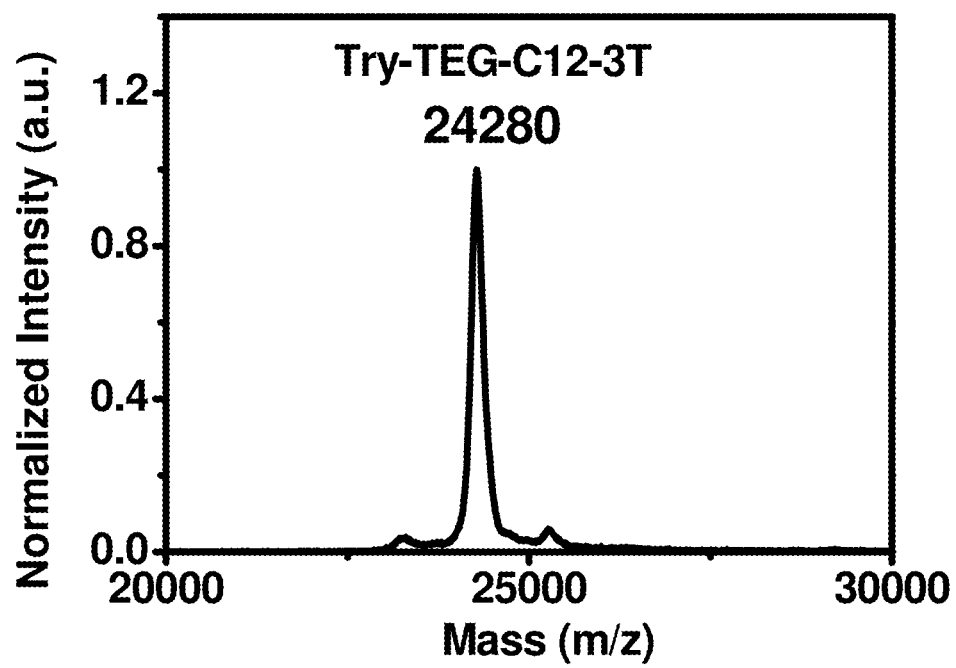
FIG. 4.1A
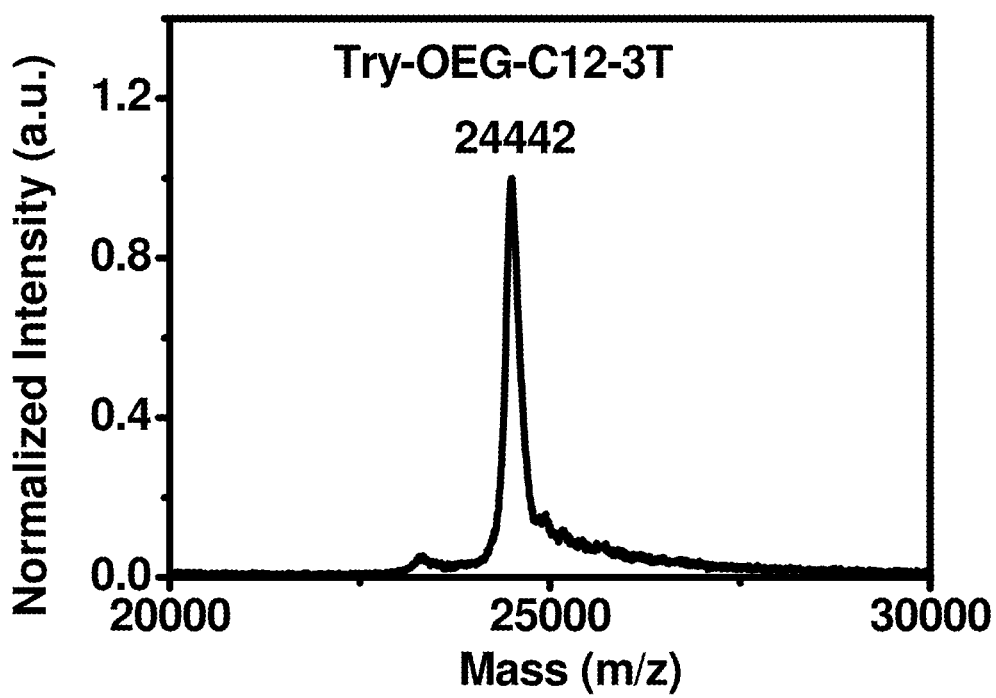
FIG. 4.1B

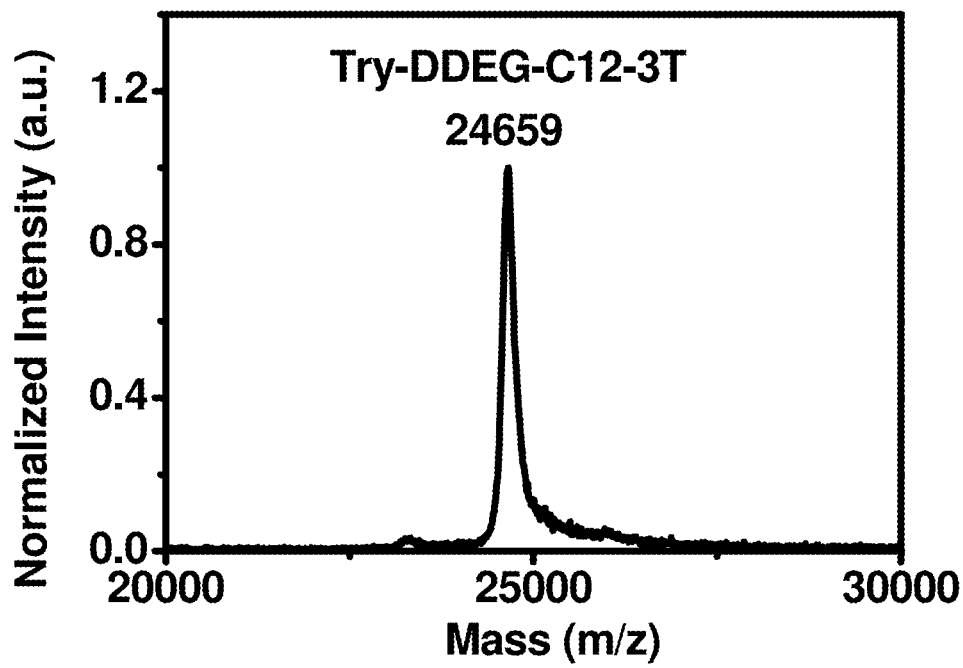
FIG. 4.1C
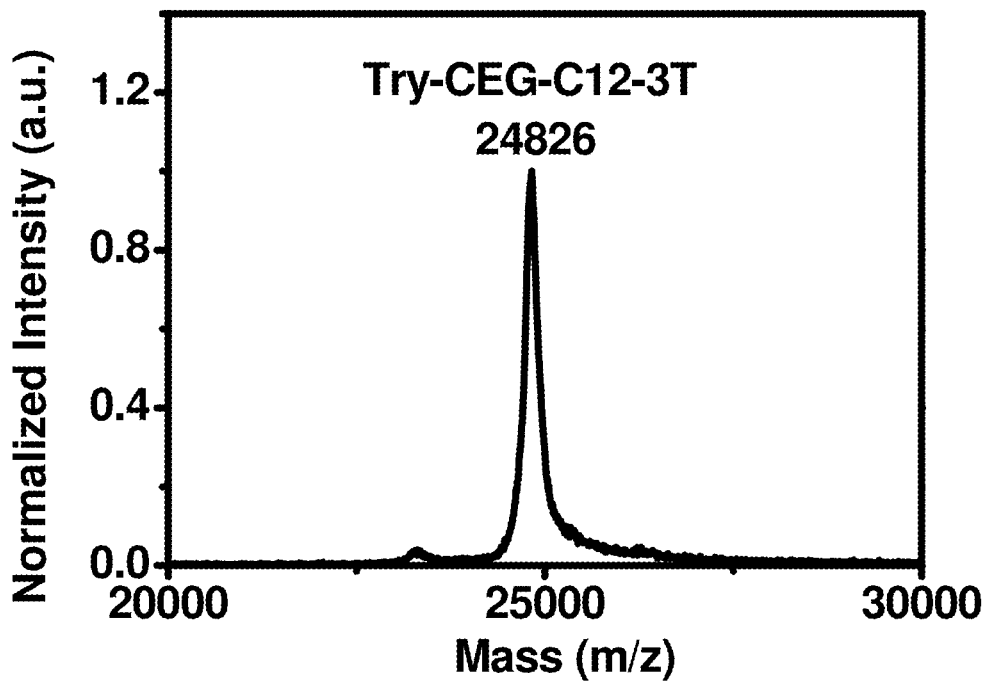
FIG. 4.1D

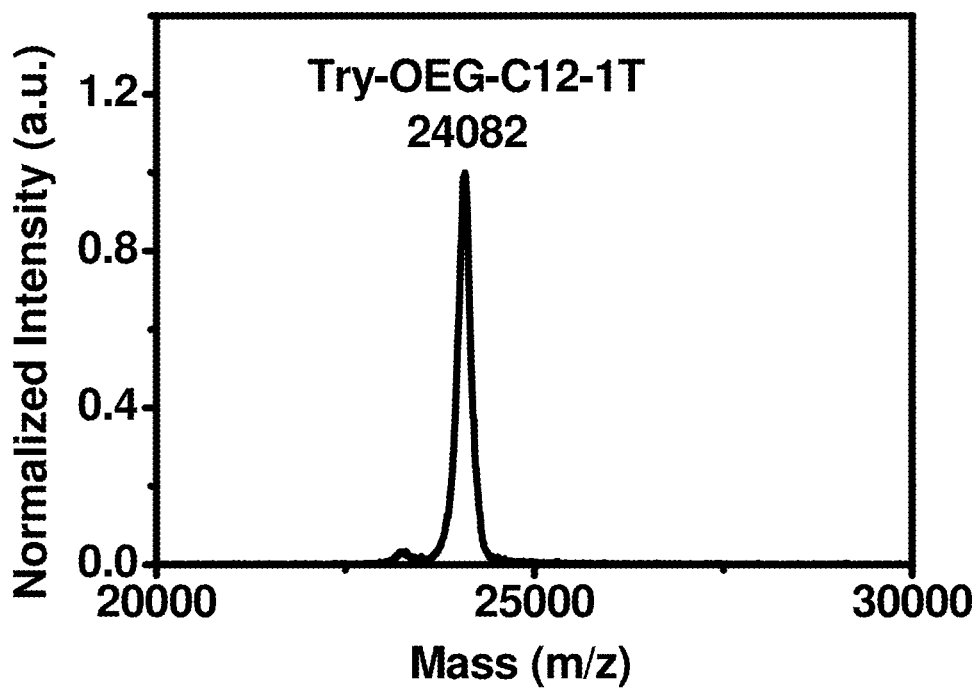
FIG. 4.2A
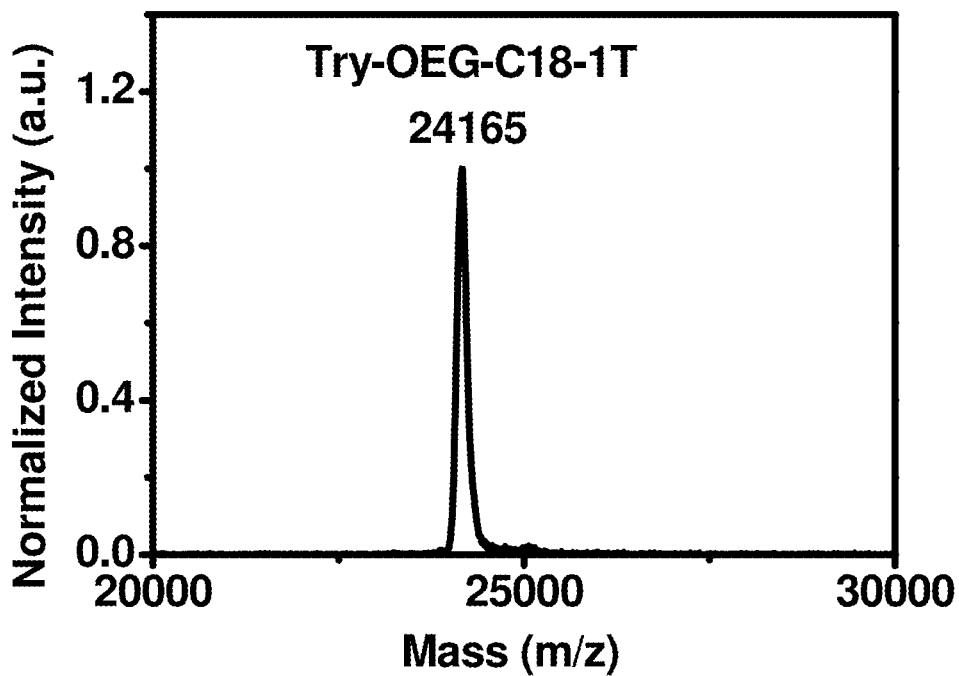
FIG. 4.2B

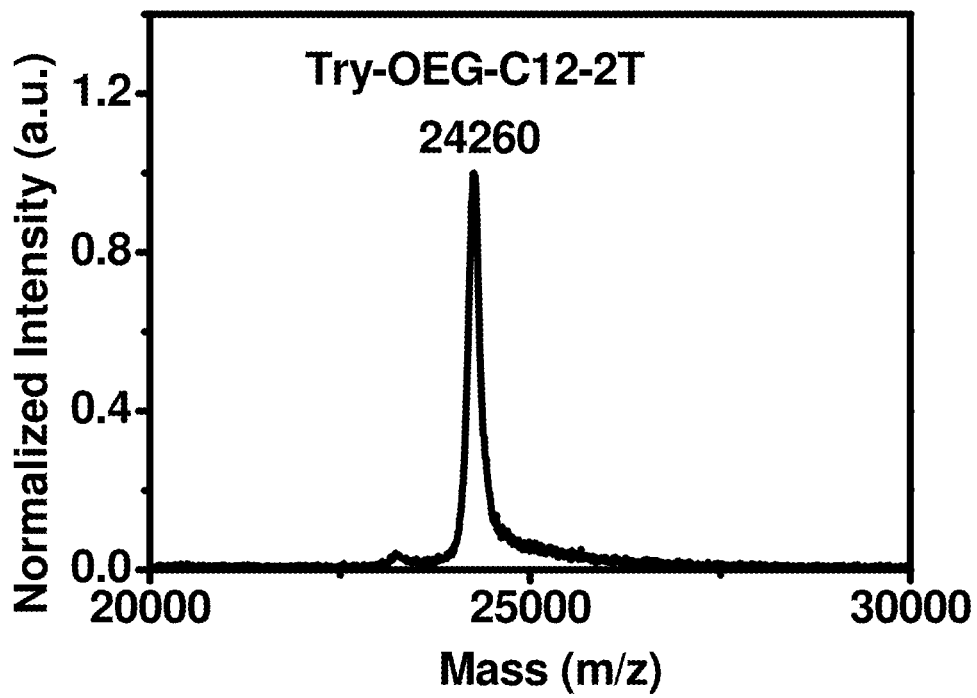
FIG. 4.2C
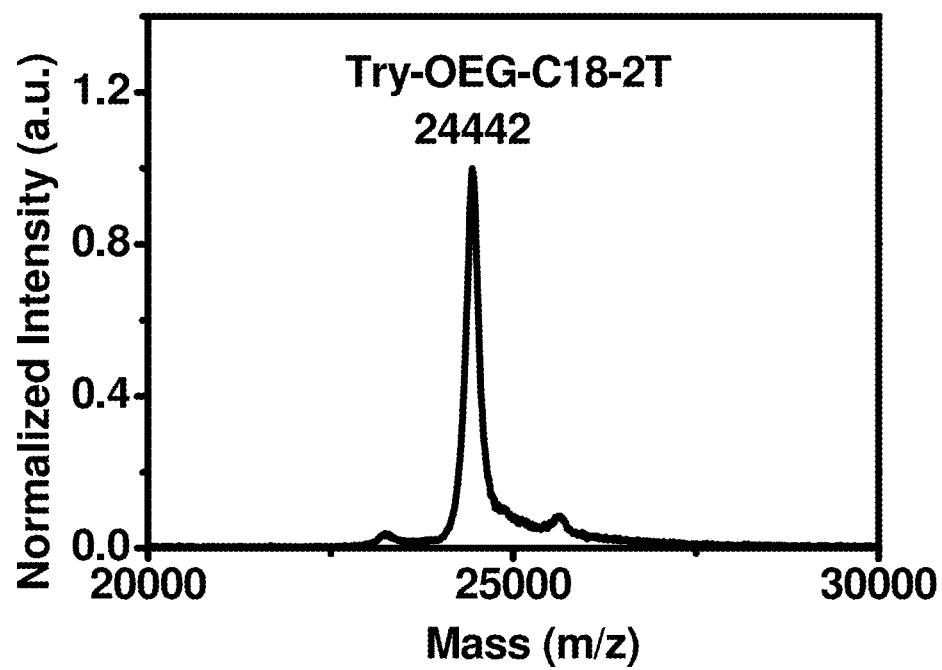
FIG. 4.2D

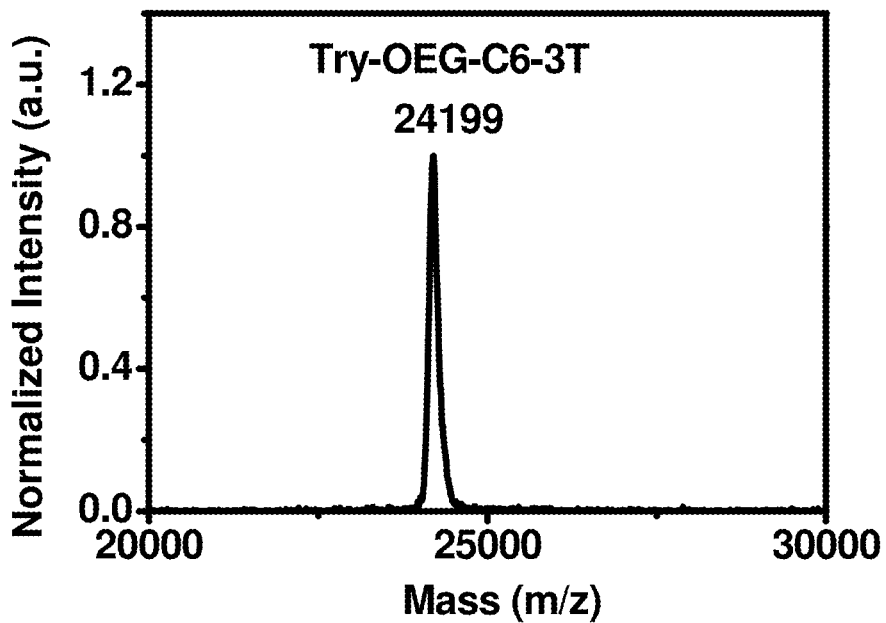
FIG. 4.2E
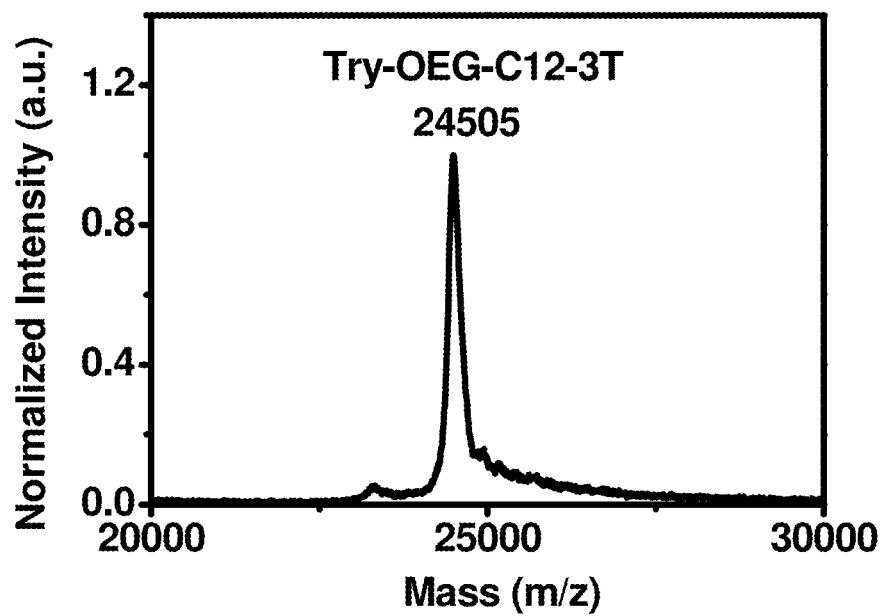
FIG. 4.2F

HYDROPHOBIN MIMICS: PROCESS FOR PREPARATION THEREOF

TECHNICAL FIELD OF THE INVENTION

The present invention relates to Hydrophobin mimics of formula (I) comprising a protein head group, hydrophilic linker and hydrophobic tail and to a process for synthesis of library of hydrophobin mimics thereof. The hydrophobin mimics of the present invention self-assemble to form protein nanoparticles/nanocontainer either alone or in a specified chemical environment. The hydrophobin mimics (I) of the present invention find application in bio-nanotechnology.

BACKGROUND AND PRIOR ARTS

Biomolecular nanotechnology is one of the emerging fields to design biological structures on natural scale. The technology includes using DNA, RNA, proteins, peptides, carbohydrates as templates for providing nanomaterials as multivalent scaffolds for drug delivery, enzyme inhibition and for vaccine development, glycan related biological and medical problems.

Self assembling of the biomaterials particularly composed of nucleic acids, peptides using DNA and RNA, for example, to create nanoshapes and patterns, molecular containers, three dimensional macroscopic crystals are disclosed in U.S. Pat. No. 675,039, US20160122392, U.S. Pat. No. 8,575,110 or U.S. Pat. No. 8,546,337.

Various state-of-the-art nanobiotechnologies for designing supramolecular protein complexes for the development of novel functional nanobiomaterials are discussed in the review article titled 'Design and construction of self-assembling supramolecular protein complexes using artificial and fusion proteins as nanoscale building blocks' by Naoya Kobayashi et. al published in Current Opinion in Biotechnology, Volume 46, August 2017, Pages 57-65.

To design proteins to self-assemble into a complex but well defined structure, the protein must contain multiple self assembling interfaces. The protein engineering comprises two general strategies, viz. rational protein design and directed evolution. In the rational protein design the detailed knowledge of the structure and function of the protein is accounted to make desired changes. The technique is relatively inexpensive and technically simple since the method involves site-directed mutagenesis. However, the technique has the major drawback in that in most instances the detailed structural knowledge of protein is often unavailable and further it may sometimes become difficult to predict the effects of various mutations.

In directed evolution, random mutagenesis is applied to a protein, and a selection regime is used to pick out variants that have the desired qualities. The drawback of the method is that it requires high-throughput screening which may not be feasible for all proteins.

Further, the functional group diversity in natural protein is limited to standard 20 amino acids and therefore diversity of protein scaffold is small which limits protein nanotechnology application. Moreover, most of the work related to protein nanotechnology is carried out using standard genetic engineering which is costly.

Hydrophobins, low molecular mass (≤20 kDa) secreted proteins of fungi, are characterized by moderate to high levels of hydrophobicity and the presence of eight conserved cysteine (Cys) residues. The amphiphilic structure possesses both hydrophilic and hydrophobic domains and can self-assemble from a soluble form into an insoluble and amphipathic monolayer at hydrophilic:hydrophobic interfaces. These protein monolayers can reverse the wettability of a surface, making them suitable for increasing the biocompatibility of many hydrophobic materials. The self-assembling properties and amphipathic nature of hydrophobins make them attractive candidates for biotechnological and medical applications.

Based on differences in hydropathy patterns and biophysical properties, the hydrophobins are classified into two categories viz. class I and class II. The Class I monolayer contains the similar core structure as amyloid fibrils, and is positive to Congo red and thioflavin T. The monolayer formed by class I hydrophobins has a highly ordered structure, and can only be dissociated by concentrated trifluoroacetate or formic acid. Monolayer assembly involves large structural rearrangements with respect to the monomer. The monolayers formed by class II hydrophobins lack the fibrillar rodlet morphology and can be solubilized with organic solvents and detergents.

Hydrophobins can be produced by fermentation of microorganisms (bacteria or fungi) or by fermentation of genetically modified microorganisms. These naturally occurring facially amphiphilic proteins present in micro-organisms and their structural aspects and mechanisms by which they assemble and the advancements in the use of hydrophobins for cell attachment, drug delivery, and protein purification are discussed in the documents; Two Forms and Two Faces, Multiple States and Multiple Uses: Properties and Applications of the Self-Assembling Fungal Hydrophobins by Qin Ren et. al. published on 31 Jul. 2013; Oligomerization of hydrophobin SC3 in solution: From soluble state to self-assembly by Xiaoqin Wang et. al published in Protein Science (2004); Structure-Function Relationships in Hydrophobins: Probing the Role of Charged Side Chains by Michael Lienemann et. al published in Applied and Environmental Microbiology, vol 79, no. 18, p. 5533-5538; Spontaneous self-assembly of SC3 hydrophobins into nanorods in aqueous solution by AgataZykwinska et. al published in Biochimica et BiophysicaActa 1844 (2014) 1231-1237.

During the past decade efforts are made for creating hydrophobins with improved properties and functions by bridging components derived from both natural and synthetic domains, specifically, to synthetic biomimetic packaging of functional proteins. Developing range of well-defined protein-polymer amphiphiles is very critical in clinical medical use such as in drug delivery of hydrophobic drugs, in vaccine development and for encapsulating drugs or bio macromolecules.

WO2012058343 describes protein based conjugates which comprises a globular protein conjugated with a polymer that preserves the folded and functional structure of a protein. The globular protein is covalently or non-covalently attached to the polymer and is selected from the group consisting of mCherry, a green fluorescent protein, lysozyme, albumin, and carbonic anhydrase. The polymer is a synthetic polymer. The conjugates self-assemble into a three dimensional solid-state or gel-state nanostructure.

US2016120814 describes a method for preparing a protein cage comprising; (i) 1st step of preparing an amphiphilic polymer comprising a 1st hydrophobic polymer and a 1st hydrophilic functional group; (ii) a 2nd step of preparing a hydrophilic protein comprising a 2nd functional group binding to the 1st functional group; (iii) a 3rd step of forming an amphiphilic polymer-protein hybrid by the binding of the 1st functional group and the 2nd functional group, and forming core-shell structured particles comprising a protein shell and an amphiphilic polymer core by the self-assembly of the amphiphilic polymer in a hydrophilic solvent; and (iv) a 4th step of removing some or all of the hydrophobic polymer of the core part from the core-shell structured particles. Example 1 illustrates the synthetic mechanism of the polymer bound to the Ni-NTA (Nitrilotriacetic acid) terminal as shown in the scheme below:

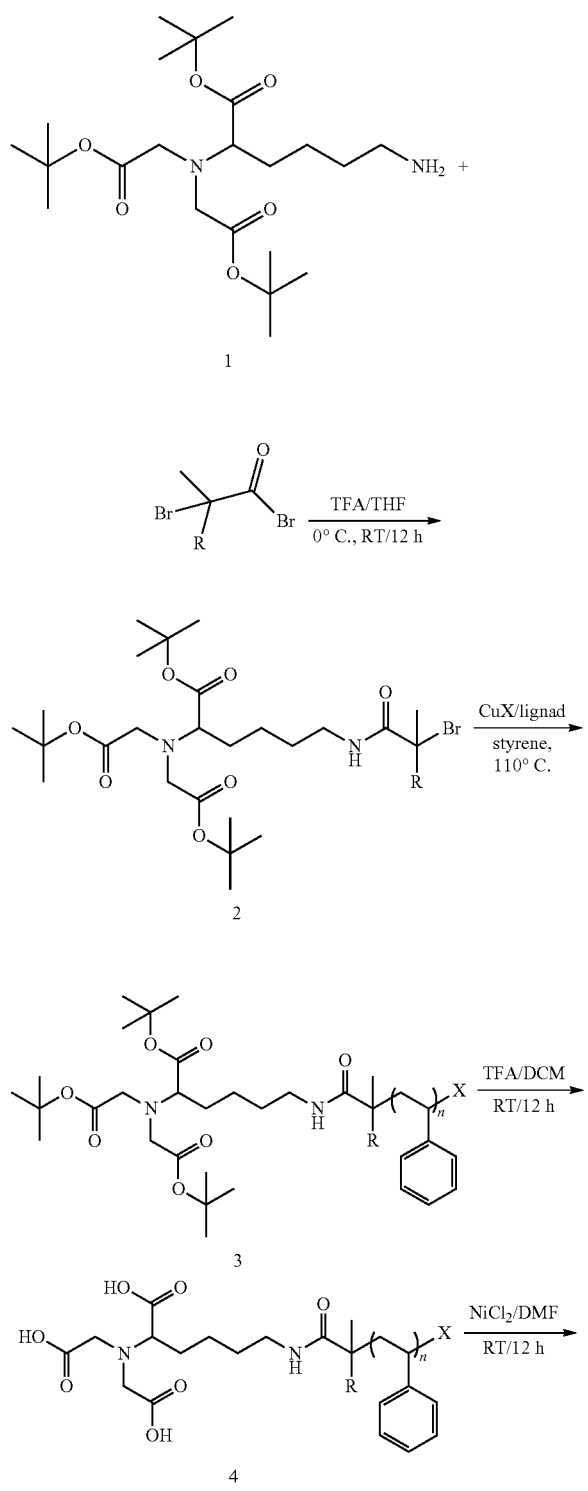

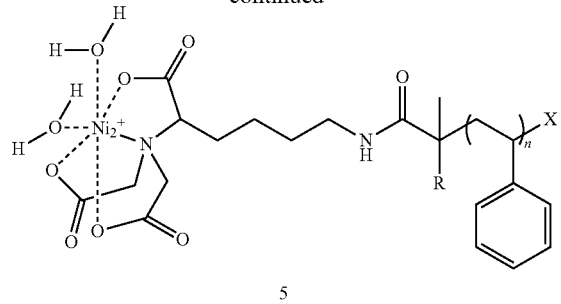

Article titled "Chemical Strategies for the Synthesis of Protein—Polymer Conjugates" by Bjorn Jung and Patrick Theato published in AdvPolymSci (2013) 253: 37-70; DOI: 10.1007/12_2012_169 reviews the numerous chemical strategies that have been developed to conjugate different synthetic polymers onto protein surfaces (deriving from selected amino acid residues), which are advantageous in biomedical applications.

In spite of the developments in the field of polymer directed protein assemblies there remains a need in the art to provide novel semi synthetic hydrophobin mimics that can self-assemble to protein nano container in a specified chemical environment for use in bio-nanotechnology.

The other objective is to expedite synthesis of hydrophobin mimics of different sizes and shapes with high precision.

Yet another objective is to create a library of hydrophobin mimics by tuning the protein head group, linker and hydrophobic part synthetically which is difficult to achieve in other reported method to cater to the needs of bio-nanotechnology.

SUMMARY OF THE INVENTION

In an aspect, the present invention provides hydrophobin mimics of varying size and shapes of formula I, depicted in FIG. 14, for use in bio-nano technology comprising;

The hydrophilic protein head group (A) includes PROT, selected from serine proteases, cysteine proteases, aspartic proteases, metalloproteases such as trypsin, chymotrypsin, subtilisin, proteinase K and the like with a length of up to 500 amino acids;

The hydrophilic spacer (B) comprising phosphonate ester of oligoethylene glycol wherein 'n' is an integer 1-30;

1T or 2T or 3T hydrophobic tail (C) wherein R represents C4-C30 (un)substituted or substituted straight, branched, cyclic or acyclic aliphatic, aromatic or alkyl phenyl moieties;

wherein the protein head group, linker and tail can be systematically changed one at a time.

The hydrophobin mimic of formula (I) can self assemble either alone or in a specified chemical environment to yield supramolecular protein assemblies.

In another aspect, the process for preparation of pure hydrophobin mimics with varying size and shapes of formula (I), comprising;

i. Self-assembling the hydrophobin mimic of formula (I) obtained by coupling the pre-weighed protein with the amphiphilic activity based probes (AABPs) (14), homogenized in triton-X-100 at pH in the range 7.0-7.5, either alone or in high salt concentrations;

ii. Removing triton X-100 from the protein mixture using ion exchange chromatography and eluting the native and hydrophobin mimic using eluting buffer solution;

iii. Removing the native protein from the hydrophobin mimic in high salt concentrations using size exclusion chromatography followed by desalting to obtain pure hydrophobin mimic.

In an aspect, the present invention discloses preparation of amphiphilic activity based probes (AABPs) comprising reacting diphosphonate ester of oligoethylene glycol (9d, 10d, 11d, 12d, 13d) with 1T or 2T or 3T hydrophobic azides using click chemistry followed by deprotection using oxalyl chloride to obtain monophosphonate ester intermediate; reacting this intermediate with diethyl amino sulfurtriflouride (DAST) to obtain amphiphilic activity based probes (AABPs).

In another aspect, the 1T or 2T or 3T hydrophobic azides are prepared comprising the following steps;
  i. Refluxing mixture of 4-hydroxybenzyl alcohol (in the case of 1T) or di/tri hydroxy ester with alkyl bromide (in the case of 2T or 3T), base, potassium iodide and crown ether in a solvent to obtain mono or di or tri-O-alkyl protected alcohol or esters;
  ii. Reducing di- or tri-O-alkyl protected esters using reducing agent in a solvent to obtain the alcohol derivative;
  iii. Halogenating the alcohol derivative to obtain the halo derivative;
  iv. Reacting the halo derivative with sodium azide in a solvent to yield 1T or 2T or 3T hydrophobic azides.

In yet another aspect, the hydrophobin mimics of formula I is selected from the group consisting of:
  i. conjugate of serine protease and ethyl (1-(1-(3,4,5-tris(dodecyloxy)benzyl)-1H-1,2,3-triazol-4-yl)-2,5,8,11,14,17,20,23-octaoxapentacosan-25-yl) phosphono fluoridate (serine protease-C12-3T)
  ii. conjugate of trypsin and ethyl (1-(1-(4-(dodecyloxy)benzyl)-1H-1,2,3-triazol-4-yl)-2,5,8,11,14,17,20,23-octaoxapentacosan-25-yl)phosphonofluoridate (trypsin-OEG-C12-1T);
  iii. conjugate of trypsin and ethyl (1-(1-(4-(octadecyloxy)benzyl)-1H-1,2,3-triazol-4-yl)-2,5,8,11,14,17,20,23-octaoxapentacosan-25-yl)phosphonofluoridate (trypsin-OEG-C18-1T);
  iv. conjugate of trypsin and ethyl (1-(1-(3,5-bis(hexyloxy)benzyl)-1H-1,2,3-triazol-4-yl)-2,5,8,11,14,17,20,23-octaoxapentacosan-25-yl)phosphonofluoridate (Trypsin-OEG-C6-2T);
  v. conjugate of trypsin and ethyl (1-(1-(3,5-bis(dodecyloxy)benzyl)-1H-1,2,3-triazol-4-yl)-2,5,8,11,14,17,20,23-octaoxapentacosan-25-yl)phosphonofluoridate (trypsin-OEG-C12-2T);
  vi. conjugate of trypsin and ethyl (1-(1-(3,5-bis(octadecyloxy)benzyl)-1H-1,2,3-triazol-4-yl)-2,5,8,11,14,17,20,23-octaoxapentacosan-25-yl)phosphonofluoridate (trypsin-OEG-C18-2T);
  vii. conjugate of trypsin and ethyl (1-(1-(3,4,5-tris(hexyloxy)benzyl)-1H-1,2,3-triazol-4-yl)-2,5,8,11,14,17,20,23-octaoxapentacosan-25-yl)phosphonofluoridate (trypsin-OEG-C6-3T);
  viii. conjugate of trypsin and ethyl (1-(1-(3,4,5-tris(dodecyloxy)benzyl)-1H-1,2,3-triazol-4-yl)-2,5,8,11,14,17,20,23-octaoxapentacosan-25-yl)phosphonofluoridate (trypsin-OEG-C12-3T);
  ix. conjugate of trypsin and ethyl (1-(1-(3,4,5-tris(octadecyloxy)benzyl)-1H-1,2,3-triazol-4-yl)-2,5,8,11,14,17,20,23-octaoxapentacosan-25-yl)phosphonofluoridate(trypsin-OEG-C18-3T);
  x. Conjugate of trypsin and Ethyl (2-(2-((1-(3,4,5-tris(dodecyloxy)benzyl)-1H-1,2,3-triazol-4-yl)methoxy)ethoxy)ethyl)phosphonofluoridate (trypsin-DEG-C12-3T)
  xi. Conjugate of trypsin and ethyl (1-(1-(3,4,5-tris(dodecyloxy)benzyl)-1H-1,2,3-triazol-4-yl)-2,5,8,11-tetraoxatridecan-13-yl)phosphonofluoridate (trypsin-TEG-C12-3T)
  xii. Conjugate of trypsin and ethyl (1-(1-(3,4,5-tris(dodecyloxy)benzyl)-1H-1,2,3-triazol-4-yl) 2,5,8,11,14,17,20,23,26,29,32,35-dodecaoxaheptatriacontan-37-yl) phosphonofluoridate (trypsin-DDEG-C12-3T)
  xiii. Conjugate of trypsin and ethyl (1-(1-(3,4,5-tris(dodecyloxy)benzyl)-1H-1,2,3-triazol-4-yl)-2,5,8,11,14,17,20,23,26,29,32,35,38,41,44,47-hexadecaoxanonatetracontan-49-yl)phosphonofluoridate (trypsin-CEG-C12-3T)

DETAILED DESCRIPTION OF THE INVENTION

The invention will now be described in its various preferred as well as optional embodiments, so that the various aspects therein will be more clearly understood and appreciated.

The present invention designed by the inventors helps to engineer protein nano assemblies having the ability to change protein head group, linker length and hydrophobic tail of hydrophobin mimics represented by general formula (I). The hydrophobin mimics of the present invention thus opens up new avenues for the use of these nanoscaffolds in bio-nanotechnology applications, the size of the protein assemblies of the present invention can be programmed. The ability to change protein head group, linker length and hydrophobic tail of hydrophobin mimics (formula I) provides an opportunity to make supramolecular protein assembly of defined shape and size. The micelle-assisted conjugation strategy is used in the present invention to attach hydrophobic group on to a globular protein. The modular synthetic strategy allows easy interchange of core structural units of molecular design to create a library of hybrid biomacromolecules with very rich structural variants.

The hydrophobin mimic designed in the present invention possess facially amphiphilic character similar to natural hydrophobins from fungi (HFBII) and bacteria (BslA), respectively.

In an embodiment, the present invention discloses hydrophobin mimics of varying size and shapes of formula I which can self-assemble to protein nano containers for use in bio-nano technology applications.

Figure 12:
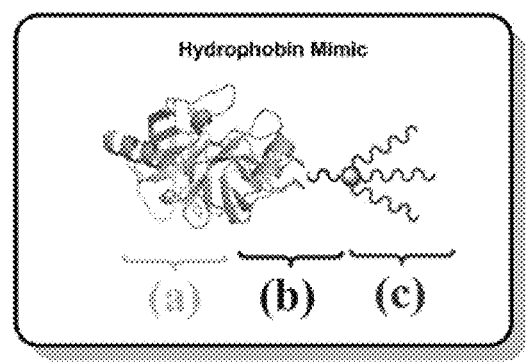
FIG. 12 is the Schematic representation of hydrophobin mimic of formula (I).
Figure 14:
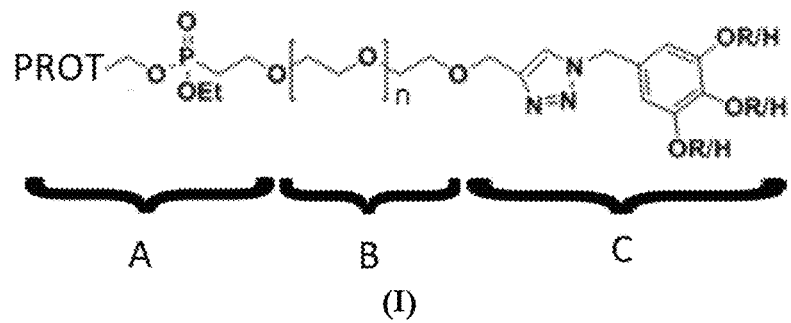
FIG. 14 depicts a hydrophobin mimic of formula I.

The hydrophobin mimic of formula (I), as depicted in FIG. 14, comprises a hydrophilic protein head group (A) comprising PROT, where PROT is selected from serine proteases, cysteine proteases, aspartic proteases, metalloproteases such as trypsin, chymotrypsin, subtilisin or proteinase K and the like with a length of up to 500 amino acids; the hydrophilic spacer (B) comprising phosphonate ester of oligoethylene glycol; wherein 'n' is an integer 1-30; 1T or 2T or 3T hydrophobic tails (C) wherein each "R/H" represents H or C4-C20 (un)substituted or substituted straight, branched, cyclic or acyclic aliphatic, aromatic or alkylphenyl moieties; wherein protein head group, linker and tail can be systematically changed one at a time, with the proviso that at least one R/H is not each. A schematic representation of the hydrophobin mimic of formula (I) is depicted in FIG. 12.

The hydrophobin mimics of formula (I) have particle size in the range of 1-10 nm.

In another embodiment, the present invention discloses a process for synthesis of hydrophobin mimics of formula (I) which contain three core structural units, i.e. hydrophilic protein head group, hydrophilic spacer and a hydrophobic tail which can self-assemble to protein nano container either alone or in a specified chemical environment.

The process of the present invention has the ability to incorporate any chemical entity, both small and macromolecule, or to systematically change the groups one at a time to design the protein amphiphile of varying size and shapes.

The process for synthesis of novel hydrophobin mimics (I) is described in the various embodiments as follows:

A: Preparation of 1T or 2T or 3T Hydrophobic Azides from Mono or Di or Trihydroxy Esters:

Accordingly, in step (i) to the 4-hydroxybenzyl alcohol or di or tri hydroxy ester is added alkyl bromide, crown ether, base and potassium iodide and the mixture is refluxed in a solvent until completion of the reaction to obtain mono or di or tri-O-alkyl protected alcohol (for 1T) or esters (for 2T and 3T). The reaction mixture is neutralized with acidic water and then extracted in a solvent. The combined organic layers are dried, the solvent evaporated to yield the crude protected ester which is further purified.

Step (ii) comprises reducing the ester of step (i) with a reducing agent in a solvent at 0° C. followed by raising the temperature to room temperature with continued stirring until completion of the reaction. This is followed by adding water to the reaction mixture and stirring until colour of the reaction mixture changes to half white. The resulting solution is filtered and further washed with suitable solvent, dried, concentrated and purified to obtain the alcohol derivative.

Step (iii) includes halogenating alcohol derivative of step (ii) with triphenylphosphine ($PPh_3$) and tetrabromomethane ($CBr_4$) or with thionyl chloride and stirring until completion of the reaction. The solvent is then evaporated and the residue is extracted in a mixture of water and solvent, drying the combined organic layers, concentrating and purifying to obtain the bromide/chloride derivative.

Step (iv) comprises of reacting the bromide/chloride derivative of step (iii) with sodium azide and stirring in a solvent until completion of the reaction. The mixture is extracted in a solvent, washed, dried, concentrated and purified to yield the 1T or 2T or 3T hydrophobic azides (1).

The solvent used in the processes of step (i) is selected from polar or non-polar protic or aprotic solvents such as lower alcohols, ethers such as dioxane, THF; DMF, halogenated hydrocarbons; ketones and the like.

The base used in step (i) is selected from organic or inorganic bases, preferably inorganic base such as carbonates or bicarbonates of alkali or alkaline earth metals; most preferably alkali earth metal carbonates. The reducing agent in step (ii) is selected from alkali metal hydrides such as $NaBH_4$, $LiAlH_4$, diisobutylaluminum hydride (DIBAL); preferably $LiAlH_4$.

In an embodiment, 4-hydroxybenzyl alcohol is obtained by reduction of 4-hydroxybenzaldehyde and di or tri hydroxy ester is obtained by conventional method of esterification of acid with an alcohol.

In a preferred embodiment, the 4-hydroxybenzyl alcohol 1T) or di (2T) or tri hydroxy ester (3T) is selected from di or tri hydroxy benzoates to obtain 1T or 2T or 3T hydrophobic azides by the process steps described in steps (i) to (iv) above.

The process for conversion of 4-hydroxybenzyl alcohol or di or tri hydroxy benzoate to 1T or 2T or 3T hydrophobic azide is represented in Scheme 1 (a), (b), and (c) below: Scheme 1(a) discloses synthesis of 1T hydrophobic azides, wherein R is $C_{12}H_{25}$, $C_{18}H_{37}$. Scheme 1(b) discloses synthesis of 2T hydrophobic azide from dihydroxy benzoate, wherein R is $C_6H_{13}$, $C_{12}H_{25}$, or $C_{18}H_{37}$. 3T hydrophobic azide is obtained from trihydroxy benzoate, as shown in Scheme 1(c), wherein R is $C_6H_{13}$, $C_{12}H_{25}$, or $C_{18}H_{37}$.

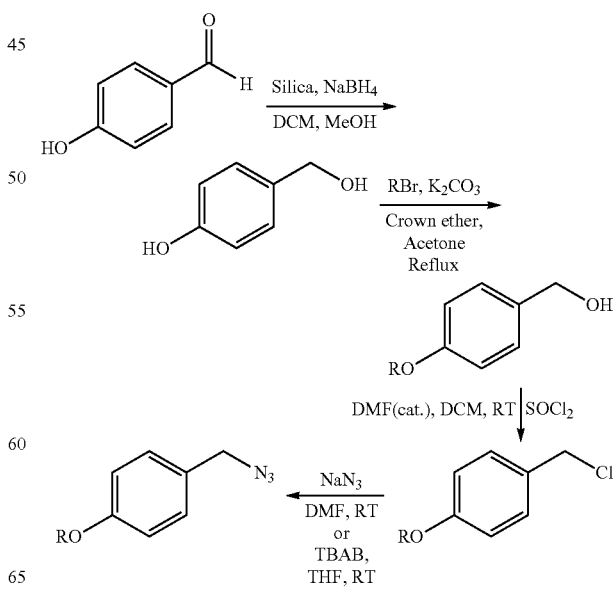

Scheme 1(a)

Scheme 1(b)

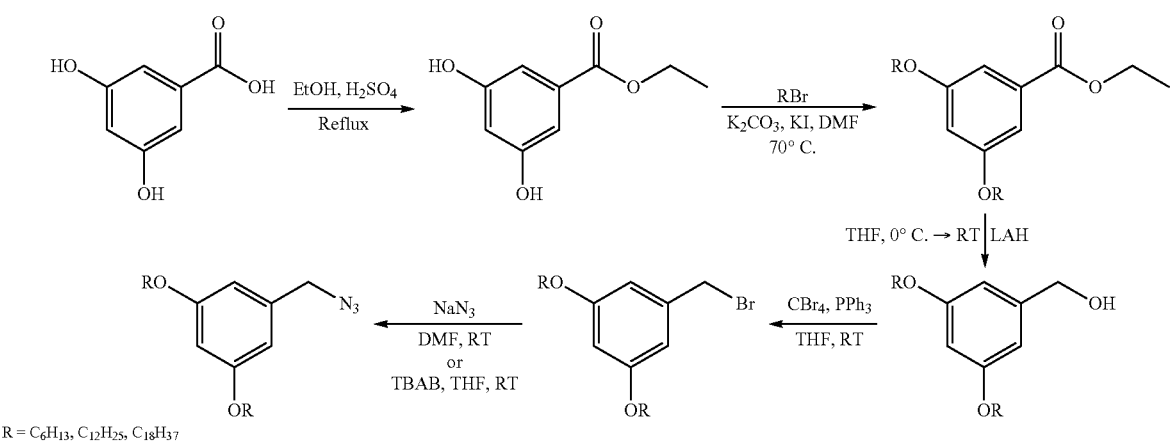

R = C₆H₁₃, C₁₂H₂₅, C₁₈H₃₇

Scheme 1(c)

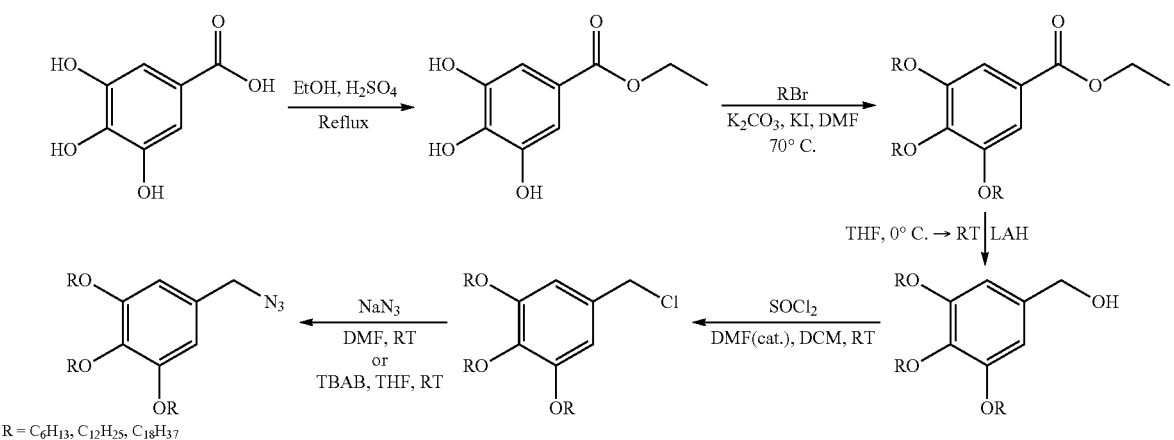

R = C₆H₁₃, C₁₂H₂₅, C₁₈H₃₇

B. The Preparation of Phosphonate Ester of Oligoethylene Glycol Spacers Includes the Following Steps.

i. Synthesis of Di and Tetra Ethylene Glycol Spacers

Accordingly, step (i) comprises reacting di or tetra ethylene glycol with a strong base selected from metal hydrides such as sodium hydride or potassium hydride in a solvent at 0° C. followed by addition of propargyl bromide at same temperature and stirring the mixture at room temperature until completion of the reaction. Upon completion of the reaction, excess metal hydride is quenched with drop wise addition of water, extracting the reaction mixture in a solvent, drying the combined organic layers, concentrating and purifying to obtain desired propargylated compound (9a, 10a).

Step (ii) comprises tosylating the other portion of monopropargylated di or tetra ethylene glycol with tosyl chloride to obtain tosylated compound (9b, 10b). Accordingly, oligoethylene glycol is dissolved in a solvent followed by addition of aqueous base selected from sodium hydroxide or potassium hydroxide, preferably potassium hydroxide in small portions. This is followed by dropwise addition of solution of tosyl chloride and stirring the mixture until completion of the reaction. After the reaction is complete, the reaction mixture is quenched with aqueous ammonium chloride and extracted in the solvent to obtain crude tosylated product which is further purified.

Step (iii) comprises refluxing the compound (9b or 10b) obtained in the above with KI in acetone until completion of the reaction, filtering the excess KI and further washing with acetone. Evaporating the acetone fraction and extracting the residue in the solvent, washing and concentrating to obtain crude product (10) which is further purified.

Step (iv) This is followed by refluxing the compound (9c or 10c) with triethylphosphite (P(OEt)₃) to obtain phosphonate ester (9d or 10d). Excess of triethylphosphite (P(OEt)₃) is removed under vacuum and purified.

The solvent used in the processes is selected from polar or non-polar protic or aprotic solvents such as lower alcohols, ethers such as dioxane, THF; DMF, halogenated hydrocarbons; ketones and the like. In a preferred embodiment, the oligoethylene glycol is di (DEG) and tetra (TEG). The preparation of phosphonate ester by the process described above in steps (i) to (iv) is depicted in Scheme 2a.

Scheme 2a

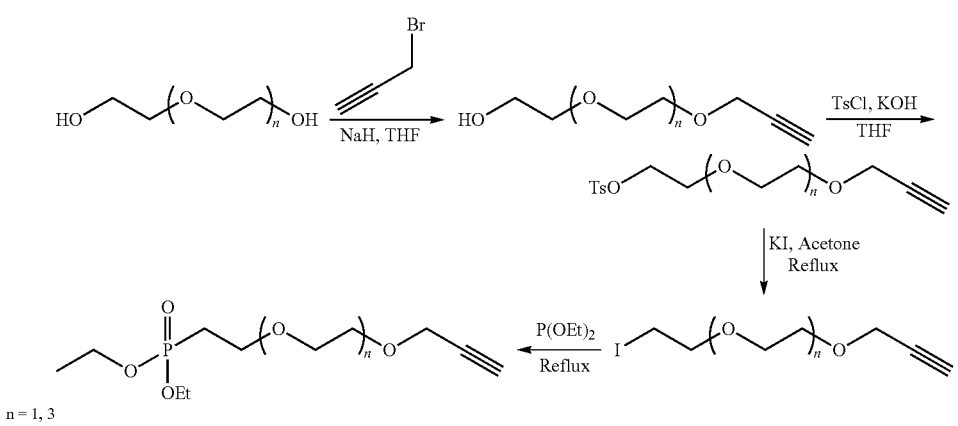

ii. Synthesis of Octa, Dodeca and Cetyl Ethylene Glycol Spacers

Accordingly, step (i) comprises reacting tetraethylene glycol with a strong base selected from metal hydrides such as sodium hydride or potassium hydride in a solvent at 0° C. followed by addition of propargylated monotosyl ethylene glycol derivative (containing 'n' units of ethylene glycol) at same temperature and stirring the mixture at room temperature until completion of the reaction. Upon completion of the reaction, excess metal hydride is quenched with drop wise addition of water, extracting the reaction mixture in a solvent, drying the combined organic layers, concentrating and purifying to obtain desired propargylated compound with the number of ethylene glycol units increased by 4 (11a, 12a, 13a).

Step (ii) comprises tosylating the other portion of oligoethylene glycol with tosyl chloride to obtain tosylated compound (11b, 12b, 13b). Accordingly, oligoethylene glycol, DMAP and tosyl chloride is dissolved in a solvent followed by addition of aqueous base selected from triethyl amine in small portions. Upon completion, reaction was quenched by dropwise addition of water and extracted with DCM thrice.

Step (iii) comprises refluxing the compound (11b or 12b or 13b) obtained in the above step with KI in acetone until completion of the reaction, filtering the excess KI and further washing with acetone. Evaporating the acetone fraction and extracting the residue in the solvent, washing and concentrating to obtain crude product (10) which is further purified.

Step (iv) This is followed by refluxing the compound (11c or 12c or 13c) with triethylphosphite ($P(OEt)_3$) to obtain phosphonate ester (11d, 12d, 13d). Excess of triethylphosphite ($P(OEt)_3$) is removed under vacuum and purified.

The solvent used in the processes is selected from polar or non-polar protic or aprotic solvents such as lower alcohols, ethers such as dioxane, THF; DMF, halogenated hydrocarbons; ketones and the like. In a preferred embodiment, the oligoethylene glycol is octa (OEG), dodeca (DDEG) and cetyl ethylene glycol (CEG) spacers. The preparation of phosphonate ester by the process described above in steps (i) to (iv) is depicted in Scheme 2b.

Scheme 2b

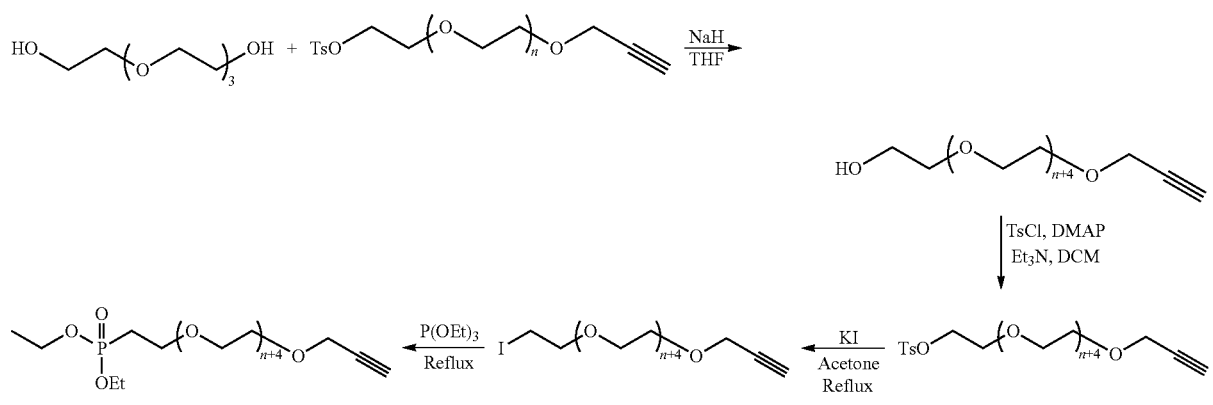

C: Preparation of Amphiphilic Activity Based Probes (AABPs) Comprises the Following Steps.

The process step involves conjugation of the hydrophilic phosphonate ester (as shown in scheme 2) with the hydrophobic azides (as shown in Scheme 3) using click chemistry.

Accordingly, step (i) for the preparation of AABPs comprises adding freshly prepared sodium ascorbate and $CuSO_4$ to the reaction mixture containing the azide and phosphonate ester dissolved in a solvent, at least three times at an interval of 45 minutes until completion of the reaction. Upon completion, the reaction mixture is extracted in the solvent, the combined organic layers are dried, concentrated to get the crude product which is further purified.

Deprotection of the diphosphonate ester is carried out using oxalyl chloride in a solvent at room temperature to obtain mono phosphonate ester. To the solution of mono-phosphonate ester is added diethylaminosulfur triflouride (DAST) at room temperature and allowed to react. After the reaction is complete, excess of DAST and the solvent are removed and the residue is quenched with water to remove any traces of DAST. The reaction mixture is extracted in the solvent, and the combined organic layer is concentrated to obtain the crude fluoro substituted AABPs probe which is used directly for conjugation with protein without further purification.

The solvent used in the processes is selected from polar or non-polar protic or aprotic solvents such as lower alcohols, ethers such as dioxane, THF; DMF, halogenated hydrocarbons; ketones and such like. The process is shown below in Scheme 3.

Scheme 3

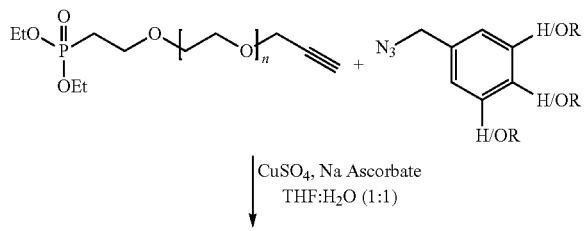

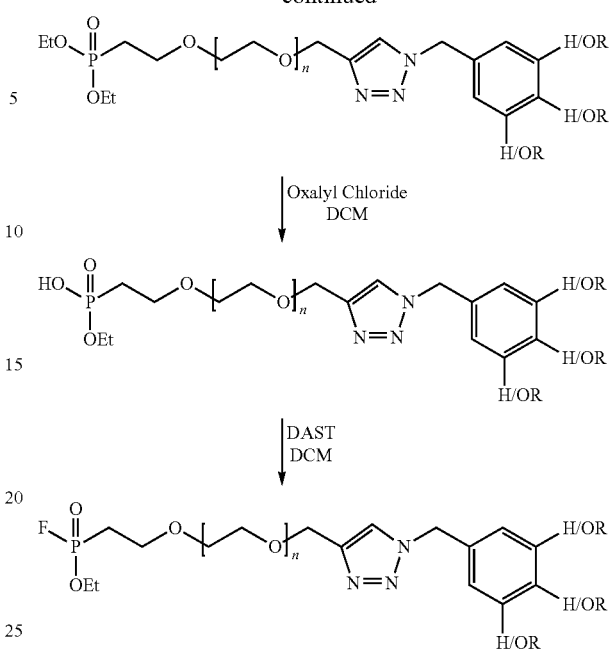

n = 1, 3, 7, 11, 15
R = $C_6H_{13}$, $C_{12}H_{25}$, $C_{18}H_{37}$

D. Synthesis of Hydrophobin Mimics

Accordingly, preweighed protein maintained at 100 μm concentration is reacted with the amphiphilic activity based probe's (AABPs) of step (i) solubilized in 2% TritonX-100 at pH 7.4 using 50 mM sodium phosphate buffer on a rotospin at a speed of about 10-20 rpm at ambient temperature. When the conjugate intensity remains same (typically within 24 hours), the reaction mixture is directly triton removed using ion exchange chromatography (IEX) without any further work-up. The process is depicted in Scheme 4, where PROT represents a protein moiety.

Scheme 4

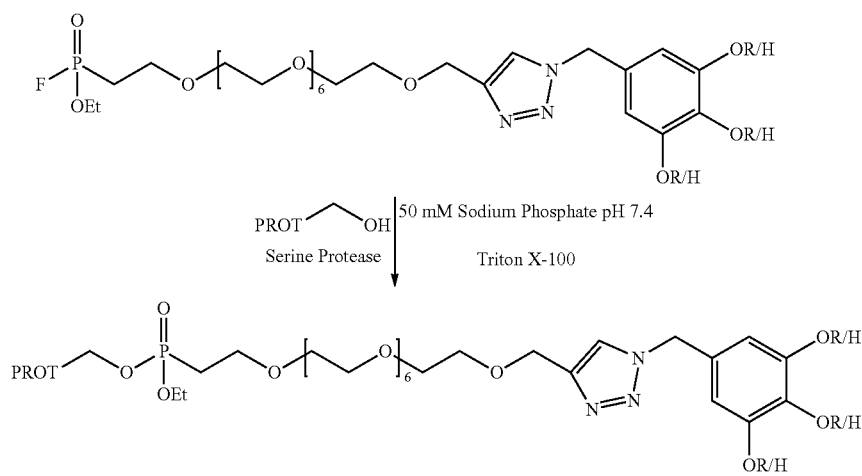

Serine Protease-OEG-1/2/3 tail Hydrophobin Mimic

R = $C_6H_{13}$, $C_{12}H_{25}$, $C_{18}H_{37}$

The monitoring of the extent of conjugation is done by removing aliquots, using the procedure mentioned for monitoring native proteins using MALDI-TOF.

Figure 13:
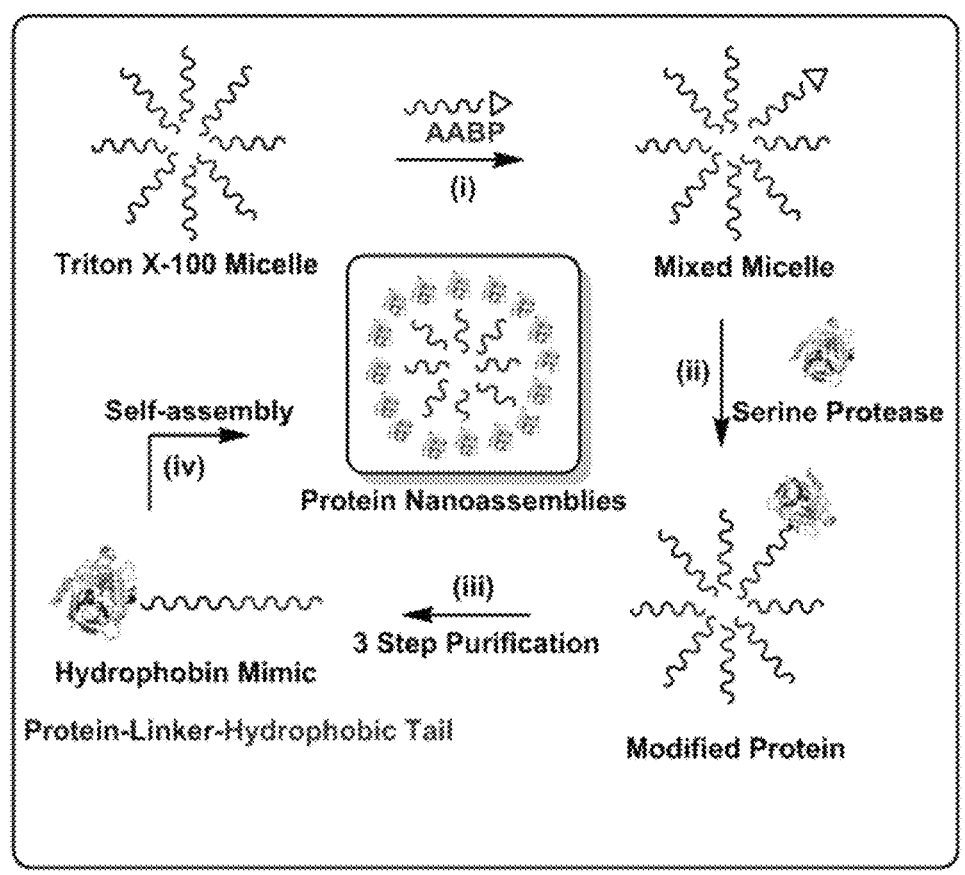
FIG. 13 is the Schematic representation of process for synthesizing hydrophobin mimic of formula (I).

As shown in FIG. 13, Triton X-100 micelles are mixed with AABPs to form mixed micelles (step (i)). The mixed micelles are reacted with a globular protein, shown as a serine protease in FIG. 13 (step (ii)), produced mixed micelles containing modified protein.

In a preferred embodiment, triton X-100 is used to solubilize the azido amphiphilic activity based probe (AABP) for conjugation. The triton X-100 is also used to prevent the aggregation of protein conjugates which is essential during analysis on the MALDI-ToF plate.

The protein for conjugation with amphiphilic activity based probe (AABP) is selected from the class of serine proteases, cysteine proteases, aspartic proteases, metalloproteases such as trypsin, chymotrypsin, subtilisin, proteinase K and the like with a length of up to 500 amino acids.

In yet another embodiment, the purification comprises of two stages; (i) removal of Triton-X-100 and (ii) removal of the unreacted native protein from the conjugate based on the fact that the conjugate molecules are capable of self-assembling either alone or in high salt concentrations using size exclusion chromatography (SEC). Further, the salt content from the conjugate is removed using dialysis method or using desalting column. The salt free samples are quickly lyophilised and the self assembly studies are performed in appropriate buffers. This purification step converts mixed micelles containing a modified hydrophobin mimic protein into a purified hydrophobin mimic protein (FIG. 13, step (iii)). The purified hydrophobin mimics may then undergo self-assembly to form protein nanoassemblies or protein nano containers, for use in bio-nano technology applications (FIG. 13, step (iv)).

Accordingly, ion exchange chromatography (IEX) is performed using either SP sepharose or Q sepharose resins depending on isoelectric point (PI) and surface charges of proteins. SP sepharose is a cation exchange resin and is used to purify the reaction mixture of trypsin or chymotrypsin. The column was pre-equilibrated using same buffer (50 mM sodium phosphate pH 7.4) which was used for modification and then sample was injected followed by post injection equilibration for at least 2 Column Volumes (CVs) or until the complete removal of triton X-100 for large scale reactions. The elution of the protein and its corresponding hydrophobin mimic together as mixture is later achieved using 50 mM sodium phosphate pH 7.4, 1 M NaCl as elution buffer. Monitoring of the fractions is done using MALDI-TOF analysis.

In the second stage, size exclusion chromatography (SEC) is performed for removal of native protein. Accordingly, the obtained IEX fractions are lyophilized quickly and then redissolved in minimum quantity of 50 mM sodium phosphate pH 7.4, 1 M NaCl just before performing SEC. Alternately the obtained fractions are used directly for SEC. The removal of native protein from the hydrophobin mimic is achieved based on the fact that hydrophobin mimics are capable of self-assembling either alone or in high salt concentrations. For the separation of native protein from hydrophobin mimic, 50 mM sodium phosphate pH 7.4, 1 M NaCl is used as solvent. Sephacryl-100 HR 16/60 is used to separate the hydrophobin mimic from native proteins. The SEC column is equilibrated with 50 mM sodium phosphate pH 7.4, 1 M NaCl followed by injection of the sample which is free of triton X-100 and then eluted using same 50 mM sodium phosphate pH 7.4, 1 M NaCl resulting in separation of hydrophobin mimic (eluted first) from unreacted native.

In an embodiment, the size of the assembled protein particle is in the range of 8-100 nm.

In another embodiment, the present invention provides a composition comprising hydrophobin mimics of formula (I) with the particle size in the range of 1-10 nm along with at least one component selected from a surfactant; an acid; a base; a buffer system; an inorganic particle; a UV absorber and other acceptable excipients.

The dynamic light scattering (DLS) and size exclusion chromatography (SEC) studies reveal that self-assembly of hydrophobin mimics can be programmed to yield supramolecular protein assemblies with sizes of 1-100 nm having a molecular weight in the range of 276-400 kDa.

In an embodiment, the novel chemical methodology of the present invention allows to incorporate any kind of chemical entity both small and macromolecules to obtain library of protein amphiphiles or hydrophobin mimics of formula (I) with varied industrial application in bio-nano-technology such as in drug delivery which includes small molecules, proteins, peptides, siRNA, mRNA, microRNA and DNA. The protein nano container of the present invention is useful for encapsulating any kind of cargo (drugs or biomacromolecules). Further, the protein nano containers are useful in vaccine development for treatment of variety of infectious diseases. The constructs could be used for diagnostic and theranostics applications using both passive and active targeting mechanism. This can be achieved by encapsulating diagnostic reagents such as near-infrared fluorescent marker, MRI or PET probe inside protein nanocontainer.

Moreover, the hydrophobins of formula (I) prepared by the novel process of the present invention can be used as a spreading agent for treating surfaces particularly in cosmetic or pharmaceutical compositions, as a coating agent, as surfactants, for increasing the wettability of a surface of a substrate such as glass, PTFE, PET, polycarbonate, stainless steel and aluminum, as tags to purify proteins from complex mixtures and as biosensors.

Using the novel chemical methodology of the present invention, it would be possible to provide antibody drug conjugate by providing site specifically label protein thus avoiding complications that arise because of non-specific labeling.

The hydrophobin mimics of the present invention are highly surface active and hence can be used in cosmetic and in food industry as antimicrobial agents.

Further details of the present invention will be apparent from the examples presented below. Examples presented are purely illustrative and are not limited to the particular embodiments illustrated herein but include the permutations, which are obvious as set forth in the description.

Example 1: Synthesis of 1-Tail (1T) Hydrophobic Azides 1.1 Synthesis of 4-Hydroxybenzyl Alcohol To a suspension of 4-hydroxybenzaldehyde in DCM, silica was added, followed by sodium borohydride. The reaction mixture was stirred for five minutes prior to the dropwise addition of methanol after which it was left to stir for a further thirty minutes. The entire reaction mixture was poured onto a short silica pad and was flushed with acetone. Combined organic layer was dried over $Na_2SO_4$ and evaporated under vacuum to get product which was used without further purification.

1.2 Synthesis of 1-Tail Alkyl Alcohol 4-hydroxybenzyl alcohol (1.0 eq), alkyl bromide (1.1 eq), $K_2CO_3$ (1.2 eq), crown ether (0.1 eq) were taken in an oven dried RBF. The flask was then purged with nitrogen and acetone was added under stirring to dissolve the mixture and refluxed for 24 hours. Upon completion, reaction mixture was concentrated and extracted thrice with DCM. Combined organic layer was dried over $Na_2SO_4$ and evaporated under vacuum to get crude product which was purified using silica gel column chromatography using ethyl acetate/hexane.

1.3 Synthesis of 1-Tail Chloride

In an oven dried RBF, the above obtained alcohol (1.0 eq) was dissolved in dichloromethane (DCM) and catalytic amount of DMF was added. Then thionyl chloride ($SOCl_2$) (1.6 eq) was added dropwise and allowed to react under stirring for 30 minutes at RT. DCM and excess $SOCl_2$ were evaporated under vacuum upon completion. The residue was dissolved in diethyl ether ($Et_2O$) and washed thrice with water. The $Et_2O$ layer was then dried over $Na_2SO_4$ and concentrated under vacuum. The resulting crude product was used for next step without any purification.

1.4 Synthesis of 1-Tail Azide

In an oven dried RBF, mixture of above obtained chloride (1.0 eq) and sodium azide ($NaN_3$) (1.5 eq) was taken and DMF was added. The resulting mixture was stirred for 12 hours at RT. Upon completion, water was added to the reaction mixture and extracted thrice with DCM. Combined organic layer was dried over $Na_2SO_4$ and concentrated under vacuum to get crude product which was purified using silica gel column chromatography using ethyl acetate/hexane.

Example 2: General Procedures for Synthesis of 2-Tail (2T) Hydrophobic Azides

2.1 Synthesis of Ethyl 3, 5-Dihydroxybenzoate 3,5-dihydroxybenzoic acid (35 g, 227 mmol) was taken in an oven dried RBF, ethyl alcohol (250 mL) was added and dissolved with stirring, sulphuric acid (24 mL) was added drop wise and refluxed for 22 hours. Upon completion, reaction mixture was neutralized with aqueous $NaHCO_3$ and extracted thrice with ethyl acetate. The combined organic layer was washed with brine, dried over sodium sulphate ($Na_2SO_4$) and concentrated under vacuum to get crude product, which was further purified using silica gel column chromatography using ethyl acetate/hexane (30:70) to get white colour solid (41 g, 214 mmol, 94%).

2.2 Synthesis of 2-Tail Alkyl Esters

Ethyl 3,5-dihydroxy benzoate (1.0 eq), alkyl bromide (2.5 eq), $K_2CO_3$ (3.5 eq), KI (0.05 eq) were taken in an oven dried RBF. The flask was then purged with nitrogen; DMF was added under stirring to dissolve the mixture and refluxed for 12 hours. Upon completion, reaction mixture was neutralized with acidic water and extracted thrice with ethyl acetate. Combined organic layer was dried over $Na_2SO_4$, and evaporated in vacuum to get crude product which was purified using silica gel column chromatography using ethyl acetate/hexane.

2.3 Synthesis of 2-Tail Alcohol

In an oven dried RBF, above ester (1.0 eq) was taken and dissolved in tetrahydrofuran (THF) with stirring at 0° C. Lithium aluminium hydride (LAH) (3 eq) was added in portions, maintaining reaction temperature at 0° C. After 30 minutes, stirring continued at room temperature (RT) for 12 hours. Upon completion, LAH was quenched by drop wise addition of ethyl acetate at 0° C. (transesterification was observed if the temperature was not maintained at 0° C.). Water was added to reaction mixture and stirred until colour changed to half white. Resulting solution was filtered using Buchner funnel and the residue was washed twice with ethyl acetate. The ethyl acetate layer was separated from water using separating funnel. The residual water layer was again extracted thrice with ethyl acetate. Combined organic layer was dried over $Na_2SO_4$ and concentrated under vacuum to get crude product which was purified using silica gel column chromatography using ethyl acetate/hexane.

2.4 Synthesis of 2-Tail Bromide

Alcohol (1.0 eq) obtained in example (2.3) and triphenylphosphine ($PPh_3$) (2.0 eq) were taken in an oven dried RBF and dissolved in THF. To this solution, tetrabromomethane ($CBr_4$) (2.0 eq) in THF was added dropwise and stirred for 1 hour. Upon completion of reaction, THF was evaporated under vacuum. Water was added to the residue and extracted thrice with ethyl acetate. Combined organic layer was dried over $Na_2SO_4$ and concentrated under vacuum to get crude product, which was purified using silica gel column chromatography using ethyl acetate/hexane.

2.5 Synthesis of 2-Tail Azide

To the mixture of bromide of step (2.4) (1.0 eq) and sodium azide (1.5 eq) in an oven dried RBF, DMF was added and stirred for 12 hours at RT. Upon completion, water was added to the reaction mixture and extracted with ethyl acetate thrice. Combined organic layer was dried over $Na_2SO_4$ and concentrated under vacuum to get crude product which was purified using silica gel column chromatography using ethyl acetate/hexane.

Example 3: General Procedure for Synthesis of 3-Tail (3T) Hydrophobic Azides

3.1 Synthesis of Ethyl 3,4,5-Trihydroxybenzoate

To the stirring solution of 3,4,5-trihydroxybenzoic acid (6 g, 38 mmol) in ethyl alcohol (70 mL), sulphuric acid (4 mL) was added drop wise and refluxed for 22 hours. Reaction mixture was neutralized with aqueous $Na_2CO_3$ solution, extracted thrice with ethyl acetate. The combined organic layer was washed with brine and concentrated under vacuum to get crude product which was purified using silica gel column chromatography using ethyl acetate/hexane (30:70) to get white colour solid (6.73 g, 36 mmol, 95%).

3.2 Synthesis of 3-Tail Esters

Ethyl 3,4,5-trihydroxybenzoate of step (3.1) (1.0 eq), alkyl bromide (3.5 eq), $K_2CO_3$ (3.5 eq) and KI (0.05 eq) were taken in an oven dried flask. The flask was then purged with nitrogen; DMF was added under stirring to dissolve the mixture and refluxed for 12 hours. Upon completion, reaction mixture was neutralized with acidic water and extracted thrice with ethyl acetate. Combined organic layer was dried over $Na_2SO_4$ and evaporated in vacuum to get crude product which was purified using silica gel column chromatography using ethyl acetate/hexane.

3.3 Synthesis of 3-Tail Alcohol

In an oven dried RBF, above ester (1.0 eq) was dissolved with stirring in THF at 0° C. Then LAH (3 eq) was added in portions maintaining reaction temperature at 0° C. After 30 minutes, stirring was continued at room temperature (RT) for 12 hours. Upon completion, LAH was quenched by drop wise addition of ethyl acetate at 0° C. (transesterification was observed if temperature was not maintained at 0° C.). Water was added to reaction mixture and stirred until colour changes to half white. Resulting solution was filtered through Buchner funnel and residue was washed twice with ethyl acetate. Ethyl acetate layer was separated from water using separating funnel. The residual water layer was extracted thrice with ethyl acetate. The combined organic layer was dried over $Na_2SO_4$ and concentrated under vacuum to get crude product which was purified using silica gel column chromatography using ethyl acetate/hexane.

3.4 Synthesis of 3-Tail Chloride Derivative

In an oven dried RBF, the above obtained alcohol (1.0 eq) was dissolved in dichloromethane (DCM) and catalytic amount of DMF was added. Then thionyl chloride ($SOCl_2$, 1.6 eq) was added drop wise and allowed to react under stirring for 30 minutes. DCM and excess $SOCl_2$ was later evaporated under vacuum. The residue was dissolved in diethyl ether ($Et_2O$) and washed thrice with water. The separated $Et_2O$ layer was dried over $Na_2SO_4$ and concentrated under vacuum to get crude product which was taken for next step without purification.

3.5 Synthesis of 3-Tail Azide

The crude mixture of chloride (1.0 eq) obtained in step (4.4) in an oven dried RBF was dissolved in DMF and sodium azide (1.5 eq) was added and stirred for 12 hours at RT. Upon completion, water was added to quench the reaction and extracted thrice with ethyl acetate. The combined organic layers was dried over $Na_2SO_4$ and concentrated under vacuum to get crude product which was purified using silica gel column chromatography using ethyl acetate/hexane.

Example 4: Synthesis of Hydrophilic Spacers

4.1. Synthesis of Di and Tetra Ethylene Glycol Spacers 4.1.1 General Procedure for Synthesis of Monopropargylate In an oven dried RBF, di or tetra ethylene glycol (DEG or TEG) (1.0 eq) was dissolved with stirring in THF. Sodium hydride (NaH) (1.0 eq) was added to the flask in small portions at 0° C. After 1 hour, propargyl bromide (0.7 eq) was added dropwise, maintaining the reaction at the same temperature. Then reaction was stirred for 12 hours at RT. Upon completion, excess NaH was quenched with dropwise addition of water. Resulting reaction mixture was extracted in DCM thrice. Combined organic layer was dried over $Na_2SO_4$ and concentrated under vacuum to get crude product, which was purified using silica gel column chromatography using MeOH/DCM as eluent.

4.1.2 General Procedure for Synthesis of Tosylate

In an oven dried RBF, monopropargylate (1.0 eq) was dissolved with stirring in THF at 0° C. Aqueous KOH (4 eq) was added to the flask in small portions immediately. After 10 minutes, tosyl chloride (1.2 eq) solution in THF was added dropwise and stirred for 12 hours. Upon completion, reaction was quenched with aqueous ammonium chloride and extracted with DCM thrice to get crude product which was purified using silica gel column chromatography using MeOH/DCM as eluent.

4.1.3 General Procedure for Synthesis of Iodide

A mixture of above obtained tosylate (1.0 eq) and KI (4.0 eq) was refluxed in acetone for 18 hours. Upon completion, excess KI was filtered and washed thrice with acetone. Collected acetone fraction was evaporated under vacuum to get residue, which was then washed with water and extracted with DCM. The combined organic layer was washed with aqueous $Na_2CO_3$ and then concentrated under vacuum to get crude product which was purified using silica gel column chromatography using MeOH/DCM as eluent.

4.1.4 General Procedure for Synthesis of Diphosphonate Ester

In an oven dried RBF, iodide (1.0 eq) and triethyl phosphite, $P(OEt)_3$ (4.0 eq) were taken and refluxed for 1 hour at 150° C. Upon completion of reaction, the excess $P(OEt)_3$ was removed under vacuum and the reaction mixture was directly loaded onto a silica gel column and crude mixture was purified using MeOH/DCM as eluent.

Example 4.2. Synthesis of Octa, Dodeca and Cetyl Ethylene Glycol Spacers 4.2.1 Synthesis of Monopropargylate In an oven dried RBF, a mixture of TEG (1.0 eq) and TsO-(OEG)$_n$ propargylate (0.5 eq) was taken and dissolved in THF under stirring. Reaction mixture was cooled to 0° C. and NaH (1.0 eq) was added in a small portions. Resultant mixture was stirred at RT for 12 hours. Upon completion of reaction, excess of NaH was quenched by dropwise addition of water. Resultant mixture was concentrated under reduced pressure. To the obtained residue, water was added and washed with ethyl acetate thoroughly (at least for eight times). Now aqueous layer was concentrated under reduced pressure and to the obtained residue, fresh ethyl acetate was added and filtered to remove salts. Finally, the resulting ethyl acetate layer was dried over $Na_2SO_4$ and concentrated under reduced pressure to get product HO-(OEG)$_{n+4}$ along with TEG contamination. This crude product was taken to the next step without purification.

4.2.2 Synthesis of Tosylate

In an oven dried RBF, the crude product HO-(OEG)$_{n+4}$ propargylate with TEG (1.0 eq), DMAP (0.5 eq) and tosyl chloride (15 eq) was taken and dissolved in DCM under stirring. Mixture was cooled to 0° C. and triethyl amine (20 eq) was added drop wise. The resultant mixture was then stirred for 12 hours at RT. Upon completion, reaction was quenched by dropwise addition of water and extracted with DCM for thrice. Combined organic layer was dried over $Na_2SO_4$ and concentrated under reduced pressure to get a crude product, TsO-(OEG)$_{n+4}$ which was purified using silica gel column chromatography.

Procedure for synthesis of iodides and diphosphonate esters remained same as procedure described in example (IV-A-iii) and example (IV-A-iv). The TsO-(OEG)$_{n+4}$ on reflux in acetone in presence of KI afforded corresponding iodo derivative. Diphosphonate ester was synthesized later by refluxing iodo compound with triethyl phosphite.

Example 5: Synthesis of 1/2/3-Tail Amphiphilic Activity Based Probes (AABPs)

All the AABPs were synthesised by [2+3] dipolar cycloaddition (click reaction) of the hydrophilic alkynes (diphosphonate esters) with hydrophobic azides in the presence of sodium ascorbate and copper sulphate ($CuSO_4$) in THF/water (1:1) unless mentioned. Then the resulting product was deprotected in the presence of oxalyl chloride in DCM to get monophosphonate ester and finally fluorinated using diethylaminosulfur triflouride (DAST) in DCM. The detailed procedure is mentioned below.

5.1 General Procedure for Click Reaction

Hydrophobic azide (1 eq) and hydrophilic alkyne (1 eq) were dissolved in degassed THF and stirred until clear solution was obtained, then degassed water was added and stirred vigorously for 10 more minutes. Freshly prepared 1M sodium ascorbate (0.05 eq) and 1M $CuSO_4$ (0.1 eq) were added to the reaction mixture at least thrice in an intervals of 45 minutes and allowed to react for 16 hours at RT. Upon completion, reaction mixture was extracted in DCM and combined organic layer was dried over $Na_2SO_4$ and concentrated under reduced pressure to get crude product which was purified using reverse phase chromatography using $ACN/H_2O$ system first (to remove unreacted diphosphonate ester) and $CHCl_3$ later (to elute click product) followed by normal phase chromatography using MeOH/DCM solvent system.

5.2. Deprotection of Diphosphonate Ester

Diphosphonate ester (1 eq) was dissolved in DCM with stirring. Then oxalyl chloride (4 eq) was added dropwise at RT and allowed to react for 18 hours under stirring. Upon completion, excess of oxalyl chloride and DCM were removed under vacuum. Then water was added to the residue and stirred for 5 minutes. The resulting mixture was extracted thrice with DCM, combined organic layer was dried over $Na_2SO_4$ and concentrated under vacuum to get crude product which was used for next step without further purification.

5.3 Fluorination of Monophosphonate Ester

To the stirring solution of monophosphonate ester (1 eq) in DCM, DAST (4 eq) was added dropwise at RT and allowed to react for 4 hours. Excess of DAST and DCM were evaporated under reduced pressure. To the obtained residue, water was added and stirred for 2 more minutes to quench any residual DAST. Reaction mixture was then extracted thrice with DCM. Combined organic layer was dried over $Na_2SO_4$ and concentrated under vacuum to get crude product. These final AABPs were used for protein modification without further purification.

Example 6: Synthetic Procedure for Individual Hydrophobic Azides and their Intermediates (i) Synthesis of Compound 1

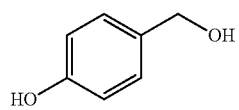

1

The compound 1 was prepared by general procedure of example 1.1, starting from 4-hydroxybenzaldehyde (1.5 g, 12.3 mmol), silica (2.5 g), sodium borohydride (0.475 g, 12.5 mmol), in DCM. The product was obtained as a white solid (1.4 g, 3.1 mmol, 90%), which was used for modification without purification, $R_f$=0.25 in 75% ethyl acetate/hexane. $^1$H NMR (400 MHz, MeOD): $\delta_H$ 7.19 (d, J=8.4 Hz, 2H), 6.77 (d, J=8.4 Hz, 2H), 4.50 (s, 2H).

Mol. formula: $C_7H_8O_2$
Mol. Weight: 124.05
Physical appearance: White solid
Yield: 90%

(ii) Synthesis of Compound 1a

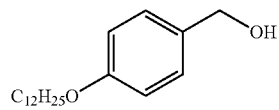

1a

The compound 1a was prepared by general procedure of example 1.2, starting from compound 1 (0.52 g, 4.2 mmol), 1-bromododecane (1.1 g, 4.4 mmol), $K_2CO_3$ (0.84 g, 5.1 mmol), 18-crown-6 (0.10 g, 0.4 mmol) in acetone. The product was obtained as a white solid (0.90 g, 3.1 mmol, 73%) after purification by silica gel column chromatography using ethyl acetate/hexane as eluent, $R_f$=0.25 in 75% ethyl acetate/hexane. $^1$H NMR (400 MHz, $CDCl_3$): $\delta_H$ 7.23 (d, J=8.8 Hz, 2H), 6.87 (d, J=8.8 Hz, 2H), 4.56 (s, 2H), 3.93 (t, J=6.8 Hz, 2H), 1.80-1.73 (m, 2H), 1.47-1.26 (m, 18H), 0.88 (t, J=7.2 Hz, 3H). $^{13}$C NMR (100 MHz, $CDCl_3$): $\delta_C$. 158.93, 133.03, 128.75, 114.70, 77.16, 68.22, 65.23, 32.06, 29.80, 29.78, 29.74, 29.72, 29.54, 29.49, 29.40, 26.18, 22.83, 14.26. MALDI-TOF MS (M+K): 331.22.

Mol. formula: $C_{19}H_{32}O_2$
Mol. Weight: 292.24
Physical appearance: White solid
Yield: 73%

(iii) Synthesis of 1b

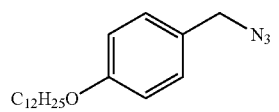

1b

The compound 1b was prepared by general procedure of examples (1.3 and 1.4) from 1a (0.50 g, 1.7 mmol). Synthesis of chloride was achieved using $SOCl_2$ (0.32 g, 2.7 mmol) and catalytic amount of DMF in DCM; subsequently azide was synthesized using $NaN_3$ (0.16 g, 2.5 mmol) in DMF. The product was obtained as a white solid (0.32 g, 1.0 mmol, 60%) after purification by silica gel column chromatography using ethyl acetate/hexane as eluent, $R_f$=0.44 in 5% ethyl acetate/hexane. $^1$H NMR (400 MHz, $CDCl_3$): $\delta_H$ 7.22 (d, J=8.8 Hz, 2H), 6.88 (d, J=8.8 Hz, 2H), 4.25 (s, 2H), 3.93 (t, J=6.8 Hz, 2H), 1.80-1.73 (m, 2H), 1.51-1.30 (m, 18H), 0.90 (t, J=7.2 Hz, 3H). $^{13}$C NMR (100 MHz, $CDCl_3$): $\delta_C$. 159.28, 129.70, 127.20, 114.75, 77.16, 68.04, 54.44, 32.02, 29.77, 29.74, 29.71, 29.68, 29.50, 29.45, 29.34, 26.13, 22.78, 14.17. MALDI-TOF MS (M+K): 356.22. Mol. formula: $C_{19}H_{31}O$ Mol. Weight: 317.26
Physical appearance: White solid
Yield: 60%

(iv) Synthesis of Compound 2a

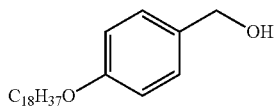

2a

The compound 2a was prepared by general procedure of example 1.2, starting from compound 1 (0.52 g, 4.2 mmol), 1-bromooctadecane (1.5 g, 4.6 mmol), $K_2CO_3$ (0.84 g, 5.1 mmol), 18-crown-6 (0.10 g, 0.4 mmol) in acetone. The product was obtained as a white solid (1.0 g, 2.8 mmol, 68%) after purification by silica gel column chromatography using DCM/hexane as eluent, $R_f$=0.25 in 10% ethyl acetate/hexane. $^1$H NMR (400 MHz, $CDCl_3$): $\delta_H$ 7.29 (d, J=8.8 Hz, 2H), 6.90 (d, J=8.8 Hz, 2H), 4.62 (s, 2H), 3.97 (t, J=6.8 Hz, 2H), 1.88-1.70 (m, 2H), 1.51-1.21 (m, 34H), 0.91 (t, J=7.2 Hz, 3H)$^{13}$C NMR (100 MHz, $CDCl_3$): $\delta_C$. 158.95, 133.04, 128.76, 114.71, 77.16, 68.22, 65.25, 32.08, 29.85, 29.81, 29.76, 29.73, 29.56, 29.51, 29.42, 26.19, 22.84, 14.27. MALDI-TOF MS (M+K): 415.31

Mol. formula: $C_{25}H_{44}O_2$
Mol. Weight: 376.33
Physical appearance: White solid
Yield: 68%

(v) Synthesis of 2b

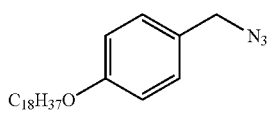

2b

The compound 2b was prepared by general procedure of examples (1.3 and 1.4) from 2a (0.30 g, 0.9 mmol). Synthesis of chloride was achieved using $SOCl_2$ (0.17 g, 1.5 mmol) and catalytic amount of DMF in DCM; subsequently azide was synthesized using $NaN_3$ (0.09 g, 1.4 mmol) and TBAB (0.3 g, 0.9 mmol) in THF. The product was obtained as white solid (0.27 g, 0.6 mmol, 72%) after purification by silica gel column chromatography using ethyl acetate/hexane as eluent, $R_f$=0.44 in 5% ethyl acetate/hexane. $^1$H NMR (400 MHz, $CDCl_3$): $\delta_H$. 7.25 (d, J=8.8 Hz, 2H), 6.92 (d, J=8.8 Hz, 2H), 4.29 (s, 2H), 3.99 (t, J=6.8 Hz, 2H), 1.87-1.74 (m, 2H), 1.53-1.25 (m, 32H), 0.92 (t, J=7.2 Hz, 3H) $^{13}$C NMR (100 MHz, $CDCl_3$): $\delta_C$. 159.35, 129.81, 127.26, 114.86, 77.16, 68.18, 54.56, 32.07, 29.85, 29.81, 29.75, 29.73, 29.54, 29.51, 29.39, 26.18, 22.84, 14.25. MALDI-TOF MS (M+Na): 424.35.

Mol. formula: $C_{25}H_{43}N_3O$
Mol. Weight calculated: 401.34.
Physical appearance: White solid
Yield: 72% v. Synthesis of 3a

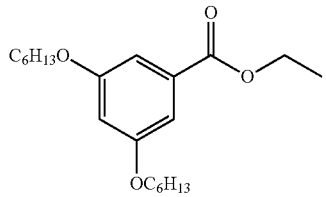

3a

The compound 3a was prepared by general procedure of example 2.2 starting from ethyl 3,5-dihydroxybenzoate (5 g, 27 mmol), 1-hexyl bromide (11.5 g, 82 mmol), $K_2CO_3$ (11.5 g, 69 mmol), KI (0.22 g, 1.3 mmol), in DMF. The product was obtained as a colourless liquid (9 g, 26 mmol, 95%) after silica gel column chromatography using ethyl acetate/hexane as eluent.

$R_f$=0.46, solvent=5% ethyl acetate/hexane $^1$H NMR (400 MHz, $CDCl_3$) $\delta_H$7.16 (d, J=2.4 Hz, 2H), 6.63 (t, J=2.4 Hz, 1H), 4.34 (q, J=7.2 Hz, 2H), 3.97 (t, J=6.8 Hz, 4H), 1.77 (quint, J=6.8 Hz, 4H), 1.49-1.31 (m, 15H), 0.90 (t, J=6.8 Hz, 6H)

$^{13}$C NMR (100 MHz, $CDCl_3$) $\delta_C$166.67, 160.25, 132.32, 107.74, 106.41, 68.43, 61.21, 31.70, 29.29, 25.83, 22.74, 14.47, 14.18

MALDI-ToF: (M+K) 389.20

Mol. formula: $C_{21}H_{34}O_4$

Mol. weight: 350.25

Physical appearance: colourless liquid

Yield: 96% vi. Synthesis of 3b

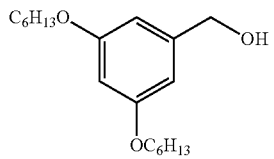

3b

The compound 3b was synthesized using general procedure of example 2.3 starting from 3a (9.2 g, 26 mmol), LAH (2.9 g, 78 mmol) in THF. The product was obtained as a colourless liquid (6 g, 18 mmol, 70%) after silica gel column chromatography using ethyl acetate/hexane as eluent.

$R_f$=0.32 in 10% ethyl acetate/hexane $^1$H NMR (400 MHz, $CDCl_3$) $\delta_H$6.49 (d, J=2.4 Hz, 2H), 6.38 (t, J=2.4 Hz, 1H), 4.61 (s, 2H), 3.93 (t, J=6.8 Hz, 4H), 1.76 (quint, J=6.4 Hz, 4H), 1.48-1.39 (m, 4H), 1.37-1.30 (m, 8H), 0.91 (t, J=6.8 Hz, 6H)

Mol. formula: $C_{19}H_{32}O_3$

Mol. Weight: 307.24

Physical appearance: colourless liquid

Yield: 70% vii. Synthesis of 3c

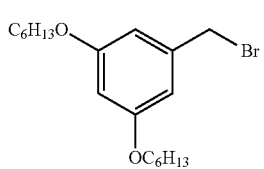
3c

The compound 3c was synthesized using general procedure of example 2.4 starting from 3b (2 g, 6.4 mmol), PPh₃ (1.7 g, 6.4 mmol) and CBr₄ (12.2 g, 6.4 mmol) in THF. The product was obtained as a colourless liquid (1.8 g, 4.8 mmol, 75%) after silica gel column chromatography using ethyl acetate/hexane as eluent.

$R_f$=0.49, solvent=5% ethyl acetate/hexane $^1$H NMR (400 MHz, CDCl₃) $\delta_H$ 6.5 (d, J=2 Hz, 2H), 6.38 (t, J=2 Hz, 1H), 4.41 (s, 2H), 3.92 (t, J=6.8 Hz, 4H), 1.76 (qunit, J=6.4 Hz, 4H), 1.48-1.39 (m, 4H), 1.37-1.30 (m, 8H), 0.91 (t, J=6.8 Hz, 6H)

$^{13}$C NMR (100 MHz, CDCl₃) $\delta_C$ 160.51, 139.64, 107.40, 101.50, 68.21, 33.95, 31.70, 29.31, 25.84, 22.74, 14.18

MALDI-ToF (M+Na): 393.11

Mol. formula: $C_{19}H_{31}BrO_2$

Mol. Weight: 370.56

Physical appearance: colourless liquid

Yield: 75% viii. Synthesis of 3d

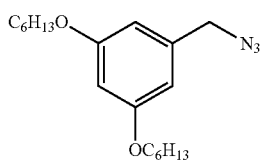
3d

The compound 3d was synthesized from general procedure of example 2.5, starting from 3c (1.5 g, 4 mmol), NaN₃ (0.26 g, 4 mmol) in DMF. The product was obtained as a yellowish liquid (1 g, 3 mmol, 75%) after silica gel column chromatography using ethyl acetate/hexane as eluent.

$R_f$=0.48, solvent=5% ethyl acetate/hexane.

$^1$H NMR (400 MHz, CDCl₃) $\delta_H$ 6.44 (d, J=2.4 Hz, 2H), 6.41 (t, J=2.4 Hz, 1H), 4.24 (s, 2H), 3.93 (t, J=6.8 Hz, 4H), 1.77 (quint, J=6.8 Hz, 4H), 1.48-1.39 (m, 4H), 1.37-1.30 (m, 8H), 0.91 (t, J=6.8 Hz, 6H)

$^{13}$C NMR (100 MHz, CDCl₃) $\delta_C$ 160.72, 137.51, 106.40, 101.50, 68.21, 55.05, 31.70, 29.31, 25.84, 22.74, 14.18

MALDI-ToF (M+K) 372.25

Mol. formula: $C_{19}H_{31}N_3O_2$

Mol. Weight: 333.47

Physical appearance: yellowish liquid

Yield: 75% ix. Synthesis of 4a

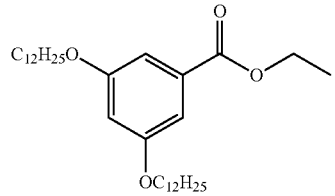
4a

The compound 4a was prepared by general procedure of example 2.2, starting from ethyl 3,5-dihydroxybenzoate (4 g, 21 mmol), dodecyl bromide (13.41 g, 53 mmol), K₂CO₃ (12.1 g, 87 mmol), KI (0.2 g, 2.7 mmol), in acetonitrile (ACN)/THF (2:1). The product was obtained as a white solid (9.08 g, 17 mmol, 79%) after silica gel column chromatography using ethyl acetate/hexane as eluent, $R_f$=0.48, solvent 5% ethyl acetate/hexane.

$^1$H NMR (400 MHz, CDCl₃) $\delta_H$ 7.1 (d, J=2 Hz, 2H), 6.6 (t, J=2 Hz, 1H), 4.36 (q, J=6.8 Hz 2H), 3.96 (t, J=6.8 Hz, 4H), 1.77 (quint, J=6.8 Hz, 4H), 1.48-1.20 (m, 41H), 0.88 (t, J=7.2 Hz, 6H)

$^{13}$C NMR (100 MHz, CDCl₃) $\delta_C$ 166.67, 160.24, 132.31, 107.73, 106.39, 68.43, 61.21, 32.07, 29.81, 29.79, 29.75, 29.73, 29.59, 29.51, 29.33, 26.16, 22.84, 14.47, 14.28

HRMS (M+H) 519.44

Mol. formula: $C_{33}H_{58}O_4$

Mol. Weight: 518.43

Physical appearance: White solid

Yield: 78% x. Synthesis of 4b

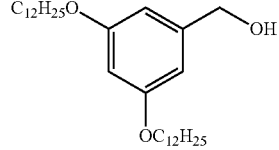
4b

The compound 4b was synthesized from general procedure of example 2.3, starting from 4a (5 g, 9.6 mmol), LAH (1.25 g, 32 mmol), in THF. The product was obtained as a white solid (3.7 g, 7.7 mmol, 86%) after silica gel column chromatography using ethyl acetate/hexane as eluent.

$R_f$=0.32, solvent=10% ethyl acetate/hexane.

$^1$H NMR (400 MHz, CDCl₃) $\delta_H$ 6.4 (d, J=2 Hz, 2H), 6.37 (t, J=2 Hz, 1H), 4.61 (s, 2H), 3.93 (t, J=6.8 Hz, 4H), 1.76 (quint, J=6.4 Hz, 4H), 1.47-1.20 (m, 36H), 0.88 (t, J=7.2 Hz, 6H)

$^{13}$C NMR (100 MHz, CDCl₃) $\delta_C$ 160.65, 143.30, 105.14, 100.63, 68.18, 65.61, 32.06, 29.81, 29.78, 29.75, 29.73, 29.53, 29.50, 29.39, 26.18, 22.84, 14.28

HRMS (M+H) 477.43

Mol. formula: $C_{31}H_{56}O_3$

Mol. Weight: 476.42

Physical appearance: White solid

Yield: 86% xi. Synthesis of 4c

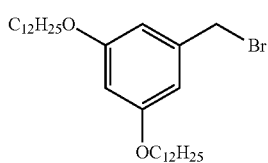
4c

The compound 4c was synthesized from general procedure of example 2.4 starting from 4b (3.5 g, 7.3 mmol), PPh$_3$ (3.3 g, 14 mmol) and CBr$_4$ (4.9 g, 14 mmol) in THF. The product was obtained as a white solid (3.3 g, 6 mmol, 85%) after silica gel column chromatography using ethyl acetate/hexane as eluent.

$R_f$=0.49, solvent=5% ethyl acetate/hexane.

$^1$H NMR (400 MHz, CDCl$_3$) $\delta_H$6.51 (d, J=2.4 Hz, 2H), 6.38 (t, J=2.4 Hz, 1H), 4.40 (s, 2H), 3.92 (t, J=6.8 Hz, 4H), 1.76 (quint, J=6.8 Hz, 4H), 1.47-1.20 (m, 37H), 0.88 (t, J=7.2 Hz, 6H)

$^{13}$C NMR (100 MHz, CDCl$_3$) $\delta_C$160.53, 139.64, 107.48, 101.51, 68.23, 33.96, 32.06, 29.81, 29.78, 29.75, 29.73, 29.53, 29.50, 29.39, 26.18, 22.84, 14.28

HRMS (M+H) 539.34

Mol. formula: $C_{31}H_{55}BrO_2$

Mol. Weight: 538.33

Physical appearance: White solid

Yield: 85% xii. Synthesis of 4d

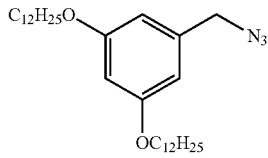
4d

The compound 4d was synthesized from general procedure of example 2.5 starting from bromide 4c (1.2 g, 2.2 mmol), NaN$_3$ (0.217 g, 4.1 mmol) in DMF. The product was obtained as a white solid (0.95 g, 1.9 mmol, 86%) after silica gel column chromatography using ethyl acetate/hexane as eluent.

$R_f$=0.48, solvent=5% ethyl acetate/hexane.

$^1$H NMR (400 MHz, CDCl$_3$) $\delta_H$6.43 (d, J=2 Hz, 2H), 6.41 (t, J=2 Hz, 1H), 4.25 (s, 2H), 3.93 (t, J=6.8 Hz, 4H), 1.76 (quint, J=7.2 Hz, 4H), 1.47-1.20 (m, 36H), 0.88 (t, J=7.2 Hz, 6H)

$^{13}$C NMR (100 MHz, CDCl$_3$) $\delta_C$160.73, 137.50, 106.56, 101.13, 68.24, 55.07, 32.06, 29.81, 29.78, 29.75, 29.73, 29.53, 29.50, 29.39, 26.18, 22.84, 14.28

HRMS (M+H) 502.43

Mol. formula: $C_{31}H_{55}N_3O_2$

Mol. Weight: 501.80

Physical appearance: White solid

Yield: 86% xiii. Synthesis of 5a

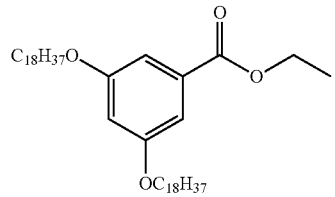
5a

The compound 5a was prepared by General procedure of example 2.2 starting from ethyl 3,5-dihydroxybenzoate (1 g, 5.4 mmol), octadecyl bromide (5.5 g, 16 mmol), K$_2$CO$_3$ (3.8 g, 27 mmol), KI (0.045 g, 0.27 mmol), in DMF. The product was obtained as a white solid (3.4 g, 4.9 mmol, 91%) after silica gel column chromatography using ethyl acetate/hexane as eluent.

$R_f$=0.46, solvent=5% ethyl acetate/hexane.

$^1$H NMR (400 MHz, CDCl$_3$) $\delta_H$7.15 (s, 2H), 6.66 (s, 1H), 4.32 (q, J=6.8 Hz 2H), 3.96 (t, J=7.2 Hz, 4H), 1.77 (quint, J=6.8 Hz, 4H), 1.48-1.20 (m, 67H), 0.88 (t, J=7.2 Hz, 6H)

$^{13}$C NMR (100 MHz, CDCl$_3$) $\delta_C$166.67, 160.28, 132.36, 107.81, 106.48, 68.48, 61.20, 32.08, 29.85, 29.81, 29.76, 29.73, 29.64, 29.53, 29.51, 29.35, 29.17, 22.84, 14.47, 14.26

HRMS (M+H) 687.62

Mol. formula: $C_{69}H_{115}N_3O_7$

Mol. Weight: 1081.87

Physical appearance: White solid

Yield: 67% xiv. Synthesis of 5b

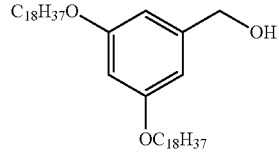
5b

The compound 5b was synthesized from general procedure of example 2.3, starting from 5a (7 g, 10 mmol), LAH (1.3 g, 33 mmol), in THF. The product was obtained as a white solid (7 g, 10 mmol, 96%) after silica gel column chromatography using ethyl acetate/hexane as eluent.

$R_f$=0.32, solvent=10% ethyl acetate/hexane.

Mol. formula: $C_{43}H_{80}O_3$

Mol. Weight: 644.61

Physical appearance: White solid

Yield: 96% xv. Synthesis of 5c

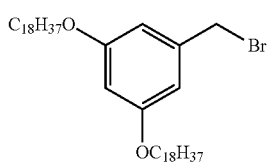

5c

The compound 5c was synthesized from general procedure of example 2.4, starting from 5b (3.0 g, 4.6 mmol), PPh$_3$ (2.4 g, 9.3 mmol) and CBr$_4$ (3.0 g, 9.3 mmol) in THF. The product was obtained as a white solid (2.6 g, 3.6 mmol, 82%) after silica gel column chromatography using ethyl acetate/hexane using eluent.

R$_f$=0.49, solvent=5% ethyl acetate/hexane.

$^1$H NMR (400 MHz, CDCl$_3$) $\delta_H$6.5 (s, 2H), 6.39 (s, 1H), 4.43 (s, 2H), 3.94 (t, J=6.4 Hz, 4H), 1.76 (quint, J=6.4 Hz, 4H), 1.48-1.39 (m, 4H), 1.35-1.20 (m, 60H), 0.91 (t, J=6.8 Hz, 6H)

$^{13}$C NMR (100 MHz, CDCl$_3$) $\delta_C$160.58, 139.71, 107.81, 106.48, 68.48, 61.20, 32.08, 29.85, 29.81, 29.76, 29.73, 29.64, 29.53, 29.51, 29.35, 29.17, 22.84, 14.26

HRMS (M+H) 709.56

Mol. formula: C$_{43}$H$_{79}$BrO$_3$

Mol. Weight: 706.52

Physical appearance: White solid

Yield: 82% xvi. Synthesis of 5d

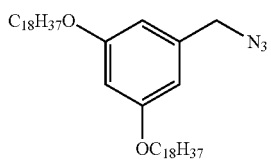

5d

The compound 5d was synthesized from general procedure of example 2.5, starting from 5c (0.3 g, 0.4 mmol), NaN$_3$ (0.11 g, 1.6 mmol) and TBAB (0.100 g, 0.3 mmol) in THF. The product was obtained as a white solid (0.15 g, 0.2 mmol, 79%) after silica gel column chromatography using ethyl acetate/hexane as eluent.

R$_f$=0.48, solvent=5% ethyl acetate/hexane.

$^1$H NMR (400 MHz, CDCl$_3$) $\delta_H$6.43 (d, J=2 Hz, 2H), 6.41 (t, J=2 Hz, 1H), 4.25 (s, 2H), 3.93 (t, J=6.8 Hz, 4H), 1.76 (quint, J=6.8 Hz, 4H), 1.48-1.39 (m, 4H), 1.35-1.20 (m, 60H), 0.87 (t, J=7.2 Hz, 6H)

$^{13}$C NMR (100 MHz, CDCl$_3$) $\delta_C$160.79, 137.59, 107.81, 106.65, 101.26, 68.31, 55.12, 32.09, 29.85, 29.81, 29.76, 29.73, 29.64, 29.53, 29.51, 29.35, 29.17, 26.20, 22.84, 14.26

HRMS (M+Na) 693.28

Mol. formula: C$_{43}$H$_{79}$N$_3$O$_3$

Mol. Weight: 669.61

Physical appearance: White solid

Yield: 79% xvii. Synthesis of 6a

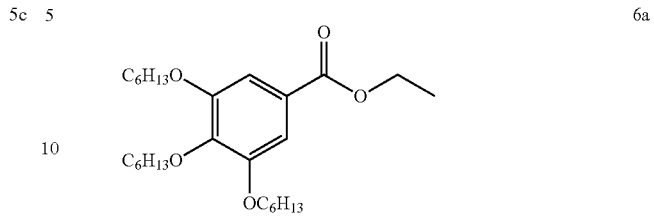

6a

The compound 6a was prepared by general procedure of example 3.2, starting from ethyl 3,4,5-trihydroxybenzoate (5.2 g, 28 mmol), hexyl bromide (20 g, 121 mmol), K$_2$CO$_3$ (11 g, 78 mmol), KI (0.25 g, 1.5 mmol), in DMF. The product was obtained as a white solid (12 g, 26 mmol, 90%) after silica gel column chromatography using ethyl acetate/hexane as eluent.

R$_f$=0.46, solvent=5% ethyl acetate/hexane.

$^1$H NMR (400 MHz, CDCl$_3$) $\delta_H$7.25 (s, 2H), 4.34 (q, J=7.2 Hz 2H), 4.01 (t, J=6.8 Hz, 6H), 1.84-1.70 (m, 6H), 1.50-1.20 (m, 21H), 0.88 (m, 9H)

$^{13}$C NMR (100 MHz, CDCl$_3$) $\delta_C$166.61, 152.89, 142.33, 125.15, 108.0, 73.59, 69.24, 61.10, 31.86, 31.68, 30.38, 29.38, 25.87, 22.75, 29.64, 14.54, 14.16 MALDI-TOF (M+K) 489.24

Mol. formula: C$_{27}$H$_{46}$O$_5$

Mol. Weight: 450.33

Physical appearance: White solid

Yield: 90% xviii. Synthesis of 6b

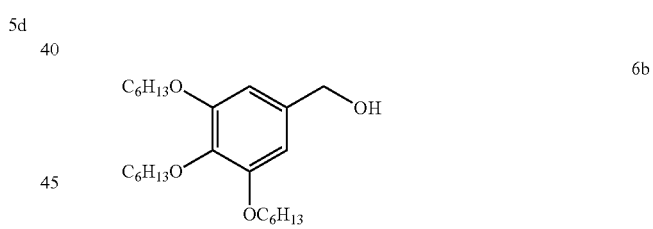

6b

The compound 6b was prepared by general procedure of example 3.3, starting from 6a (1 g, 2.2 mmol), LAH (0.25 g, 6.6 mmol) in THF. The product is obtained as a white solid (0.73 g, 1.8 mmol 82%) after silica gel column chromatography using ethyl acetate/hexane as eluent.

R$_f$=0.25, solvent=10% ethyl acetate/hexane.

$^1$H NMR (400 MHz, CDCl$_3$) $\delta_H$6.55 (s, 2H), 4.5 (s, 2H), 3.95 (m, 6H), 1.82-1.70 (m, 6H), 1.50-1.20 (m, 18H), 0.89 (m, 9H)

$^{13}$C NMR (100 MHz, CDCl$_3$) $\delta_C$153.36, 137.56, 136.18, 105.35, 77.16, 73.55, 69.17, 65.78, 31.91, 31.70, 31.09, 30.39, 29.48, 25.90, 22.77, 14.24

MALDI-TOF (M+K) 447.28

Mol. formula: C$_{25}$H$_{44}$O$_4$

Mol. Weight: 408.32

Physical appearance: White solid

Yield: 82% xix. Synthesis of 6c

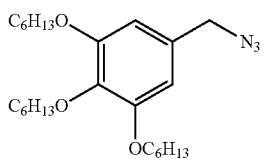

6c

The compound 6c was prepared by general procedure of examples (3.4 and 3.5), starting from 6b (1 g, 2.4 mmol) we generated chloride using $SOCl_2$ (0.45 g, 4 mmol) in DCM and subsequently synthesised azide using sodium azide (0.23 g, 3.5 mmol) in DMF. The product was obtained as pale yellow liquid (1 g, 2 mmol, 96%) after silica gel column chromatography using ethyl acetate/hexane as eluent.

$R_f$=0.44, solvent=5% ethyl acetate/hexane.

$^1$H NMR (400 MHz, $CDCl_3$) $\delta_H$6.48 (s, 2H), 4.24 (s, 2H), 3.96 (m, 6H), 1.83-1.70 (m, 6H), 1.50-1.20 (m, 18H), 0.9 (m, 9H)

$^{13}$C NMR (100 MHz, $CDCl_3$) $\delta_C$153.47, 138.20, 130.48, 106.68, 73.55, 69.26, 55.21, 32.08, 30.46, 29.90, 29.85, 29.79, 29.55, 29.52, 26.23, 22.84, 14.27

HRMS (M+H) 434.33

Mol. Formula: $C_{25}H_{43}N_3O_3$

Mol. Weight: 433.33

Physical appearance: pale yellow liquid

Yield: 96% xx. Synthesis of 7a

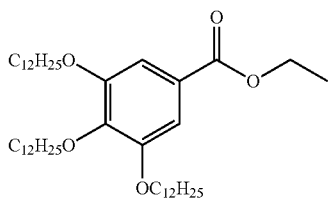

7a

The compound 7a was prepared by general procedure of example 3.2, starting from 3,4,5-trihydroxy ester (5 g, 25 mmol), dodecyl bromide (25 g, 100 mmol), $K_2CO_3$ (17 g, 125 mmol), KI (0.2 g, 1.2 mmol), in DMF. The product was obtained as a white solid (18 g, 25 mmol, 93%) after silica gel column chromatography using ethyl acetate/hexane as eluent.

$R_f$=0.46, solvent=5% ethyl acetate/hexane.

$^1$H NMR (400 MHz, $CDCl_3$) $\delta_H$7.25 (s, 2H), 4.34 (q, J=7.2 Hz 2H), 4.00 (t, J=6.8 Hz, 6H), 1.86-1.70 (m, 6H), 1.50-1.25 (m, 56H), 0.88 (t, J=6.8 Hz, 9H)

$^{13}$C NMR (400 MHz, $CDCl_3$) $\delta_C$ 166.38, 152.81, 142.33, 125.06, 108.00, 77.16, 73.49, 69.18, 64.13, 60.96, 31.98, 29.79, 29.76, 29.74, 29.70, 29.67, 29.61, 29.43, 29.41, 29.35, 26.12, 22.73, 14.42, 14.13.

MALDI-TOF (M+K) 741.59

Mol. formula: $C_{45}H_{82}H_5$

Mol. Weight: 702.61

Physical appearance: White solid

Yield: 93% xxi. Synthesis of 7b

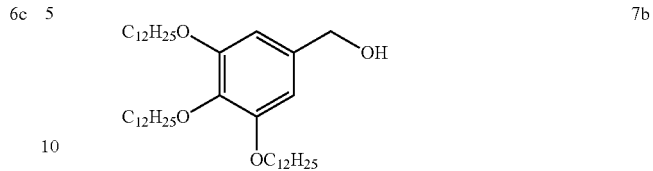

7b

The compound 7b was prepared by general procedure of example 3.3, starting from 7a (0.7 g, 1.5 mmol), LAH (0.16 g, 4.1 mmol) in THF. The product was obtained as a white solid (0.45 g, 0.7 mmol, 75%) after silica gel column chromatography using ethyl acetate/hexane as eluent.

$R_f$=0.25, solvent=10% ethyl acetate/hexane.

$^1$H NMR (400 MHz, $CDCl_3$) $\delta_H$6.55 (s, 2H), 4.53 (s, 2H), 3.97 (m, 6H), 1.83-1.67 (m, 6H), 1.48-1.26 (m, 57H), 0.87 (t, J=7.2 Hz, 9H)

$^{13}$C NMR (100 MHz, $CDCl_3$) $\delta_C$153.34, 137.53, 136.22, 105.33, 73.56, 69.16, 65.73, 32.06, 30.44, 29.90, 29.84, 29.80, 29.54, 26.24, 22.83, 14.25

MALDI-TOF (M+K) 669.54

Mol. formula: $C_{43}H_{80}O_4$

Mol. Weight: 660.60

Physical appearance: White solid

Yield: 75% xxii. Synthesis of 7c

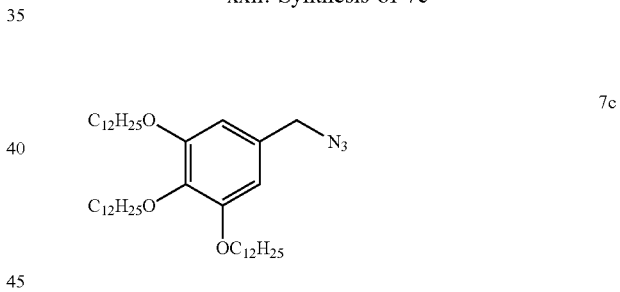

7c

The compound 7c was prepared by general procedure (3.4 and 3.5), from 7b (1.85 g, 2.7 mmol), generating chloride using $SOCl_2$ (0.5 g, 4 mmol) and subsequently synthesizing azide using sodium azide (0.2 g, 3 mmol). The product was obtained as a white solid (0.9 g, 1.3 mmol, 86%) after silica gel column chromatography using ethyl acetate/hexane as eluent.

$R_f$=0.44, solvent=5% ethyl acetate/hexane.

$^1$H NMR (400 MHz, $CDCl_3$) $\delta_H$6.48 (s, 2H), 4.24 (s, 2H), 3.97 (m, 6H), 1.83-1.68 (m, 6H), 1.48-1.26 (m, 57H), 0.87 (t, J=6.8 Hz, 9H)

$^{13}$C NMR (100 MHz, $CDCl_3$) $\delta_C$153.47, 138.20, 130.48, 106.68, 73.55, 69.26, 55.32, 32.08, 30.46, 29.90, 29.85, 29.79, 29.55, 29.52, 26.23, 22.84, 14.27

MALDI-TOF (M+Na) 708.60

Mol. formula: $C_{43}H_{79}O_3$

Mol. Weight: 685.61

Physical appearance: White solid

Yield: 86% xxiii. Synthesis of 8a

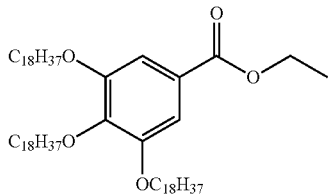

8a

The compound 8a was prepared by general procedure of example 3.2, starting from ethyl 3,4,5-trihydroxybenzoate (2 g, 10 mmol), octadecyl bromide (18.4 g, 54 mmol), $K_2CO_3$ (12.13 g, 87 mmol), KI (0.2 g, 1.0 mmol), in DMF. The product was obtained as a white solid (9.2 g, 9.5 mmol, 95%) after silica gel column chromatography using DCM/hexane as eluent.

$R_f$=0.46, solvent=5% ethyl acetate/hexane.

$^1$H NMR (400 MHz, CDCl$_3$) $\delta_H$7.25 (s, 2H), 4.34 (q, J=7.2 Hz 2H), 4.00 (t, J=6.4 Hz, 6H), 1.84-1.70 (m, 6H), 1.50-1.19 (m, 105H), 0.876 (t, J=6.8 Hz, 9H)

$^{13}$C NMR (100 MHz, CDCl$_3$) $\delta_C$166.62, 161.35, 152.93, 142.42, 125.18, 108.09, 77.16, 73.62, 69.30, 61.10, 32.09, 29.88, 29.83, 29.80, 29.53, 29.47, 29.34, 26.24, 22.85, 14.55, 14.27

MALDI-TOF (M+Na) 977.88

Mol. formula: $C_{63}H_{118}O_5$

Mol. Weight: 954.89

Physical appearance: White solid

Yield: 95% xxiv. Synthesis of 8b

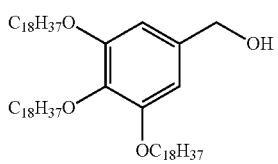

8b

The compound 8b was prepared by general procedure of example 3.3, starting from 8a (10 g, 10 mmol), LAH (2 g, 52 mmol) in THF. The product was obtained as a white solid (8 g, 9 mmol, 86%) after silica gel column chromatography using DCM/hexane as eluent.

$R_f$=0.34, solvent=10% ethyl acetate/hexane.

$^1$H NMR (400 MHz, CDCl$_3$) $\delta_H$6.55 (s, 2H), 4.58 (s, 2H), 3.97-3.91 (m, 6H), 1.81-1.70 (m, 6H), 1.47-1.25 (m, 96H), 0.88 (t, J=7.2 Hz, 9H)

$^{13}$C NMR (100 MHz, CDCl$_3$) $\delta_C$153.37, 137.58, 136.21, 105.37, 77.16, 73.63, 69.18, 65.76, 63.21, 32.07, 30.46, 29.87, 29.81, 29.57, 29.52, 26.28, 22.84, 14.27

MALDI-TOF (M+K) 951.82

Mol. formula: $C_{61}H_{116}O_4$

Mol. Weight: 912.88

Physical appearance: White solid

Yield: 86% xxv. Synthesis of 8c

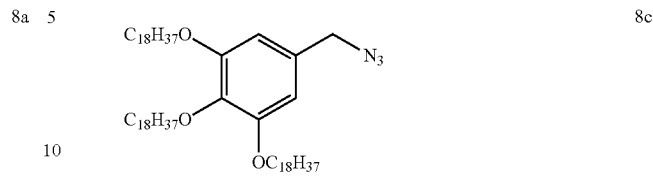

8c

The compound 8c was prepared by general procedure of examples (3.4 & 3.5), from 8b (3.5 g, 3.8 mmol). Chlorination of 8b accomplished using $SOCl_2$ (1 g, 7.6 mmol) reagent and subsequently azide functional group using sodium azide (0.9 g, 14 mmol) and TBAB (1.2 g, 0.4 mmol). The product is obtained as white solid (1.74 g, 1.8 mmol, 72%) after silica gel column chromatography using ethyl acetate/hexane as eluent.

$R_f$=0.44, solvent=5% ethyl acetate/hexane.

$^1$H NMR (400 MHz, CDCl$_3$) $\delta_H$6.48 (s, 2H), 4.24 (s, 2H), 3.95 (m, 6H), 1.84-1.70 (m, 6H), 1.50-1.19 (m, 95H), 0.87 (t, J=6.8 Hz, 9H)

$^{13}$C NMR (100 MHz, CDCl$_3$) $\delta_C$153.48, 138.21, 130.48, 106.68, 73.55, 69.26, 55.32, 32.09, 30.47, 29.88, 29.83, 29.57, 29.53, 26.24, 22.85, 14.27

MALDI-TOF (M+K) 976.76

Mol. formula: $C_{61}H_{115}N_3O_3$

Mol. Weight calculated: 937.89.

Physical appearance: White solid

Yield: 72%

Example 7: Procedure for the Synthesis of Oligoethylene Glycol Probes and their Intermediates i. Synthesis of 9a

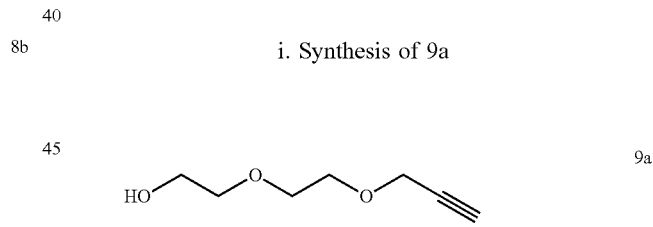

9a

The compound 9a was prepared by general procedure 4.1.1, starting from diethylene glycol (1.2 g, 11 mmol), NaH (0.034 g, 1.4 mmol), propargyl bromide (1.3 g, 10 mmol) in THF. The product was obtained as a pale yellow liquid (2.1 g, 15 mmol, 53%) after purification by silica gel column chromatography using MeOH/DCM as eluent, $R_f$=0.36 in 5% MeOH/DCM. $^1$H NMR (400 MHz, CDCl$_3$): $\delta_H$ 4.17 (d, J=2.4 Hz, 2H), 3.70-3.63 (m, 7H), 3.57 (t, J=4.4 Hz, 3H), 2.43 (t, J=2.4 Hz, 1H).

$^{13}$C NMR (100 MHz, CDCl$_3$): $\delta_C$ 79.47, 77.16, 74.83, 72.58, 70.17, 69.12, 61.65, 58.41.

HRMS (M+H): 145.12.

Mol. formula: $C_7H_{12}O_3$

Mol. Weight: 144.07

Physical appearance: pale yellow liquid

Yield: 53% ii. Synthesis of 9b

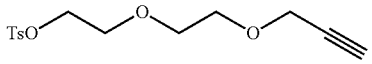
9b

The compound 9b was prepared by general procedure 4.1.2, starting from 9a (1 g, 7 mmol), tosyl chloride (1.5 g, 8 mmol), potassium hydroxide (1.3 g, 24 mmol) in THF. The product was obtained as a pale yellow liquid (1.8 g, 6 mmol, 90%) after purification by silica gel column chromatography using ethyl acetate/hexane as eluent, $R_f$=0.55 in 50% ethyl acetate/hexane. $^1$H NMR (400 MHz, CDCl$_3$): $\delta_H$ 7.78 (d, J=8 Hz, 2H), 7.32 (d, J=8 Hz, 2H), 4.17-4.13 (m, 4H), 3.70-3.58 (m, 6H), 2.44-2.41 (m, 4H).

$^{13}$C NMR (100 MHz, CDCl$_3$): $\delta_C$ 144.92, 132.94, 129.91, 128.04, 79.57, 77.16, 74.73, 70.59, 69.30, 69.05, 68.73, 60.45, 58.48, 21.71, 21.12, 14.31.

HRMS (M+Na): 321.07
Mol. formula: C$_{14}$H$_{18}$O$_5$S
Mol. Weight: 298.08
Physical appearance: pale yellow liquid
Yield: 90% iii. Synthesis of 9c

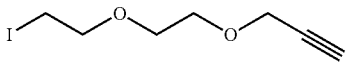
9c

Mol. formula: C$_7$H$_{11}$O$_2$I
Mol. Weight: 253.95
Physical appearance: pale yellow liquid
Yield: 92%

The compound 9c was prepared by general procedure 4.1.3, starting from 9b (1.5 g, 5 mmol), KI (3.3 g, 20 mmol) in acetone. The product was obtained as a pale yellow liquid (1.1 g, 4 mmol, 92%) after purification by silica gel column chromatography using MeOH/DCM as eluent, $R_f$=0.70 in 50% ethyl acetate/hexane. $^1$H NMR (400 MHz, CDCl$_3$): $\delta_H$ 4.17 (d, J=2.4 Hz, 2H), 3.70-3.63 (m, 7H), 3.57 (t, J=4.4 Hz, 3H), 2.43 (t, J=2.4 Hz, 1H).

$^{13}$C NMR (100 MHz, CDCl$_3$): $\delta_C$ 79.37, 77.16, 74.93, 72.48, 70.17, 69.32, 61.65, 58.41.

Mol. formula: C$_7$H$_{11}$O$_2$I
Mol. Weight: 253.95
Physical appearance: pale yellow liquid
Yield: 92% iv. Synthesis of 9d

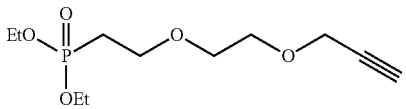
9d

The compound 9d was prepared by general procedure 4.1.4, starting from 9c (1 g, 4 mmol) and triethyl phosphite P(OEt)$_3$ (2.6 g, 15 mmol). The product was obtained as a pale yellow liquid (0.97 g, 3 mmol, 93%) after purification by silica gel column chromatography using MeOH/DCM as eluent, $R_f$=0.40 in 5% MeOH/DCM. $^1$H NMR (400 MHz, CDCl$_3$): $\delta_H$ 4.01-3.78 (m, 6H), 3.60-3.30 (m, 6H), 2.30 (m, 1H), 1.96-1.83 (m, 2H), 1.14-0.97 (m, 6H).

$^{13}$C NMR (100 MHz, CDCl$_3$): $\delta_C$ 79.13, 77.16, 74.49, 69.55, 68.62, 64.66, 61.28, 57.86, 27.19, 25.80, 16.03.

HRMS (M+Na): 287.12
Mol. formula: C$_{11}$H$_{21}$O$_5$P
Mol. Weight: 264.11
Physical appearance: pale yellow liquid
Yield: 93% v. Synthesis of 10a

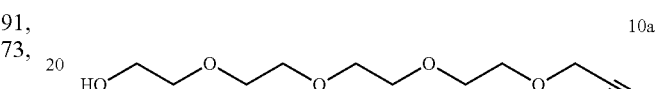
10a

The compound 10a was prepared by general procedure 4.1.1, starting from tetraethylene glycol (15 g, 77 mmol), NaH (1.23 g, 51 mmol), propargyl bromide (6.13 g, 51 mmol) in THF. The product was obtained as a pale yellow liquid (4.6 g, 30 mmol, 58%), after purification by silica gel column chromatography using MeOH/DCM as eluent, $R_f$=0.34 in 5% MeOH/DCM. $^1$H NMR (400 MHz, CDCl$_3$): $\delta_H$ 3.92 (d, J=2.4 Hz, 2H), 3.44-3.36 (m, 15H), 3.31 (t, J=4.4 Hz, 3H), 2.34 (t, J=2.4 Hz, 1H).

$^{13}$C NMR (100 MHz, CDCl$_3$): $\delta_C$ 79.15, 74.46, 72.03, 69.95, 69.89, 69.86, 69.70, 69.68, 68.43, 60.82, 57.68, 53.30.

HRMS (M+Na): 255.12.
Mol. formula: C$_{11}$H$_{20}$O$_5$
Mol. Weight: 232.13
Physical appearance: pale yellow liquid
Yield: 58% vi. Synthesis of 10b

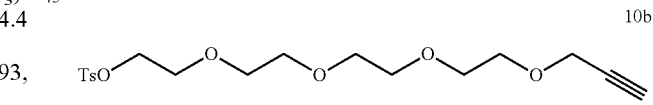
10b

The compound 10b was prepared by general procedure 4.1.2, starting from 10a (7.0 g, 30 mmol), tosyl chloride (4.1 g, 30 mmol), potassium hydroxide (4.0 g, 70 mmol) in THF. The product was obtained as a pale yellow liquid (8.2 g, 21 mmol, 71%) after purification by silica gel column chromatography using MeOH/DCM as eluent, 0.57 in 5% MeOH/DCM. $^1$H NMR (400 MHz, CDCl$_3$): $\delta_H$ 7.80 (d, J=8 Hz, 2H), 7.34 (d, J=8 Hz, 2H), 4.20-4.14 (m, 5H), 3.70-3.58 (m, 17H), 2.44-2.41 (m, 4H), 1.68 (s, 3H).

$^{13}$C NMR (100 MHz, CDCl$_3$): $\delta_C$ 144.89, 129.90, 128.07, 79.71, 74.62, 70.81, 70.65, 70.60, 70.46, 69.33, 69.18, 68.75, 58.47, 21.73.

HRMS (M+Na): 409.13
Mol. formula: C$_{18}$H$_{26}$O$_7$S
Mol. Weight: 386.45
Physical appearance: pale yellow liquid
Yield: 71% vii. Synthesis of 10c

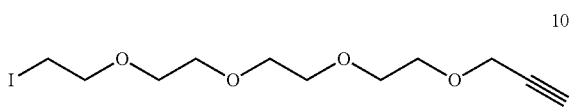

The compound 10c was prepared by general procedure 4.1.3, starting from 10b (26 g, 67 mmol), KI (40 g, 240 mmol) in acetone. The product was obtained as a pale yellow liquid (16.5 g, 48 mmol, 72%) after purification by silica gel column chromatography using MeOH/DCM as eluent, $R_f$=0.69 in 5% MeOH/DCM. $^1$H NMR (400 MHz, CDCl$_3$):

$\delta_H$ 4.16 (d, J=2.4 Hz, 2H), 3.73-3.62 (m, 15H), 3.22 (t, J=7.8 Hz, 2H), 2.41 (t, J=2.4 Hz, 1H).

$^{13}$C NMR (100 MHz, CDCl$_3$): $\delta_C$ 79.46, 77.16, 74.61, 71.82, 70.51, 70.29, 70.08, 68.98, 58.30, 3.17.

HRMS (M+Na): 365.02

Mol. formula: C$_{11}$H$_{19}$O$_4$I

Mol. Weight: 342.03

Physical appearance: pale yellow liquid

Yield: 72% viii. Synthesis of 10d

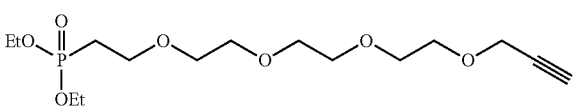

The compound 10d was prepared by general procedure 4.1.4, starting from 10c (0.200 g, 0.50 mmol) and triethyl phosphite P(OEt)$_3$ (0.67 g, 4 mmol). The product was obtained as a pale yellow liquid (0.153 g, 0.4 mmol, 75%) after purification by silica gel column chromatography using MeOH/DCM as eluent, $R_f$=0.4 in 5% MeOH/DCM. $^1$H NMR (400 MHz, CDCl$_3$): $\delta_H$ 4.19 (s, 2H), 4.14-4.01 (m, 4H), 3.73-3.53 (m, 14H), 2.43 (t, J=2.4 Hz, 1H), 2.18-1.97 (m, 2H), 1.31 (t, J=7.2 Hz).

$^{13}$C NMR (100 MHz, CDCl$_3$): $\delta_C$ 79.82, 77.16, 74.70, 70.77, 70.69, 70.57, 70.35, 69.28, 65.29, 61.79, 61.73, 58.55, 27.87, 26.49, 16.59.

HRMS (M+Na): 375.15

Mol. formula: C$_{15}$H$_{29}$O$_7$P

Mol. Weight: 352.17

Physical appearance: pale yellow liquid

Yield: 75% ix. Synthesis of 11a

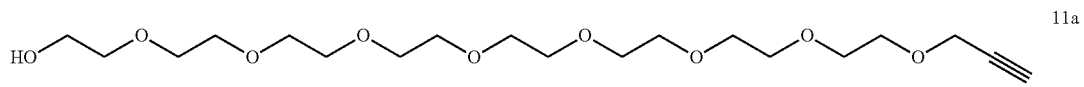 [SMILES: C#CCOCCOCCOCCOCCOCCOCCOCCOCCO]

The compound 11a was prepared by general procedure 4.1.1, starting from 10b (7.3 g, 18 mmol), TEG (9.0 g, 46 mmol) and NaH (0.9 g, 37 mmol) in THF. The product obtained was carried to next step without purification, $R_f$=0.4 in 5% MeOH/DCM.

HRMS (M+H): 409.24.

Mol. formula: C$_{19}$H$_{36}$O$_9$

Mol. Weight: 408.48

Physical appearance: colourless liquid

Yield: not determined x. Synthesis of 11b

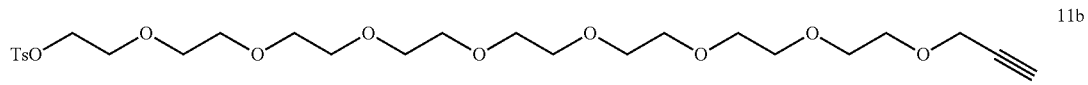 [SMILES: C#CCOCCOCCOCCOCCOCCOCCOCCOCCOS(=O)(=O)c1ccc(C)cc1]

The compound 11b was prepared by general procedure 4.2.2, starting from 11a (9.9 g), tosyl chloride (46 g, 422 mmol), triethyl amine (57 g, 564 mmol) and DMAP (1.7 g, 13 mmol) in DCM. The product was obtained as pale yellow liquid (3.3 g, 5.0 mmol) after purification by silica gel column chromatography using MeOH/DCM as eluent, $R_f$=0.4 in 5% MeOH/DCM.

$^1$H NMR (400 MHz, CDCl$_3$): $\delta_H$ 7.77 (d, J=8 Hz, 2H), 7.32 (d, J=8 Hz, 2H), 4.18 (d, J=2.4 Hz, 2H), 4.14 (t, J=3.2 Hz, 2H), 3.69-3.66 (m, 6H), 3.65-3.61 (m, 20H), 3.57 (s, 4H), 2.42 (m, 4H).

$^{13}$C NMR (100 MHz, CDCl$_3$): $\delta_C$ 144.78, 132.79, 129.76, 127.87, 70.60, 70.42, 69.20, 68.56, 21.56.

MALDI-TOF MS (M+K): 601.11.

Mol. formula: C$_{26}$H$_{42}$O$_{11}$S

Mol. Weight: 562.24

Physical appearance: pale yellow liquid

Yield: 42% xi. Synthesis of 11c

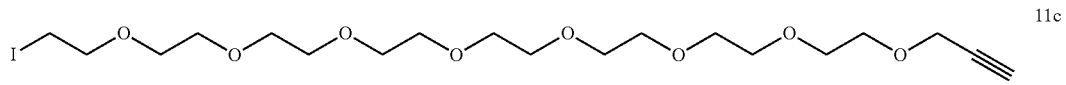 [SMILES: C#CCOCCOCCOCCOCCOCCOCCOCCOCCI]
11c

A mixture of compound 11b (4.6 g, 8.1 mmol) and KI (5.4 g, 32 mmol) was refluxed in acetone for 18 hours. Upon completion, excess KI is filtered and washed thrice with acetone. Collected acetone fraction was evaporated under vacuum to get residue, which was then washed with water and extracted with DCM. The combined organic layer was washed with aqueous $Na_2CO_3$ and then concentrated under vacuum to get crude product which was purified using silica gel column chromatography using MeOH/DCM as eluent to get pale yellow liquid product (4 g, 7.72 mmol, 95%).

$R_f$=0.4, solvent=5% methanol/DCM.

$^1$H NMR (400 MHz, $CDCl_3$) $\delta_H$4.19 (d, J=2.4 Hz, 2H), 3.75 (t, J=7.2 Hz, 3H), 3.69-3.61 (m, 33H), 3.25 (t, J=7.2 Hz, 2H), 2.43 (t, J=2.4 Hz, 1H)

$^{13}$C NMR (100 MHz, $CDCl_3$) $\delta_C$79.77, 74.68, 72.09, 70.78, 70.70, 70.52, 70.33, 69.22, 58.53

MALDI-TOF (M+K) 557.03

Mol. formula: $C_{19}H_{35}IO_8$

Mol. Weight: 518.13

Physical appearance: pale yellow liquid

Yield: 95% xii. Synthesis of 11d

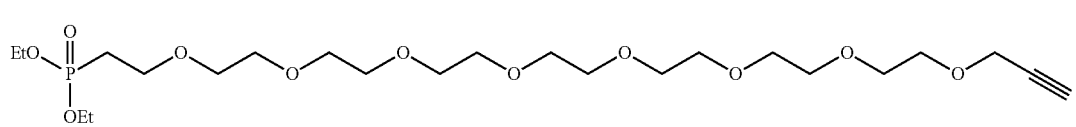
11d

Compound 11c (4 g, 7.72 mmol) and triethylphosphite $(P(OEt)_3)$ (5.9 g, 32 mmol) were refluxed for 1 hour at 150° C. in an oven-dried RBF. The excess $PPh_3$ was removed under vacuum and the reaction mixture was directly loaded onto a silica-gel column to get pale yellow liquid product (5.61 g, 10.6 mmol, 89%) using MeOH/DCM as eluent.

$R_f$=0.4, solvent=5% methanol/DCM.

$^1$H NMR (400 MHz, $CDCl_3$) $\delta_H$4.18 (m, 2H), 4.12-4.03 (m, 4H), 3.72-3.58 (m, 30H), 2.42 (t, J=2.4 Hz, 1H) 2.16-2.07 (m, 2H), 1.30 (t, J=7.2 Hz, 6H)

$^{13}$C NMR (100 MHz, $CDCl_3$) $\delta_C$79.64, 74.65, 70.54, 70.43, 70.39, 70.17, 69.09, 65.12, 61.69, 61.63, 58.41

MALDI-TOF (M+K) 567.15

Mol. formula: $C_{23}H_{45}O_{11}P$

Mol. Weight: 528.26

Physical appearance: pale yellow liquid

Yield: 89% xiii. Synthesis of 12a

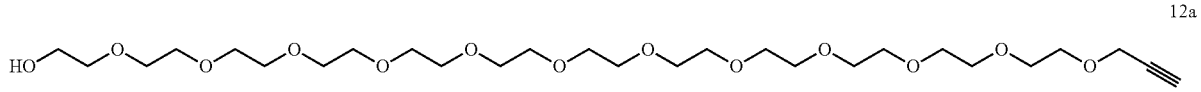 [SMILES: C#CCOCCOCCOCCOCCOCCOCCOCCOCCOCCOCCOCCOCCO]
12a

Mol. formula: $C_{27}H_{52}O_{13}$
Mol. Weight: 584.70
Physical appearance: colourless liquid
Yield: not determined
The compound 12a was prepared by general procedure 4.2.1, starting from 11b (5.3 g, 9.0 mmol), TEG (4.5 g, 23 mmol) and NaH (0.45 g, 16 mmol) in THF. The product obtained was carried to next step without purification, $R_f$=0.4 in 5% MeOH/DCM.
MALDI-TOF MS (M+Na): 607.12.

xiv. Synthesis of 12b

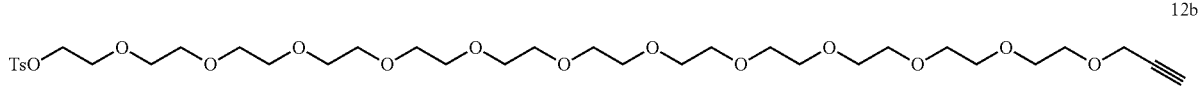 [SMILES: C#CCOCCOCCOCCOCCOCCOCCOCCOCCOCCOCCOCCOCCOS(=O)(=O)c1ccc(C)cc1]

12b

The compound 12b was prepared by general procedure 4.2.2, starting from 12a (7.1 g), tosyl chloride (33 g, 304 mmol), triethyl amine (40 g, 405 mmol) and DMAP (1.2 g, 10 mmol) in DCM. The product was obtained as pale yellow liquid after purification by silica gel column chromatography using MeOH/DCM as eluent, $R_f$=0.4 in 5% MeOH/DCM.

NMR (400 MHz, CDCl$_3$): $\delta_H$ 7.79 (d, J=8 Hz, 2H), 7.34 (d, J=8 Hz, 2H), 4.19-4.13 (m, 4H), 3.71-3.56 (m, 52H), 2.43-2.42 (m, 4H), 1.95 (s, 3H).
$^{13}$C NMR (100 MHz, CDCl$_3$): $\delta_C$ 144.88, 133.03, 129.91, 12.07, 79.72, 74.65, 70.80, 70.66, 70.61, 70.57, 70.46, 69.32, 69.17, 68.74, 58.47, 21.73.
MALDI-TOF MS (M+K): 777.05.
Mol. formula: $C_{34}H_{58}O_{15}S$
Mol. Weight: 738.88
Physical appearance: pale yellow liquid
Yield: not determined xv. Synthesis of 12c

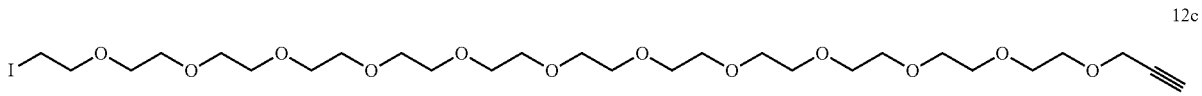 [SMILES: C#CCOCCOCCOCCOCCOCCOCCOCCOCCOCCOCCOCCOCCI]

12c

The compound 12c was prepared by general procedure 4.1.3, starting from 12b (0.40 g, 0.5 mmol), KI (0.25 g, 2.0 mmol) in acetone. The product was obtained as a pale yellow liquid (0.38 g, 0.5 mmol, 90%) after purification by silica gel column chromatography using MeOH/DCM as eluent, $R_f$=0.4 in 5% MeOH/DCM.

$^1$H NMR (400 MHz, CDCl$_3$): $\delta_H$ 4.19 (d, J=2.4 Hz, 2H), 3.75 (t, J=7.2 Hz, 2H), 3.69-3.64 (m, 49H), 3.25 (t, J=2.4 Hz, 1H).
$^{13}$C NMR (100 MHz, CDCl$_3$): $\delta_C$ 79.79, 77.16, 74.67, 72.14, 70.78, 70.69, 70.67, 70.52, 70.34, 69.23, 58.53.
MALDI-TOF MS (M+K): 732.97
Mol. formula: $C_{27}H_{51}IO_{12}$
Mol. Weight: 693.59
Physical appearance: pale yellow liquid
Yield: 90% xvi. Synthesis of 12d

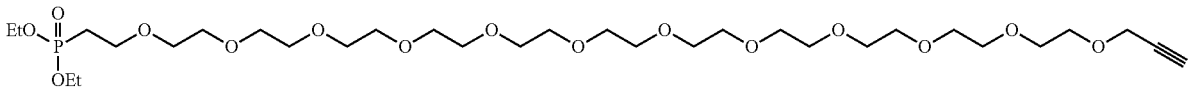

12d

The compound 12d was prepared by general procedure 4.1.4, starting from 12c (0.21 g, 0.30 mmol) and triethyl phosphite P(OEt)$_3$ (0.20 g, 1.2 mmol). The product was obtained as a pale yellow liquid (0.18 g, 0.25 mmol, 87%) after purification by silica gel column chromatography using MeOH/DCM as eluent, R$_f$=0.4 in 5% MeOH/DCM.

$^1$H NMR (400 MHz, CDCl$_3$): δ$_H$ 4.19 (m, 2H), 4.12-4.03 (m, 4H), 3.76-3.54 (m, 51H), 2.43 (t, J=2.4 Hz, 1H), 2.17-2.06 (m, 2H), 1.30 (t, J=7.8 Hz, 6H).

$^{13}$C NMR (100 MHz, CDCl$_3$): δ$_C$ 79.76, 77.16, 74.68, 70.67, 70.28, 69.21, 65.24, 61.70, 58.51, 16.52.

MALDI-TOF MS (M+K): 743.06.

Mol. formula: C$_{31}$H$_{61}$O$_{15}$P

Mol. Weight: 704.78

Physical appearance: pale yellow liquid

Yield: 87% xvii. Synthesis of 13a

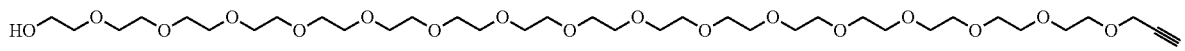

13a

The compound 13a was prepared by general procedure 4.2.1, starting from 12b (0.77 g, 1 mmol), TEG (0.5 g, 2.5 mmol) and NaH (0.05 g, 2 mmol) in THF. The product obtained was carried to next step without purification, R$_f$=0.4 in 5% MeOH/DCM.

MALDI-TOF MS (M+Na): 783.20.

Mol. formula: C$_{35}$H$_{68}$O$_{17}$

Mol. Weight: 760.91

Physical appearance: pale yellow liquid

Yield: not determined xviii. Synthesis of 13b

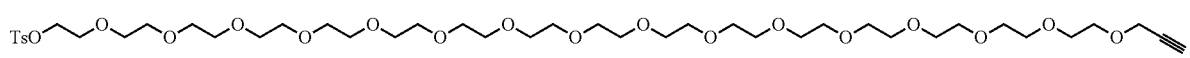

13b

The compound 13b was prepared by general procedure 4.2.2, starting from 13a (0.7 g), tosyl chloride (2.3 g, 21 mmol) triethyl amine (2.8 g, 27 mmol) and DMAP (0.08 g, 0.6 mmol) in DCM. The product was obtained as pale yellow liquid after purification by silica gel column chromatography using MeOH/DCM as eluent, R$_f$=0.4 in 5% MeOH/DCM. $^1$H NMR (400 MHz, CD$_3$OD) δ$_H$ 7.83 (d, J=8 Hz, 2H), 7.48 (d, J=8 Hz, 2H), 4.20-4.15 (m, 4H), 3.69-3.54 (m, 53H), 3.32 (s, 7H), 2.87 (t, J=2.4 Hz, 1H), 2.48 (s, 3H).

$^{13}$C NMR (100 MHz, MeOD$_4$) δ$_C$ 146.44, 134.43, 130.83, 129.09, 76.09, 71.56, 71.37, 70.97, 70.10, 69.75, 59.03, 54.83, 49.00, 21.62.

MALDI-TOF MS (M+K): 953.22.

Mol. formula: C$_{42}$H$_{74}$O$_{19}$S

Mol. Weight: 914.09

Physical appearance: pale yellow liquid

Yield: not determined xix. Synthesis of 13c

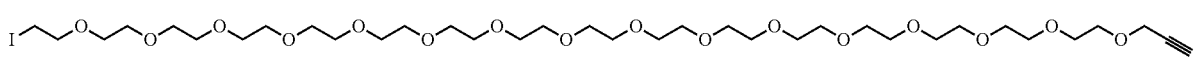

13c

The compound 13C was prepared by general procedure 4.1.3, starting from 13b (0.21 g, 0.23 mmol), KI (0.15 g, 0.90 mmol) in acetone. The product was obtained as a pale yellow liquid (0.18 g, 0.21 mmol, 92%) after purification by silica gel column chromatography using MeOH/DCM as eluent, $R_f$=0.4 in 5% MeOH/DCM.

$^1$H NMR (400 MHz, MeOD$_4$): $\delta_H$ 4.21 (d, J=4 Hz, 2H), 3.78 (t, J=8 Hz, 2H), 3.70-3.65 (m, 62H), 3.34-3.31 (m, 6H), 2.88 (t, J=4 Hz, 1H).

$^{13}$C NMR (100 MHz, CD$_3$OD): $\delta_C$ 80.65, 75.96, 73.10, 71.64, 71.56, 71.37, 71.17, 70.11, 59.05, 54.81, 49.00.
MALDI-TOF MS (M+K): 909.26.
Mol. formula: C$_{35}$H$_{67}$IO$_{16}$
Mol. Weight: 870.80
Physical appearance: pale yellow liquid
Yield: 92% xx. Synthesis of 13d

13d

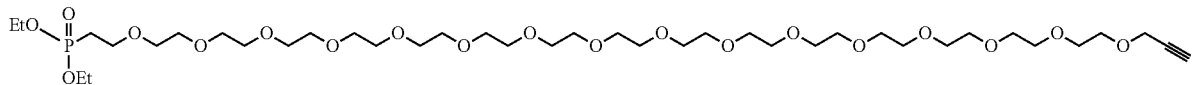

The compound 13d was prepared by general procedure 4.1.4, starting from 13c (0.186 g, 0.21 mmol) and triethyl phosphite P(OEt)$_3$ (0.141 g, 0.84 mmol). The product was obtained as a pale yellow liquid (0.17 g, 0.2 mmol, 93%) after purification by silica gel column chromatography using MeOH/DCM as eluent, $R_f$=0.4 in 5% MeOH/DCM.

$^1$H NMR (400 MHz, CD$_3$OD): $\delta_H$ 4.19 (d, J=2 Hz, 2H), 4.16-4.03 (m, 4H), 3.76-3.58 (m, 64H), 2.43 (t, J=2.4 Hz, 1H), 2.15-2.06 (m, 2H), 1.32 (t, J=8 Hz, 6H).
$^{13}$C NMR (100 MHz, MeOD$_4$): $\delta_C$ 109.07, 104.14, 99.85, 99.56, 98.20, 91.48, 87.18, 83.00, 77.16, 54.69, 44.89.
MALDI-TOF MS (M+K): 919.18.
Mol. formula: C$_{39}$H$_{77}$O$_{19}$P
Mol. Weight: 880.99
Physical appearance: pale yellow liquid
Yield: 93%

Example 8: Specific Synthetic Procedure of Clicked Products (AABPs) and their Intermediates A. Synthesis of Intermediates for Tail Variants Variant AABPs.

i. Synthesis of Compound 14a

14a

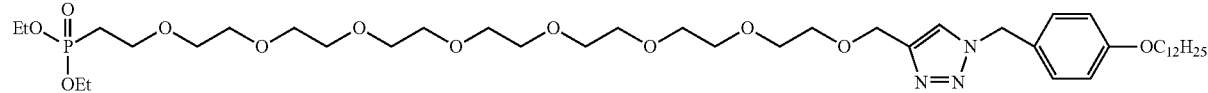

The compound 14a was synthesized using general procedure 5.1, starting from 11d (200 mg, 0.37 mmol), 1b (120 mg, 0.37 mmol), CuSO$_4$ (4.71 mg, 0.0189 mmol), sodium ascorbate (7.5 mg, 0.0378 mmol) in THF/water (50:50). The product obtained was purified using reverse phase chromatography using ACN/water followed by chloroform and normal phase chromatography using MeOH/DCM to get brownish liquid (0.21 g, 0.24 mmol, 65%), $R_f$=0.4 in 5% MeOH/DCM.

$^1$H NMR (400 MHz, CDCl$_3$): $\delta_H$ 7.45 (s, 1H), 7.19 (d, J=8.8 Hz, 2H), 6.86 (d, J=8.8 Hz, 2H), 5.47 (s, 2H), 4.63 (s, 2H), 4.19-4.00 (m, 4H), 3.93 (t, J=6.4 Hz, 2H), 3.74-3.57 (m, 31H), 2.18-2.03 (m, 2H), 1.81-1.71 (m, 2H), 1.47-1.19 (m, 27H), 0.87 (t, J=6.8 Hz, 3H).
$^{13}$C NMR (100 MHz, CDCl$_3$): $\delta_C$ 159.38, 129.57, 126.26, 114.87, 77.16, 70.45, 70.43, 70.35, 70.08, 69.60, 67.99, 65.01, 64.59, 61.54, 53.59, 31.80, 29.54, 29.52, 29.48, 29.46, 29.27, 29.23, 29.09, 27.57, 25.92, 22.57, 14.03.
MALDI-TOF MS (M+K): 884.53.
Mol. formula: C$_{42}$H$_{76}$N$_3$O$_{12}$P
Mol. Weight: 845.51
Physical appearance: brownish liquid
Yield: 65% ii. Synthesis of 14b

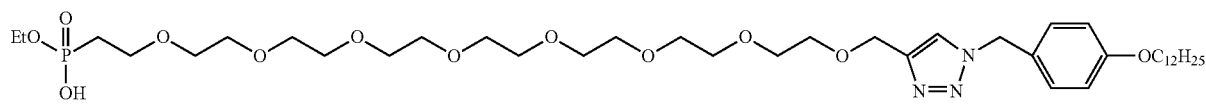

14b

The compound 14b was synthesized using general procedure 5.2, starting from 14a (120 mg, 0.14 mmol), oxalyl chloride (94 mg, 0.56 mmol) in DCM. The product obtained was carried to next step without purification.

$^1$H NMR (400 MHz, CDCl$_3$): δ$_H$ 7.30 (s, 1H), 7.15 (d, J=8.8 Hz, 2H), 6.81 (d, J=8.8 Hz, 2H), 5.38 (s, 2H), 4.59 (s, 2H), 4.28-4.14 (m, 4H), 3.88 (t, J=6.4 Hz, 2H), 3.76-3.52 (m, 31H), 2.25-2.17 (m, 2H), 1.78-1.63 (m, 2H), 1.43-1.16 (m, 27H), 0.82 (t, J=6.8 Hz, 3H).

MALDI-TOF MS (M+Na):
Mol. formula: C$_{40}$H$_{72}$N$_3$O$_{12}$P
Mol. Weight: 817.48
Physical appearance: pale yellow liquid
Yield: not determined iii. Synthesis of Compound 14c [ethyl (1-(1-(4-(dodecyloxy)benzyl)-1H-1,2,3-triazol-4-yl)-2,5,8,11,14,17,20,23-octaoxapentacosan-25-yl)phosphonofluoridate] C12-1T

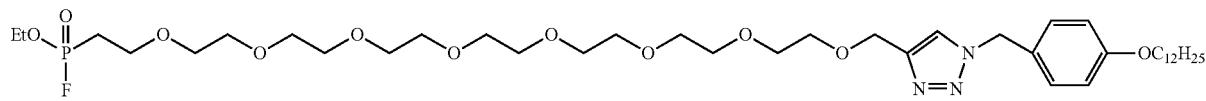

14c

The compound 14c was synthesized using general procedure 5.3, starting from 14b (100 mg, 0.122 mmol), DAST (99 mg, 0.59 mmol) in DCM. The product obtained was used for modification without purification.

$^{19}$F NMR (400 MHz, CDCl$_3$): δ$_F$ −59.91, −62.74.
MALDI-TOF MS (M+K): 858.50.
Mol. formula: C$_{40}$H$_{71}$N$_3$O$_{11}$PF
Mol. Weight: 819.48
Physical appearance: brownish liquid
Yield: not determined iv. Synthesis of Compound 15a

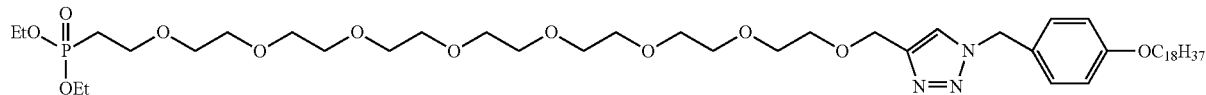

15a

The compound 15a was synthesized using general procedure 5.1, starting from 11d (100 mg, 0.189 mmol), 2b (71 mg, 0.89 mmol), CuSO$_4$ (2.3 mg, 0.009 mmol), sodium ascorbate (3.7 mg, 0.0162 mmol) in THF/water/DCM (50:25:25). The crude product obtained was purified using reverse phase chromatography using ACN/water followed by chloroform and normal phase chromatography using MeOH/DCM to get brownish liquid (0.13 g, 0.14 mmol, 76%), R$_f$=0.4 in 5% MeOH/DCM.

$^1$H NMR (400 MHz, CDCl$_3$): δ$_H$ 7.45 (s, 1H), 7.38 (d, J=8.8 Hz, 2H), 6.85 (d, J=8.8 Hz, 2H), 5.42 (s, 2H), 4.63 (s, 2H), 4.12-3.99 (m, 4H), 3.92 (t, J=6.4 Hz, 2H), 3.72-3.57 (m, 31H), 2.16-2.03 (m, 2H), 1.83-1.69 (m, 2H), 1.46-1.16 (m, 38H), 0.86 (t, J=6.8 Hz, 3H).

$^{13}$C NMR (100 MHz, CDCl$_3$): δ$_C$. 159.58, 145.51, 129.80, 126.36, 122.47, 115.09, 77.16, 70.61, 70.58, 70.55, 70.51, 70.47, 70.12, 69.81, 68.23, 65.27, 64.73, 61.26, 53.86, 53.55, 32.02, 29.79, 29.76, 29.71, 29.68, 29.50, 29.46, 29.30, 28.05, 26.66, 26.13, 22.79, 14.23.

MALDI-TOF MS (M+K): 968.68.
Mol. formula: C$_{48}$H$_{88}$N$_3$O$_{12}$P
Mol. Weight: 929.61
Physical appearance: brownish liquid
Yield: 76% v. Synthesis of Compound 15b

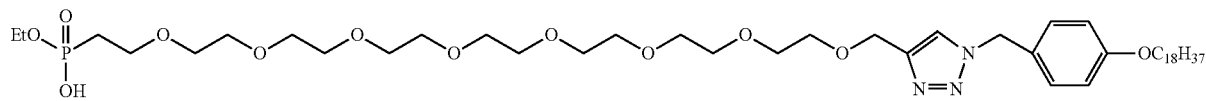

15b

The compound 15b was synthesized using general procedure 5.2, starting from 15a (0.100 g, 0.134 mmol), oxalyl chloride (0.071 g, 0.43 mmol) in DCM. The product obtained was carried to next step without purification.

$^1$H NMR (400 MHz, CDCl$_3$): δ$_H$ 7.46 (s, 1H), 7.19 (d, J=8.8 Hz, 2H), 6.85 (d, J=8.8 Hz, 2H), 5.42 (s, 2H), 4.63 (s, 2H), 4.14-3.97 (m, 2H), 3.92 (t, J=6.4 Hz, 2H), 3.77-3.51 (m, 30H), 2.16-2.03 (m, 2H), 1.77-1.68 (m, 2H), 1.46-1.16 (m, 35H), 0.86 (t, J=6.8 Hz, 3H).

MALDI-TOF MS (M+Na): 924.64.
Mol. formula: C$_{46}$H$_{84}$N$_3$O$_{12}$P
Mol. Weight: 901.57
Physical appearance: pale yellow liquid
Yield: not determined vi. Synthesis of 15c [Synthesis of 15c [ethyl (1-(1-(4-(octadecyloxy)benzyl)-1H-1,2,3-triazol-4-yl)-2,5,8,11,14,17,20,23-octaoxapentacosan-25-yl)phosphonofluoridate] C18-1T

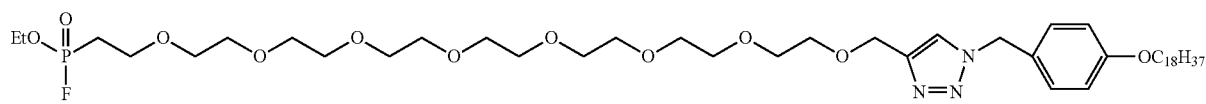

15c

The compound 15c was synthesized using general procedure 5.3, starting from 15b (0.80 g, 0.08 mmol), DAST (0.06 mg, 0.39 mmol) in DCM. The product obtained was used for modification without purification.

$^{19}$F NMR (400 MHz, CDCl$_3$): δ$_F$ −59.91, −62.74.
MALDI-TOF MS (M+Na): 926.24.
Mol. formula: C$_{46}$H$_{83}$N$_3$O$_{11}$PF
Mol. Weight: 903.57
Physical appearance: brownish liquid
Yield: not determined vi. Synthesis of 16a

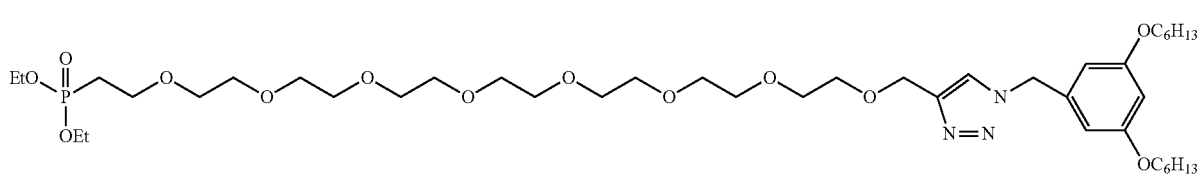

16a

The compound 16a was synthesized using general procedure of example 5.1, starting from 11d (0.475 g, 0.899 mmol), 3d (0.300 g, 0.899 mmol), CuSO$_4$ (11 mg, 0.044 mmol), sodium ascorbate (17 mg, 0.085 mmol) in THF/water (50:50). The product obtained was purified using reverse phase chromatography using acetonitrile/water followed by chloroform and normal phase chromatography using MeOH/DCM to get brownish liquid (0.502 g, 582 mmol, 65%).

R$_f$=0.4, solvent=5% methanol/DCM $^1$H NMR (400 MHz, CDCl$_3$) δ$_H$ 7.46 (s, 1H), 6.41-6.35 (m, 3H), 4.63 (s, 2H), 4.11-4.00 (m, 4H), 3.85 (t, J=6.4 Hz, 4H), 3.72-3.52 (m, 32H), 2.12-2.03 (m, 2H), 1.46-1.27 (m, 20H), 0.872 (m, 6H)

$^{13}$C NMR (100 MHz, CDCl$_3$) δ$_C$ 160.91, 145.62, 136.58, 122.63, 106.70, 101.38, 70.68, 70.64, 70.57, 70.54, 70.27, 69.83, 68.27, 65.21, 64.81, 61.74, 54.34, 31.63, 29.28, 27.88, 26.40, 25.76, 22.65, 16.47, 14.09

MALDI-ToF (M+K) 900.56

Mol. formula: C$_{42}$H$_{76}$N$_3$O$_{13}$P

Mol. Weight: 861.51

Physical appearance: brownish liquid

Yield: 65% vii. Synthesis of 16b

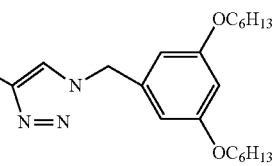

16b

The compound 16b was synthesized using general procedure of example 5.2, starting from 16a (0.491 g, 0.569 mmol), oxalyl chloride (0.291 g, 2.2 mmol) in DCM. The product was taken to the next step without further purification.

MALDI-ToF (M+K) 872.37

Mol. formula: C$_{40}$H$_{72}$N$_3$O$_{13}$P

Mol. Weight: 833.48

Physical appearance: brownish liquid

Yield: not determined.

viii. Synthesis of 19c [ethyl (1-(1-(3,5-bis(hexyloxy)benzyl)-1H-1,2,3-triazol-4-yl)-2,5,8,11,14,17,20,23-octaoxapentacosan-25-yl)phosphonofluoridate] C6-2T

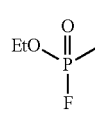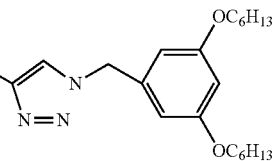

16c

The compound 16c was synthesized using general procedure of example 5.3 starting from 16b (0.425 g, 0.510 mmol), DAST (0.374 g, 2.3 mmol), in DCM. The product was used for conjugation without further purification.

$^{19}$F NMR (400 MHz, CDCl$_3$) δ$_F$ −59.91, −62.74

MALDI-TOF (M+Na) 858.45

Mol. formula: C$_{40}$H$_{71}$N$_3$O$_{12}$PF

Mol. Weight: 835.47

Physical appearance: brownish liquid

Yield: not determined ix. Synthesis of 17a

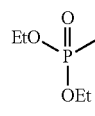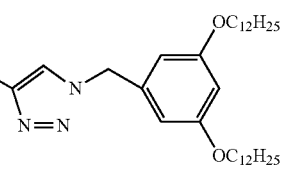

17a

The compound 17a was synthesized using general procedure of example 5.1, starting from 11d (0.100 g, 0.189 mmol), 4c (0.94 g, 0.189 mmol), CuSO₄ (2.48 mg, 0.0096 mmol), sodium ascorbate (3.94 mg, 0.0198 mmol) THF/water (50:50). The product obtained was purified using reverse phase chromatography using acetonitrile/water followed by chloroform and normal phase chromatography using MeOH/DCM to get brownish liquid (0.133 g, 2.3 mmol, 68%).

$R_f$=0.4 in 5% methanol/DCM.

¹H NMR (400 MHz, CDCl₃) $δ_H$7.50 (s, 1H), 6.40-6.37 (m, 3H), 5.398 (s, 2H), 4.65 (s, 2H), 4.14-4.03 (m, 4H), 3.88 (t, J=6.4 Hz, 4H), 3.73-3.53 (m, 30H), 2.16-2.08 (m, 2H), 1.47-1.19 (m, 60H), 0.87 (t, J=6.8 Hz, 8H)

¹³C NMR (100 MHz, CDCl₃) $δ_C$160.91, 145.62, 136.58, 122.63, 106.70, 101.38, 70.68, 70.64, 70.57, 70.54, 70.27, 69.83, 68.27, 65.21, 64.81, 61.74, 54.34, 31.63, 29.81, 29.79, 29.75, 29.73, 29.54, 29.51, 29.36, 26.18, 22.77, 16.47, 14.09

MALDI-TOF (M+K) 1068.71
Mol. formula: $C_{54}H_{100}N_3O_{13}P$
Mol. Weight: 1029.69
Physical appearance: brownish liquid
Yield: 68% x. Synthesis of 17b

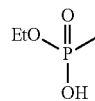 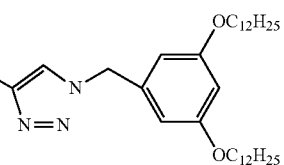

17b

The compound 17b was synthesized using general procedure of example 5.2, starting from 17a (45 mg, 0.0437 mmol), oxalyl chloride (22 mg, 0.170 mmol), in DCM. Product was taken to next step without further purification.

MALDI-TOF (M+K)=1040.63
Mol. formula: $C_{52}H_{96}N_3O_{13}P$
Mol. Weight: 1001.66
Physical appearance: brownish liquid
Yield: not determined xi. Synthesis of 20c [ethyl (1-(1-(3,5-bis(dodecyloxy)benzyl)-1H-1,2,3-triazol-4-yl)-2,5,8,11,14,17,20,23-octaoxapentacosan-25-yl)phosphonofluoridate] C12-2T

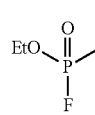 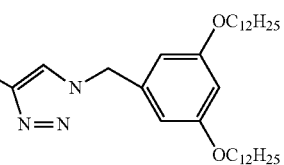

17c

The compound 17c was synthesized using general procedure of example 5.3, starting from 17b (44 mg, 0.0437 mmol), DAST (257 mg, 0.159 mmol), in DCM. Product was used for conjugation without further purification.

¹⁹F NMR (400 MHz, CDCl₃) $δ_F$-59.91, -62.74
MALDI-TOF (M+K)=1042.96
Mol. formula: $C_{52}H_{95}N_3O_{12}PF$
Mol. Weight: 1003.66
Physical appearance: brownish liquid
Yield: not determined xii. Synthesis of 18a

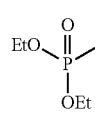 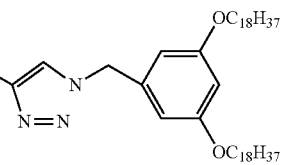

18a

The compound 18a was synthesized using general procedure of example 5.1, starting from 11d (100 mg, 189 mmol), 5d (142 mg, 212 mmol), CuSO$_4$ (2 mg, 0.008 mmol) sodium ascorbate (3.37 mg, 0.00189 mmol), in THF/water (50:50). The product obtained was purified using reverse phase chromatography using acetonitrile/water followed by chloroform and normal phase chromatography using MeOH/DCM to get brownish liquid (0.159 g, 135 mmol, 68%), R$_f$=0.4 in 5% methanol/DCM.

$^1$H NMR (400 MHz, CDCl$_3$) δ$_H$7.56 (s, 1H), 6.42-6.39 (m, 3H), 5.41 (s 2H), 4.67 (s, 2H), 4.15-4.05 (m, 4H), 3.90 (t, J=6.4 Hz, 4H), 3.75-3.57 (m, 33H), 2.18-2.08 (m, 2H), 1.77-1.70 (m, 4H), 1.45-1.27 (m, 81H), 0.894 (t, J=6.8 Hz, 6H)

$^{13}$C NMR (100 MHz, CDCl$_3$) δ$_C$ 160.79, 136.49, 106.55, 101.27, 70.65, 70.47, 70.17, 69.64, 68.13, 65.11, 64.70, 61.62, 54.33, 31.91, 29.69, 29.60, 29.56, 29.38, 29.35, 29.18, 27.67, 26.28, 26.12, 22.57, 16.45, 14.11

MALDI-TOF (M+K) 1236.84

Mol. formula: C$_{66}$H$_{124}$N$_3$O$_{13}$P

Mol. Weight: 1197.88

Physical appearance: brownish liquid

Yield: 68% xiii. Synthesis of 18b

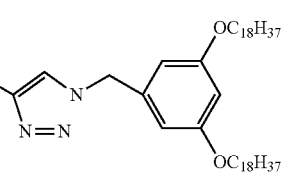

18b

The compound 18b was synthesized using general procedure of example 5.2, starting from 18a (100 mg, 0.0834 mmol), oxalyl chloride (53 mg, 0.329 mmol) in DCM. The product was carried to next step without purification.

Mol. formula: C$_{64}$H$_{120}$N$_3$O$_{13}$P

Mol. Weight: 1169.85

Physical appearance: brownish liquid

Yield: not determined

MALDI-TOF (M+Na) 1192.78 xiv. Synthesis of 21c [ethyl (1-(1-(3,5-bis(octadecyloxy)benzyl)-1H-1,2,3-triazol-4-yl)-2,5,8,11,14,17, 20,23-octaoxapentacosan-25-yl)phosphonofluoridate] C18-2T

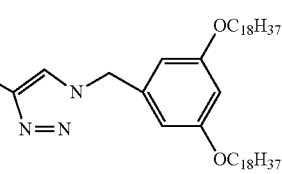

18c

The compound 18c was synthesized using general procedure of example 5.3 starting from 18b (70 mg, 0.0597 mmol), DAST (21.9 mg, 0.136 mmol) in DCM. The product was used for conjugation without further purification.

$^{19}$F NMR (400 MHz, CDCl$_3$) δ$_F$-59.91, -62.74.

Mol. formula: C$_{64}$H$_{119}$N$_3$O$_{13}$PF

Mol. Weight: 1171.85

Physical appearance: brownish liquid

Yield: not determined xv. Synthesis of 19a

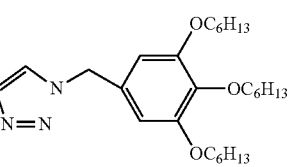

19a

The compound 19a was synthesized using general procedure of example 5.1, starting from 11d (182 mg, 334 mmol), 6c (115 mg, 334 mmol), CuSO₄ (4 mg, 0.016 mmol) sodium ascorbate (6.6 mg, 0.0303 mmol) in THF/water (50:50). The product obtained was purified using reverse phase chromatography using acetonitrile/water followed by chloroform and normal phase chromatography using MeOH/DCM to get brownish liquid (0.215 g, 229 mmol, 60%), $R_f$=0.4 in 5% methanol/DCM.

$^1$H NMR (400 MHz, CDCl₃) $\delta_H$ 7.49 (5, 1H), 6.45 (s, 2H), 5.38 (s, 2H), 4.65 (s, 2H), 3.94-3.86 (m, 6H), 3.91 (m, 6H), 3.74-3.56 (m, 29H), 2.16-2.08 (m, 2H), 1.77-1.67 (m, 6H), 1.49-1.27 (m, 29H), 0.89 (m, 9H)

$^{13}$C NMR (100 MHz, CDCl₃) $\delta_C$ 153.28, 129.39, 106.64, 77.16, 73.30, 70.07, 69.65, 69.09, 65.01, 64.62, 61.54, 54.32, 53.43, 31.63, 31.44, 29.21, 25.62, 22.49, 16.29, 13.91

MALDI-TOF (M+K) 1000.62
Mol. formula: C48H88N3O14P
Mol. Weight: 961.60
Physical appearance: brownish liquid
Yield: 60% xvi. Synthesis of 19b

19b

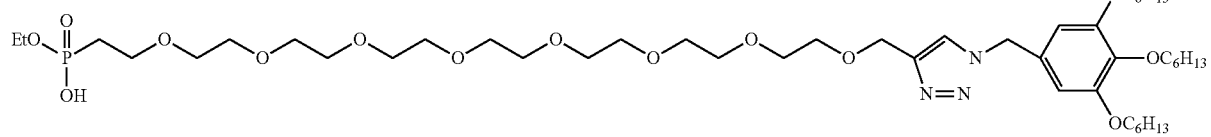

The compound 19b was synthesized using general procedure of example 5.2, starting from 19a (53 mg, 51 mmol), oxalyl chloride (28 mg, 0.114 mmol) in DCM. The Product obtained was taken for next step without further purification.

MALDI-TOF (M+K) 972.63
Mol. formula: $C_{46}H_{84}N_3O_{14}P$
Mol. Weight: 933.56
Physical appearance: brownish liquid
Yield: not determined xvii. Synthesis of 22c [ethyl (1-(1-(3,4,5-tris(hexyloxy)benzyl)-1H-1,2,3-triazol-4-yl)-2,5,8,11,14,17,20,23-octaoxapentacosan-25-yl)phosphonofluoridate] C6-3T 19c

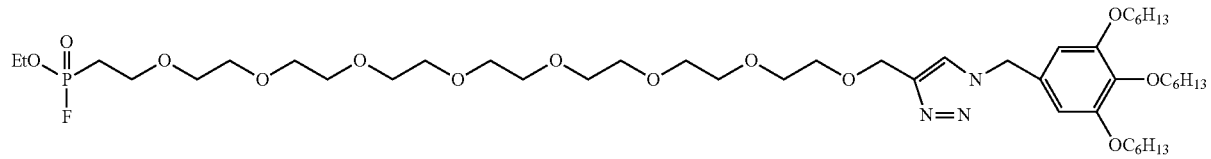

The compound 29c was synthesized using general procedure of example 5.3, starting from 29b (45 mg, 0.0421 mmol), DAST (31 mg, 0.192 mmol) in DCM. The product obtained was used for conjugation without further purification.

$^{19}$F NMR (400 MHz, CDCl₃) $\delta_F$ −59.91, −62.74
MALDI-TOF (M+K) 974.62
Mol. formula: $C_{46}H_{83}N_3O_{14}PF$
Mol. Weight: 935.56
Physical appearance: brownish liquid
Yield: not determined xviii. Synthesis of 20a 20a

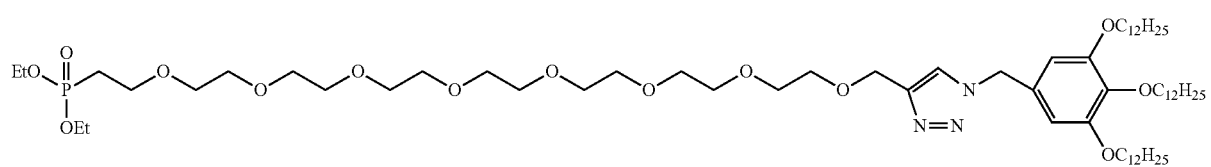

The compound 20a was synthesized using general procedure of example 5.1, starting from 11d (200 mg, 0.378 mmol), 6c (259 mg, 380 mmol), CuSO$_4$ (4.71 mg, 0.0189 mmol), sodium ascorbate (7.5 mg, 0.0378 mmol) in THF/water (50:50). The product obtained was purified using reverse phase chromatography using acetonitrile/water followed by chloroform and normal phase chromatography using MeOH/DCM to get brownish liquid (0.325 g, 2.6 mmol, 71%). R$_f$=0.4, solvent=5% methanol/DCM.

$^1$H NMR (400 MHz, CDCl$_3$) δ$_H$7.46 (s, 1H), 6.45 (s, 2H), 5.37 (s, 2H), 4.65 (s, 2H), 4.14-4.04 (m, 4H), 3.98-3.88 (m, 6H), 3.74-3.56 (m, 31H), 2.16-2.06 (m, 2H), 1.80-1.68 (m, 6H), 1.48-1.38 (m, 6H), 1.33-1.20 (m, 57H), 0.87 (t, J=6.8 Hz, 9H)

$^{13}$C NMR (100 MHz, CDCl$_3$) δ$_C$153.51, 138.52, 129.47, 106.81, 73.50, 70.64, 70.60, 70.54, 70.50, 70.23, 69.81, 69.29, 65.18, 64.79, 61.70, 61.64, 31.99, 30.38, 29.81, 29.79, 29.72, 29.69, 29.66, 29.47, 29.42, 27.73, 26.35, 26.17, 26.14, 22.75, 16.52, 16.45, 14.17

MALDI-TOF (M+K) 1252.84
Mol. formula: C$_{66}$H$_{124}$N$_3$O$_{14}$P
Mol. Weight: 1213.88
Physical appearance: brownish liquid
Yield: 85% xix. Synthesis of 20b

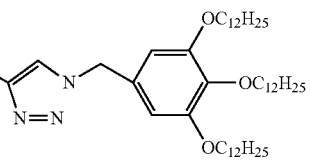

20b

The compound 20b was synthesized using general procedure of example 5.2, starting from 20a (257 mg, 0.211 mmol), oxalyl chloride (136 mg, 0.8447 mmol) in DCM. The Product obtained was taken for next step without further purification.

MALDI-TOF (M+Na) 1208.90
Mol. formula: C$_{64}$H$_{120}$N$_3$O$_{14}$P
Mol. Weight: 1185.85
Physical appearance: brownish liquid
Yield: not determined xx. Synthesis of 23c [ethyl (1-(1-(3,4,5-tris(dodecyloxy)benzyl)-1H-1,2,3-triazol-4-yl)-2,5,8,11,14,17,20,23-octaoxapentacosan-25-yl)phosphonofluoridate] C12-3T

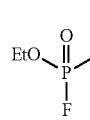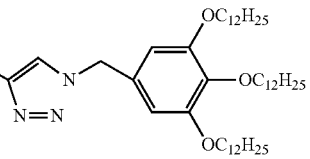

20c

The compound 20c was synthesized using general procedure of example 5.3, starting from 23b (250 mg, 0.210 mmol), DAST (129 mg, 0.801 mmol) in DCM. The Product obtained was used for conjugation without purification.

$^{19}$F NMR (400 MHz, CDCl$_3$) δ$_F$−59.91, −62.74
MALDI-TOF (M+K) 1226.77
Mol. formula: C$_{64}$H$_{119}$N$_3$O$_{14}$PF
Mol. Weight: 1187.84
Physical appearance: brownish liquid
Yield: not determined xxi. Synthesis of 21a

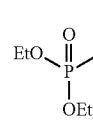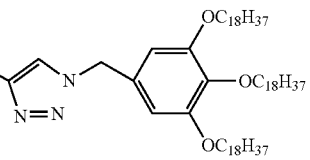

21a

The compound 21a was synthesized using general procedure of example 5.1, starting from 11d (86 mg, 0.162 mmol), 7c (150 mg, 0.163 mmol) in THF/water/DCM (50:25:25), CuSO$_4$ (8.1 mg, 0.0325 mmol), sodium ascorbate (3.2 mg, 0.0162 mmol). The product obtained was purified using reverse phase chromatography using acetonitrile/water followed by chloroform and normal phase chromatography using MeOH/DCM to get brownish liquid (0.195 g, 0.134 mmol, 82%).

R$_f$=0.4, solvent=5% methanol/DCM.

$^1$H NMR (400 MHz, CDCl$_3$) $\delta_H$ 7.48 (s, 1H), 6.44 (s, 2H), 5.37 (s, 2H), 4.64 (s, 2H), 4.12-4.03 (m, 4H), 3.95-3.85 (m, 6H), 3.73-3.59 (m, 32H), 2.17-1.99 (m, 2H), 1.79-1.69 (m, 6H), 1.44-1.24 (m, 100H), 0.86 (t, J=7.2 Hz, 9H)

$^{13}$C NMR (100 MHz, CDCl$_3$) $\delta_C$: 153.66, 138.54, 129.50, 106.83, 77.16, 73.48, 70.64, 70.58, 70.54, 70.27, 69.84, 69.33, 65.22, 64.81, 61.76, 54.56, 53.54, 32.03, 30.43, 29.86, 29.83, 29.76, 29.72, 29.47, 27.76, 26.38, 26.20, 22.79, 16.56, 16.50, 14.22

MALDI-TOF (M+K) 1505.23

Mol. formula: C$_{84}$H$_{160}$N$_3$O$_{14}$P

Mol. Weight: 1466.16

Physical appearance: brownish liquid

Yield: 82% xxii. Synthesis of 21b

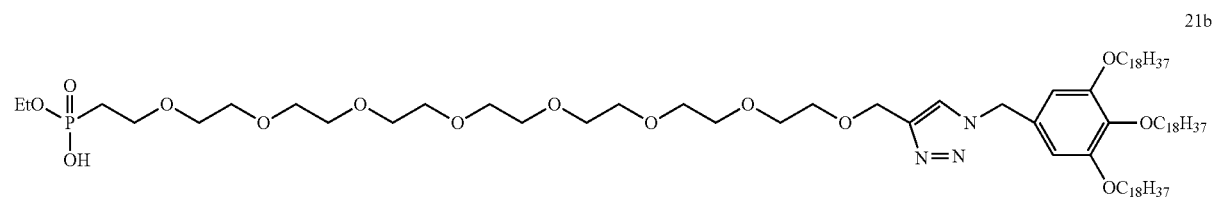

The compound 21b was synthesized using general procedure of example 5.2, starting from 21a (0.195 g, 0.134 mmol), oxalyl chloride (0.085 g, 0.527 mmol) in DCM. The product obtained was taken for next step without further purification.

MALDI-TOF (M+K) 1477.21

Mol. formula: C$_{82}$H$_{156}$N$_3$O$_{14}$P

Mol. Weight: 1438.13

Physical appearance: brownish liquid

Yield: not determined xxiii. Synthesis of 24c [ethyl (1-(1-(3,4,5-tris(octadecyloxy)benzyl)-1H-1,2,3-triazol-4-yl)-2,5,8,11,14,17,20,23-octaoxapentacosan-25-yl)phosphonofluoridate] C18-3T

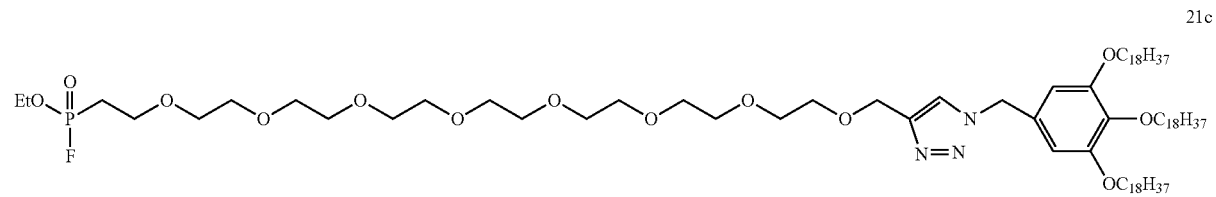

The compound 21c was synthesized using general procedure of example 5.3, starting from 21b (0.176 g, 0.122 mmol), DAST (0.078 mg, 0.469 mmol), in DCM. The product obtained was used for conjugation without purification.

$^{19}$F NMR (377 MHz, CDCl$_3$) $\delta_F$ −59.91, −62.74

MALDI-TOF (M+K) 1479.10

Mol. formula: C$_{82}$H$_{155}$N$_3$O$_{14}$PF

Mol. Weight: 1440.12

Physical appearance: brownish liquid

Yield: not determined

B. Synthesis of Intermediates for Spacer Variant AABPs.

i. Synthesis of Compound 22a

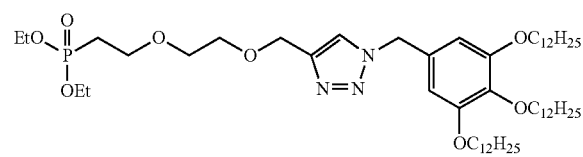

The compound 22a was synthesized using general procedure 5.1, starting from 9d (0.100 g, 0.395 mmol), 7c (0.271 g, 0.396 mmol), CuSO$_4$ (3.1 mg, 0.019 mmol), sodium ascorbate (7.8 mg, 0.040 mmol) in THF/water (50:50). The crude product obtained was purified using reverse phase column chromatography using ACN/water followed by chloroform and normal phase column chromatography using MeOH/DCM to get brownish liquid (0.250 g, 0.250 mmol, 68%), R$_f$=0.4 in 5% MeOH/DCM.

$^1$H NMR (400 MHz, CDCl$_3$): $\delta_H$ 7.49 (s, 1H), 6.46 (s, 2H), 5.38 (s, 2H), 4.65 (s, 2H), 4.17-4.00 (m, 4H), 3.95-3.90 (m, 6H), 3.75-3.50 (m, 5H), 2.15-2.03 (m, 2H), 184-1.68 (m, 13H), 1.54-1.19 (m, 62H), 0.87 (t, J=6.8 Hz, 9H).

$^{13}$C NMR (100 MHz, CDCl$_3$): $\delta_C$ 153.79, 138.75, 129.55, 107.01, 77.16, 73.68, 70.39, 69.86, 69.51, 65.32, 64.95, 61.84, 54.71, 32.14, 30.53, 29.85, 29.63, 27.87, 26.33, 22.90, 16.53, 14.33.

MALDI-TOF MS (M+K): 988.33.

Mol. formula: C$_{54}$H$_{100}$N$_3$O$_{18}$P

Mol. Weight: 949.72

Physical appearance: brownish liquid

Yield: 68% ii. Synthesis of Compound 22b

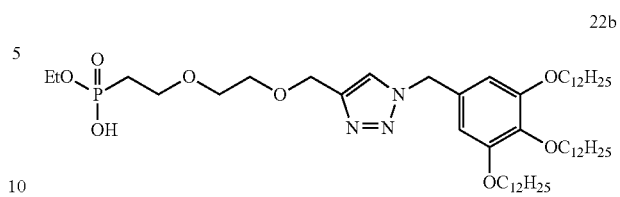

The compound 22b was synthesized using general procedure 5.2, starting from 22a (100 mg, 0.10 mmol), oxalyl chloride (49 mg, 0.42 mmol) in DCM. The product was carried to next step without purification.

$^1$H NMR (400 MHz, CDCl$_3$): $\delta_H$ 7.52 (s, 1H), 6.46 (s, 2H), 5.33 (s, 2H), 4.64 (s, 2H), 4.09-4.00 (m, 4H), 3.91-3.83 (m, 6H), 3.72-3.51 (m, 5H), 2.15-2.03 (m, 2H), 178-1.68 (m, 13H), 1.44-1.12 (m, 55H), 0.85 (t, J=6.8 Hz, 9H).

MALDI-TOF MS (M+K): 960.32.

Mol. formula: C$_{52}$H$_{96}$N$_3$O$_8$P

Mol. Weight: 921.69

Physical appearance: pale yellow liquid

Yield: not determined iii. Synthesis of Compound 22c [Ethyl (2-(2-((1-(3, 4,5-tris(dodecyloxy)benzyl)-1H-1,2,3-triazol-4-yl) methoxy)ethoxy)ethyl)phosphonofluoridate] DEG-C12-3T

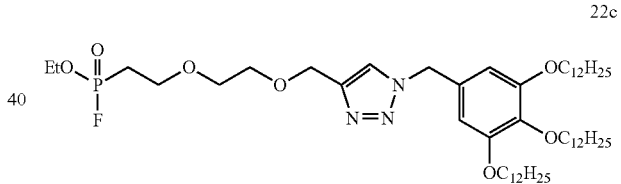

The compound 22c was synthesized using general procedure 5.3, starting from 22b (80 mg, 0.08 mmol), DAST (50 mg, 0.34 mmol) in DCM. The product was used for modification without further purification.

$^{19}$F NMR (400 MHz, CDCl$_3$) $\delta_F$ −59.91, −62.74.

MALDI-TOF MS (M+Na): 946.78.

Mol. formula: C$_{52}$H$_{95}$N$_3$O$_{12}$PF

Mol. Weight: 923.77

Physical appearance: brownish liquid

Yield: not determined iv. Synthesis of Compound 23a

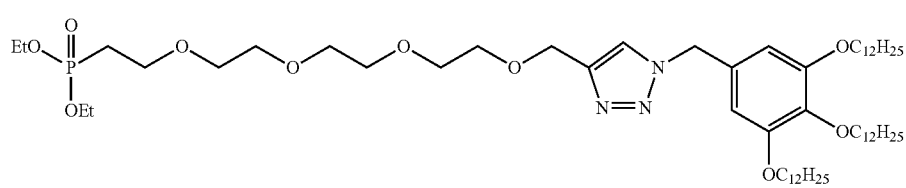

The compound 23a was synthesized using general procedure 5.1, starting from 10d (0.25 g, 0.70 mmol), 7c (0.50 g, 0.70 mmol), CuSO$_4$ (0.036 g, 0.1 mmol), sodium ascorbate (0.014 g, 0.070 mmol) in THF/water (50:50). The crude product obtained was purified using reverse phase column chromatography using ACN/water followed by chloroform and normal phase column chromatography using MeOH/DCM to get brownish liquid (0.33 g, 0.30 mmol, 62%), $R_f$=0.4 in 5% MeOH/DCM.

$^1$H NMR (400 MHz, CDCl$_3$): $\delta_H$ 7.47 (s, 1H), 6.45 (s, 2H), 5.37 (s, 2H), 4.65 (s, 2H), 4.13-4.04 (m, 4H), 3.93-3.89 (q, J=8 Hz, 6H), 3.74-3.56 (m, 15H), 2.15-2.07 (m, 2H), 1.80-1.70 (m, 10H), 1.45-1.25 (m, 68H), 0.87 (t, J=8 Hz, 9H).

$^{13}$C NMR (100 MHz, CDCl$_3$): $\delta_C$ 153.74, 145.65, 138.86, 129.44, 122.56, 106.97, 77.16, 73.53, 70.73, 70.61, 70.32, 69.92, 69.43, 65.28, 64.80, 61.81, 61.74, 54.64, 32.08, 30.48, 29.90, 29.86, 29.79, 29.58, 29.44, 27.84, 26.46, 26.24, 22.84, 16.61, 16.55, 14.26.

MALDI-TOF MS (M+K): 1,076.79.
Mol. formula: C$_{58}$H$_{108}$N$_3$O$_{10}$P
Mol. Weight: 1037.78
Physical appearance: brownish liquid
Yield: 62% v. Synthesis of Compound 23b

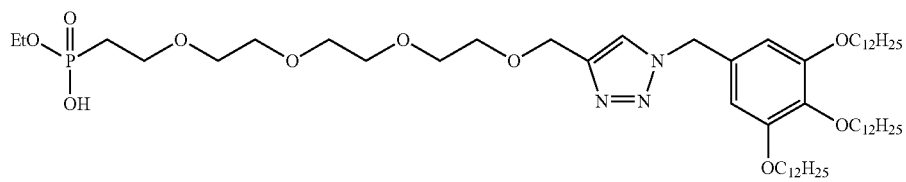

Mol. formula: C$_{56}$H$_{104}$N$_3$O$_{10}$P
Mol. Weight: 1009.75
Physical appearance: pale yellow liquid
Yield: not determined The compound 23b was synthesized using general procedure 5.2, starting from 23a (0.296 g, 0.28 mmol), oxalyl chloride (0.14 g, 1.1 mmol) in DCM. The product was carried to next step without purification.

$^1$H NMR (400 MHz, CDCl$_3$): $\delta_H$ 7.50 (s, 1H), 6.49 (s, 2H), 5.40 (s, 2H), 4.60 (s, 2H), 4.12-4.03 (m, 2H), 3.94-3.91 (q, J=8 Hz, 6H), 3.81-3.62 (m, 15H), 2.15-2.05 (m, 2H), 1.82-1.69 (m, 10H), 1.47-1.27 (m, 68H), 0.89 (t, J=8 Hz, 9H).

MALDI-TOF MS (M+K): 1048.84.
Mol. formula: C$_{56}$H$_{104}$N$_3$O$_{10}$P
Mol. Weight: 1009.75
Physical appearance: pale yellow liquid
Yield: not determined vi. Synthesis of Compound 23c [ethyl (1-(1-(3,4,5-tris(dodecyloxy)benzyl)-1H-1,2,3-triazol-4-yl)-2,5,8,11-tetraoxatridecan-13-yl)phosphonofluoridate]
TEG-C12-3T

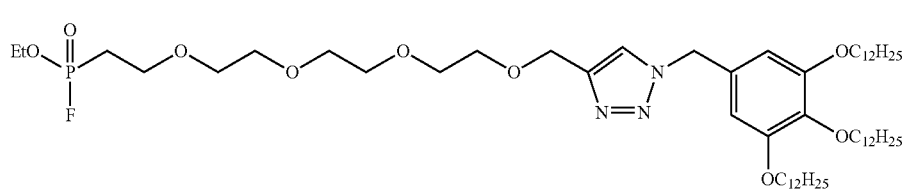

The compound 23c was synthesized using general procedure 5.3, starting from 23b (0.17 g, 0.10 mmol), DAST (0.11 g, 0.6 mmol) in DCM. The product was used for modification without further purification.

$^{19}$F NMR (400 MHz, CDCl$_3$): $\delta_F$ −59.91, −62.74.
MALDI-TOF MS (M+Na): 1,034.88
Mol. formula: C$_{56}$H$_{103}$N$_3$O$_9$PF
Mol. Weight: 1011.74
Physical appearance: brownish liquid
Yield: not determined vii. Synthesis of Compound 24a

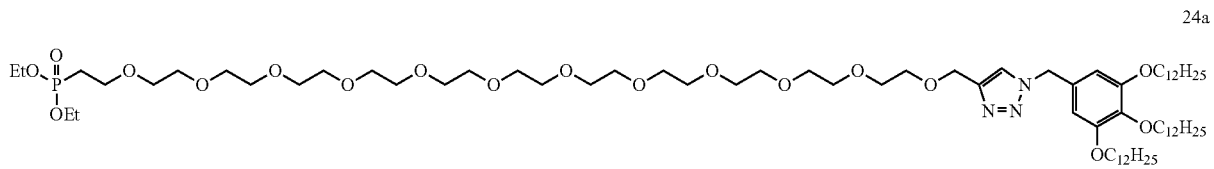

24a

The compound 24a was synthesized using general procedure 5.1, starting from 12a (0.150 g, 0.21 mmol), 7c (0.219 g, 0.31 mmol), CuSO$_4$ (0.010 mg, 0.040 mmol), sodium ascorbate (0.004 mg, 0.020 mmol) in THF/water (50:50). The crude product obtained was purified using reverse phase column chromatography using ACN/water followed by chloroform and normal phase column chromatography using MeOH/DCM to get brownish liquid (0.168 g, 0.12 mmol, 57%), R$_f$=0.4 in 5% MeOH/DCM.

$^1$H NMR (400 MHz, CDCl$_3$): $\delta_H$ 7.48 (s, 1H), 6.44 (s, 2H), 5.36 (s, 2H), 4.64 (s, 2H), 4.10-4.03 (m, 4H), 3.88 (q, J=8 Hz, 6H), 3.73-3.57 (m, 55H), 2.15-2.06 (m, 2H), 1.80-1.66 (m, 13H), 1.48-1.23 (m, 74H), 0.85 (t, J=8 Hz, 9H).
$^{13}$C NMR (100 MHz, CDCl$_3$) $\delta_c$ 153.65, 138.49, 129.49, 122.61, 106.79, 77.16, 73.56, 72.79, 70.30, 69.84, 69.31, 64.81, 61.75, 54.57, 32.03, 30.41, 29.85, 29.81, 29.75, 29.49, 29.47, 26.19, 22.80, 14.23.
MALDI-TOF MS (M+K): 1,429.61.
Mol. formula: C$_{74}$H$_{140}$N$_3$O$_{18}$P
Mol. Weight: 1390.99
Physical appearance: brownish liquid
Yield: 57% viii. Synthesis of Compound 24b

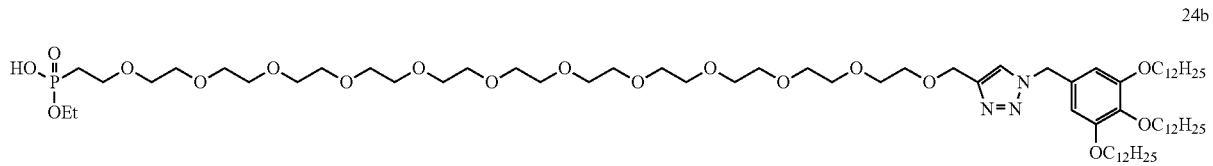

24b

The compound 24b was synthesized using general procedure 5.2, starting from 24a (45 mg, 0.0437 mmol), oxalyl chloride (22 mg, 0.170 mmol) in DCM. The product was carried to next step without purification;

$^1$H NMR (400 MHz, CDCl$_3$): $\delta_H$ 7.50 (s, 1H), 6.46 (s, 2H), 5.38 (s, 2H), 4.66 (s, 2H), 4.14-4.06 (m, 2H), 3.90 (q, J=8 Hz, 6H), 3.78-3.63 (m, 55H), 2.16-2.08 (m, 2H), 1.80-1.68 (m, 13H), 1.44-1.26 (m, 74H), 0.87 (t, J=8 Hz, 9H).
MALDI-TOF MS (M+K): 1,400.60.
Mol. formula: C$_{72}$H$_{136}$N$_3$O$_{18}$P
Mol. Weight: 1361.66
Physical appearance: pale yellow liquid
Yield: not determined ix. Synthesis of Compound 24c [ethyl (1-(1-(3,4,5-tris(dodecyloxy)benzyl)-1H-1,2,3-triazol-4-yl) 2,5,8,11,14,17,20,23,26,29,32,35-dodecaoxaheptatriacontan-37-yl)phosphonofluoridate] DDEG-C12-3T

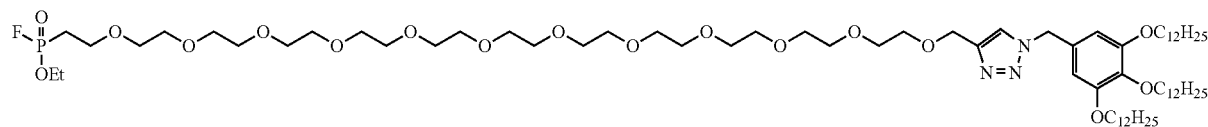
24c

The compound 24c was synthesized using general procedure 5.3, starting from 24b (44 mg, 0.0437 mmol), DAST (257 mg, 0.159 mmol) in DCM. The product was used for modification without further purification.

$^{19}$F NMR (400 MHz, CDCl$_3$): $\delta_F$ −59.91, −62.74.
MALDI-TOF MS (M+K): 1402.68.
Mol. formula: $C_{72}H_{135}N_3O_{17}PF$
Mol. Weight: 1363.66
Physical appearance: brownish liquid
Yield: not determined x. Synthesis of Compound 25a

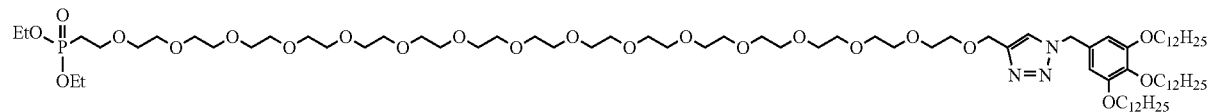
25a

The compound 21a was synthesized using general procedure 5.1, starting from 13d (0.17 g, 0.19 mmol), 7c (0.16 g, 0.23 mmol), CuSO$_4$ (0.009 g, 0.03 mmol), sodium ascorbate (0.003 mg, 0.01 mmol) in THF/water (50:50). The crude product obtained was purified using reverse phase column chromatography using ACN/water followed by chloroform and normal phase column chromatography using MeOH/DCM to get brownish liquid (0.14 g, 0.09 mmol, 48%), R$_f$=0.4 in 5% MeOH/DCM.

$^1$H NMR (400 MHz, CD$_3$OD): $\delta_H$ 7.96 (s, 1H), 6.60 (m, 3H), 5.47 (s, 2H), 4.60 (s, 2H), 4.12-4.05 (m, 4H), 3.94-3.86 (m, 6H), 3.72-3.56 (m, 36H), 3.29-3.27 (m, 13H), 2.16-2.08 (m, 2H), 1.78-1.65 (m, 6H), 1.51-1.27 (m, 68H), 0.88 (t, J=8 Hz, 9H).

$^{13}$C NMR (100 MHz, MeOD$_4$): $\delta_C$ 154.67, 125.14, 124.54, 107.55, 74.44, 71.69, 71.63, 71.57, 71.54, 71.28, 70.78, 70.01, 49.00, 33.15, 30.99, 30.91, 30.87, 30.81, 30.59, 30.57, 27.39, 23.80, 14.52.

MALDI-TOF MS (M+K): 1,604.78.
Mol. formula: $C_{82}H_{156}N_3O_{22}P$
Mol. Weight: 1565.69

Physical appearance: brownish liquid
Yield: 48% xi. Synthesis of Compound 25b

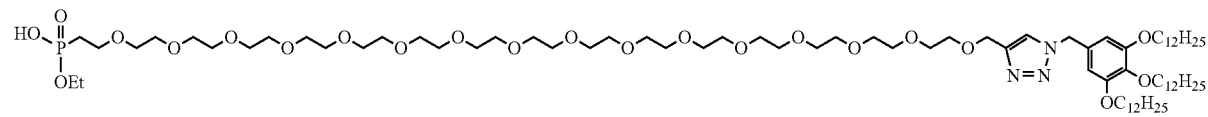
25b

The compound 25b was synthesized using general procedure 5.2, starting from 25a (0.145 g, 0.09 mmol), oxalyl chloride (0.071 g, 0.5 mmol) in DCM. The product was carried to next step without purification.

$^1$H NMR (400 MHz, CD$_3$OD): $\delta_H$ 7.96 (s, 1H), 6.59 (m, 3H), 5.46 (s, 2H), 4.60 (s, 2H), 3.93-3.86 (m, 2H), 3.78-3.69 (m, 6H), 3.61-3.56 (m, 36H), 3.29-3.27 (m, 13H), 2.37-2.30 (m, 2H), 1.77-1.65 (m, 6H), 1.50-1.11 (m, 68H), 0.87 (t, J=8 Hz, 9H).

MALDI-TOF MS (M+K): 1,578.69.
Mol. formula: $C_{80}H_{152}N_3O_{22}P$
Mol. Weight: 1538.67
Physical appearance: pale yellow liquid
Yield: not determined x. Synthesis of Compound 25c [ethyl (1-(1-(3,4,5-tris(dodecyloxy)benzyl)-1H-1,2,3-triazol-4-yl)-2,5,8,11,14,17,20,23,26,29,32,35,38,41,44,47-hexadecaoxanonatetracontan-49-yl)phosphonofluoridate] CEG-C12-3T ii. Instrumental Parameters for Measuring Molecular Weight of the Protein

The samples were analysed in Linear High Mass mode in AB Sciex 4800 plus MALDI-TOF TOF/TOF Analyser with 4000 Series Explorer as software. Laser intensity maintained at 7900 and mass was scanned between 10000 and 40000 with focus mass at 25000 Da.

25c

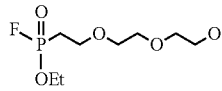
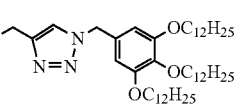

The compound 25c was synthesized using general procedure 5.3, starting from 25b (44 mg, 0.0437 mmol), DAST (257 mg, 0.159 mmol) in DCM. The product was used for modification without further purification.

$^{19}$F NMR (400 MHz, CD$_3$OD): $\delta_F$ −59.91, −62.74;
MALDI-TOF MS (M+K): 1,580.56.
Mol. formula: C$_{80}$H$_{151}$N$_3$O$_{21}$PF
Mol. Weight: 1541.10
Physical appearance: brownish liquid
Yield: not determined

Example 9: Molecular Weight Determination of Protein and Conjugate

Proteins were purchased from commercial vendors and accurate molecular weights were determined using 2,5-Dihydroxyacetophenone (DHAP) and diammoniumhydrogencitrate (DAHC) as matrix using the following procedure. All the stages of protein conjugation and purification were also followed by MALDI-TOF.

i. General Procedure 3.5 mg of DHAP and 4.5 mg of DHAC were weighed separately in micro centrifuge tubes. 500 µL of Milli-Q water and 150 µL of ethanol were added to each tube, respectively. Both the solutions were sonicated for 1 minute and vortexed for another minute. Then 50 µL of DHAC solution was transferred to DHAP solution and the resulting matrix mixture was vortexed for another minute. In a 500 µL micro centrifuge tube, 1:1:1 ratio of protein solution, 2% triflouroacetic acid (TFA) and final matrix mixture were mixed and vortexed for 1 minute. The final matrix mixture containing protein was then kept undisturbed and when the crystallization was observed in centrifuge tubes, 1-2 µL of the samples were spotted on the plate and air dried for 10-15 minutes. The plate was loaded on to instrument and fired to get accurate molecular weight both in +1 and +2 states. 100 µM protein concentration was found to be optimum for MALDI-TOF analysis.

iii. Molecular Weight Determination of Trypsin

4 µL of 100 µM trypsin was mixed with 4 µL of 2% TFA (trifluoro acetic acid) and 4 µL of matrix mixture as previously stated, vortexed and spotted on MALDI-ToF plate. After air drying, plate was loaded and monitored with parameters as mentioned above, to get accurate molecular weight of trypsin. For the native protein, the molecular weight was found to be 23272. This weight slightly varied with the conditions and progress of the reactions. Our matrix system allowed us to get accurate molecular weights and these weights were in agreement with the molecular weights obtained from ESI-MS, protein intact-direct mode.

iv. Conjugation Monitoring Using MALDI-ToF

Monitoring the extent of conjugation was done by removing aliquots, using the procedure mentioned for monitoring native proteins using MALDI-ToF. The change in molecular weight of native is shown in Tables 1 to 3 below.

Example 10: Protein Modification and Monitoring Using MALDI-ToF i. General Procedure

The final concentration of protein in the reaction mixture was maintained as 100 µM which was optimum for MALDI-ToF, rendering time to time monitoring of conjugation reaction possible. Triton X-100 was used to solubilise the AABPs. 2% (about 100 times more than critical micelle concentration (CMC)) was found to be optimum in the final mixture. The reaction was kept on rotospin and allowed to react at 20 rpm at 25° C. When the conjugate intensity remains same (typically within 24 hours), the reaction mixture were directly triton removed using IEX without any further work-up.

ii. Specific Procedure

According to the obtained molecular weight, 2.3 mg of trypsin was weighed in a micro centrifuge tube and vortexed with 500 µL of 50 mM sodium phosphate buffer pH 7.4 for 5-10 minutes to get 200 µM solutions. 10 equivalents of amphiphilic activity based probe (AABP) was weighed in a centrifuge tube and 20 µL of triton X-100 was added and vortexed with 500 µl of 50 mM sodium phosphate buffer pH 7.4, till the mixture becomes homogenous. To the AABP mixture, protein solution was added resulting in 100 µM of protein solution with 2% triton X-100 and allowed to react on rotospin. Only in case of C18 (only for 2T and 3T) AABP, soon after the addition of triton X-100, the mixture was homogenised using sonication, then 50 mM sodium phosphate buffer pH 7.4 was added and vortexed to get clear solution. 200 µL of triton X-100 was used instead of 2 µL, only in case of C18-3T probe, in order to solubilise properly.

Example 11: Synthesis of Serine Protease-OEG-C12-3T Hydrophobin Mimics (Varying Heads)

Figure 1A:
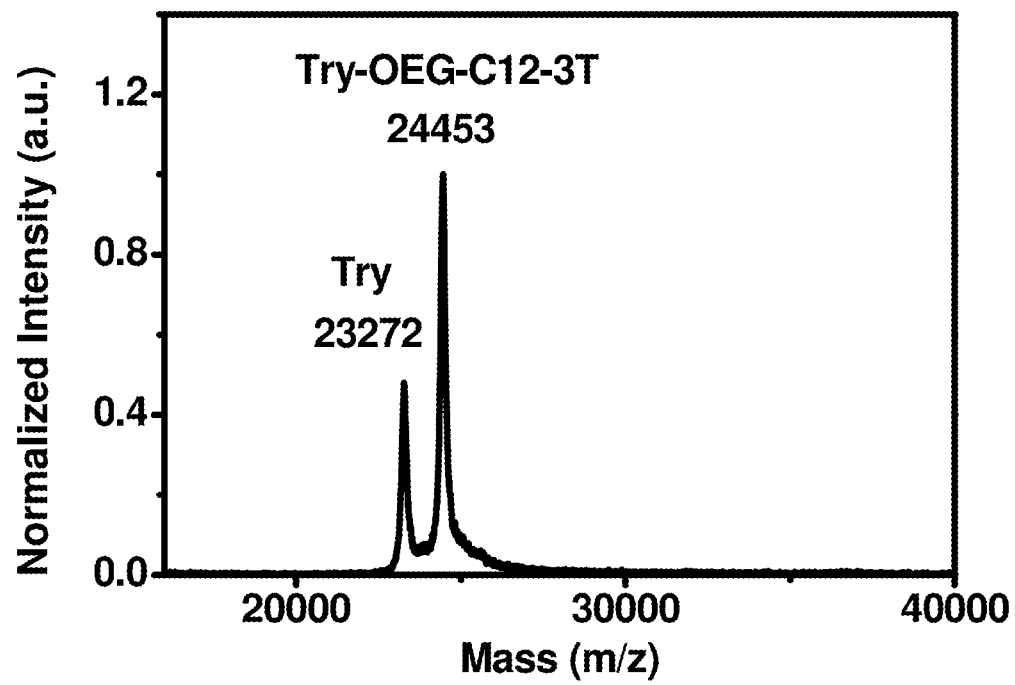
FIGS. 1A, 1B, 1C, and 1D depict MALDI-TOF spectra of serine proteases and their corresponding hydrophobin mimic reaction mixtures FIGS. 2.1A to 2.1D, 2.2A to 2.2D, and 2.3A to 2.3D depict MALDI-TOF spectra of trypsin hydrophobin mimic reaction mixtures
Figure 1B:
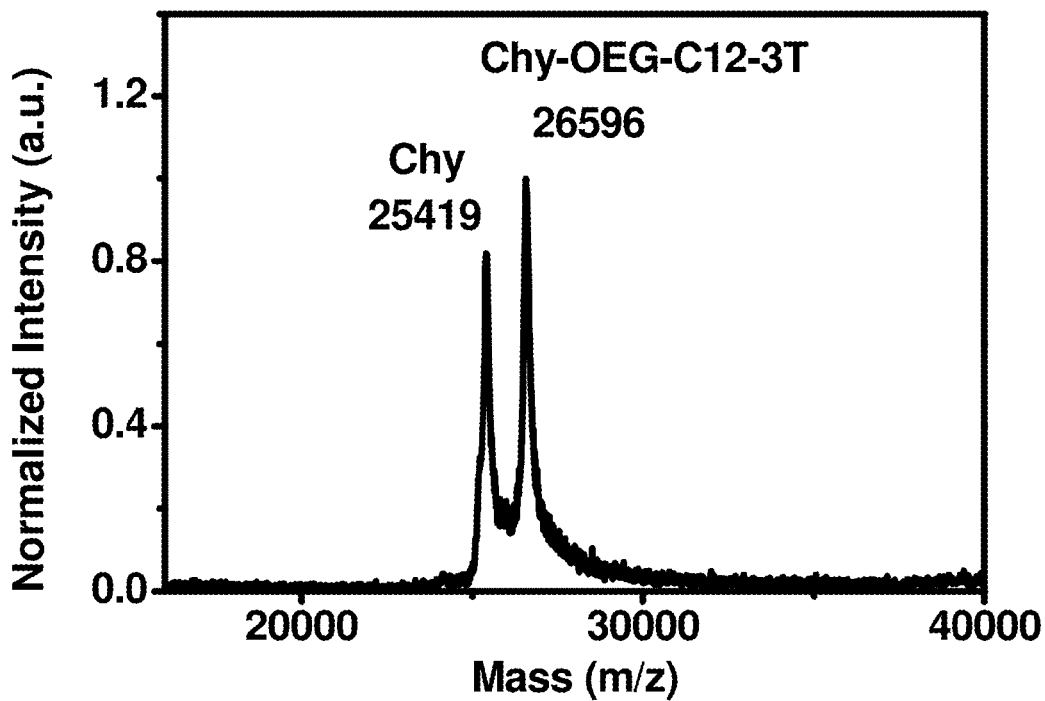

Serine protease was weighed in micro centrifuge tube and 50 mM sodium phosphate pH 7.4 was added quickly and mixed gently with pipette to make 200 µM solutions. Then AABP-OEG-C12-3T was weighed in another micro centrifuge tube, triton X-100 and 50 mM sodium phosphate were added and vortexed for 15 minutes to make a clear solution. Then protein solution was added to this clear AABP solution to get a 100 µM protein solution. The reaction mixture was then kept on rotospin and allowed to react at 20 rpm at 25° C. as explained above. In order to explore the scope of technology and to vary the head of the hydrophobin mimics systematically, we used four different serine proteases (trypsyin, chymotrypsin, subtilisin, proteinase K)

i. Synthesis of Chymotrypsin-OEG-C12-3T Hydrophobin Mimic 2.5 mg of chymotrypsin was weighed in a micro centrifuge tube and mixed gently with 500 µL of 50 mM sodium phosphate buffer pH 7.4 for 10 minutes to get 200 µM solution. 10 equivalents of AABP-OEG-C12-3T (1.1 mg of 20c) was weighed in a centrifuge tube and 20 µL of triton X-100 was added first followed by 500 µL of 50 mM sodium phosphate pH 7.4 and vortexed for 15 minutes. Now to the AABP mixture, protein solution was added and allowed to react on rotospin. Monitoring the extent of modification was done by removing aliquots, using the procedure mentioned above. The formation of corresponding hydrophobin mimic can be seen as a new peak in MALDI-TOF MS spectrum (FIG. 1B). The process is shown in Scheme 5, where a chymotrypsin moiety is depicted as CHYM.

Scheme 5

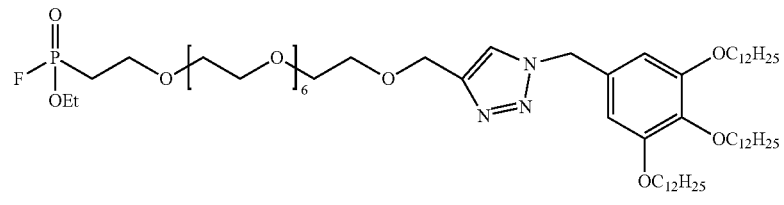

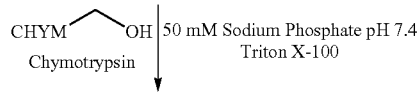

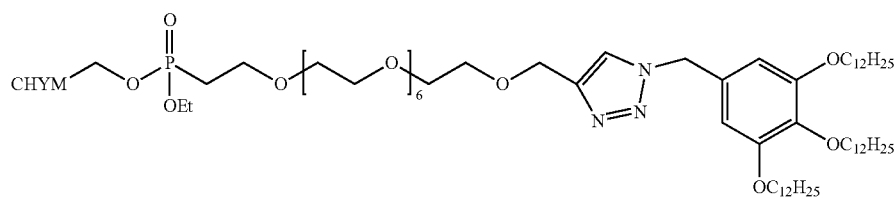

Figure 1C:
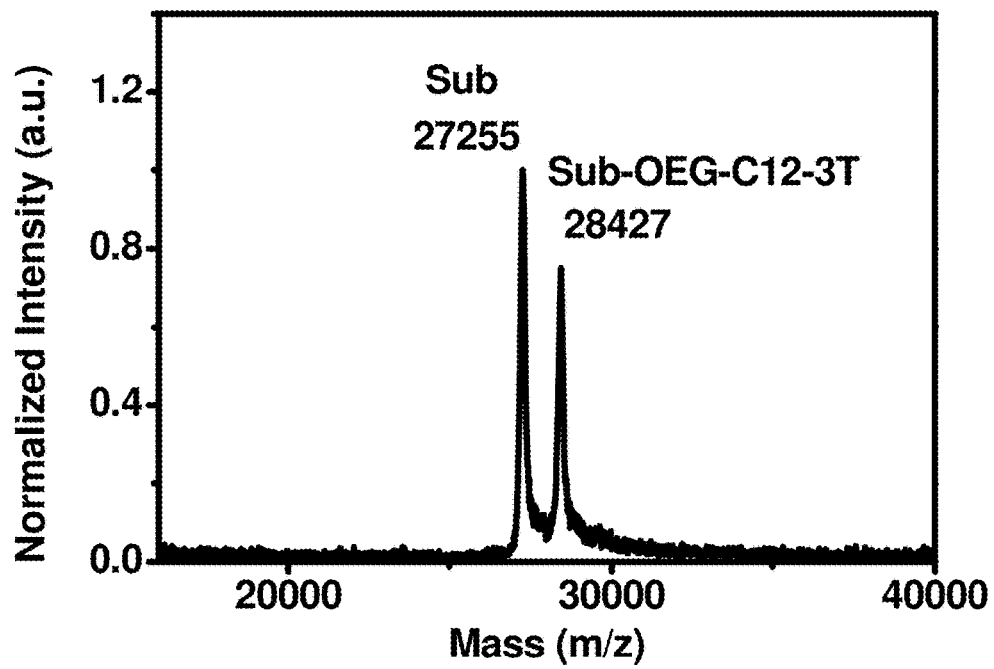

Chymotrypsin-OEG-C12-3T ii. Synthesis of Subtilisin-OEG-C12-3T Hydrophobin Mimic 2.7 mg of subtilisin was weighed in a micro centrifuge tube and mixed gently with 500 μL of 50 mM sodium phosphate pH 7.4 for 10 minutes to get 200 μM solution. 10 equivalents of AABP-OEG-C12-3T (1.1 mg of 20c) was weighed in a centrifuge tube and 20 μL of triton X-100 was added first followed by 500 μL of 50 mM sodium phosphate pH 7.4. Then the mixture was vertexed for 15 minutes. Now to the AABP mixture, protein solution was added and allowed to react on rotospin. Monitoring the extent of modification was done by removing aliquots and analyzed using MALDI-TOF MS. The formation of corresponding hydrophobin mimic can be seen as a new peak in MALDI-TOF MS spectrum (FIG. 1C). The process is shown in Scheme 6, where a subtilisin moiety is depicted as SUBT.

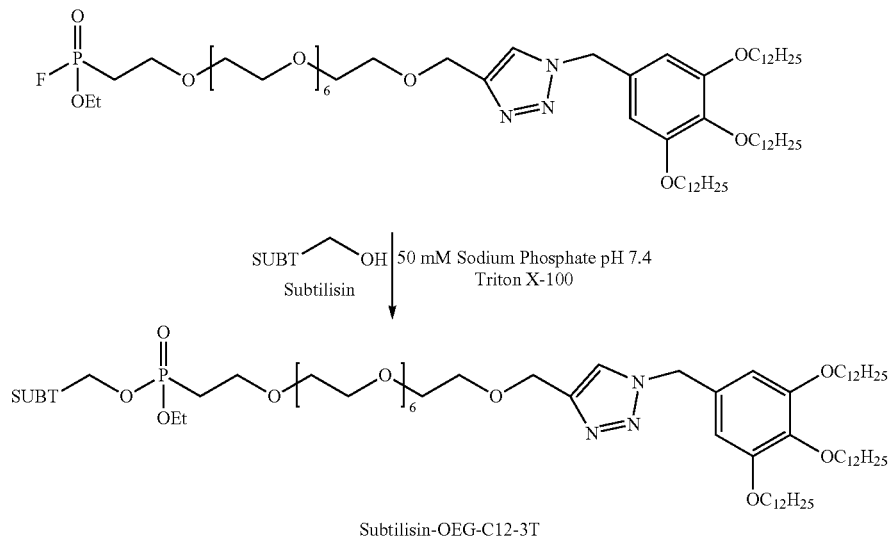

Figure 1D:
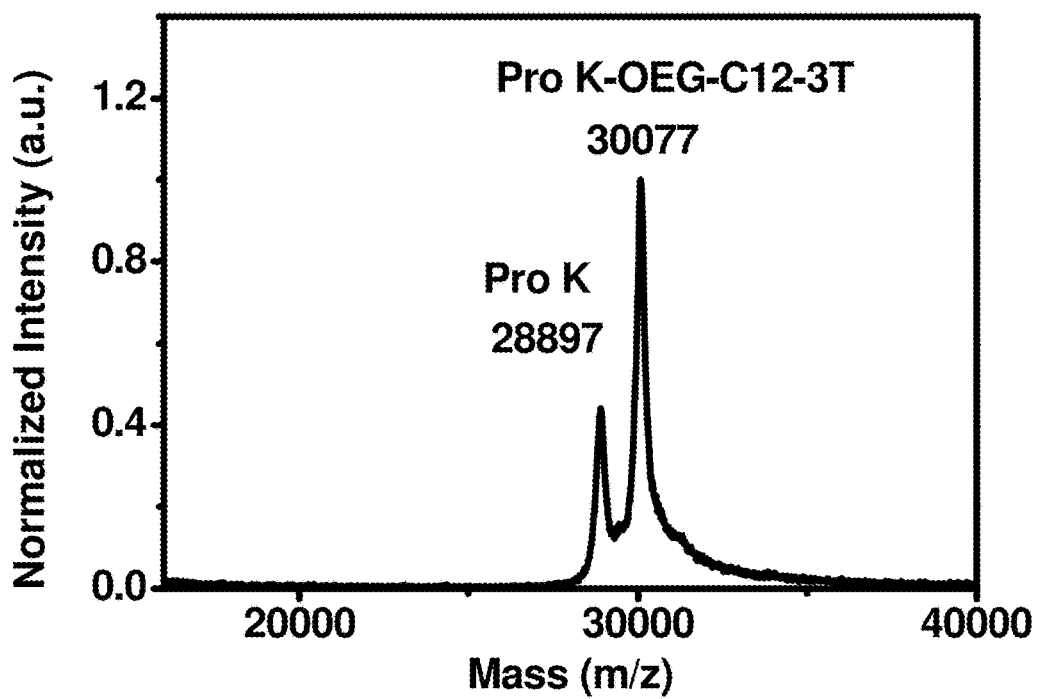

Scheme 6 iii. Synthesis of Proteinase K-OEG-C12-3T Hydrophobin Mimic 2.9 mg of proteinase K was weighed in a micro centrifuge tube and mixed gently with 500 μL of 50 mM sodium phosphate pH 7.4 for 10 minutes to get 200 μM solution. 10 equivalents of AABP-OEG-C12-3T (1.1 mg of 20c) was weighed in a centrifuge tube and 20 μL of triton X-100 was added first followed by 500 μL of 50 mM sodium phosphate pH 7.4 and vortexed for 15 minutes. To the AABP mixture, protein solution was added and allowed to react on rotospin. Monitoring the extent of modification was done using MALDI-TOF MS as mentioned above. The formation of corresponding hydrophobin mimic can be seen as a new peak in MALDI-TOF MS spectrum (FIG. 1D). The process is shown in Scheme 7, where a proteinase K moiety is depicted as PROK.

Scheme 7

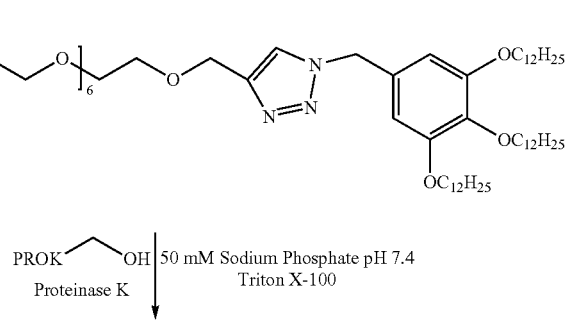

-continued

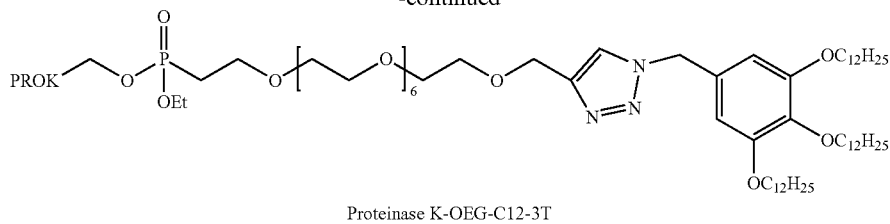

Proteinase K-OEG-C12-3T iv. Synthesis of Trypsin-OEG-C12-3T Hydrophobin Mimic 2.3 mg of trypsin was weighed in a micro centrifuge tube and mixed gently with 500 µL of 50 mM sodium phosphate pH 7.4 for 10 minutes to get 200 µM solution. 10 equivalents of AABP-OEG-C12-3T (1.1 mg of 20c) was weighed in a centrifuge tube and 20 µL of triton X-100 was added first followed by 500 µL of 50 mM sodium phosphate pH 7.4 and vertexed for 15 minutes. Now to the AABP mixture, protein solution was added and allowed to react on rotospin. Monitoring the extent of modification was done by removing aliquots The formation of corresponding hydrophobin mimic can be seen as a new peak in MALDI-TOF MS spectrum (FIG. 1A). The process is shown in Scheme 8 below, where a trypsin moiety is depicted as TRYP.

Scheme 8

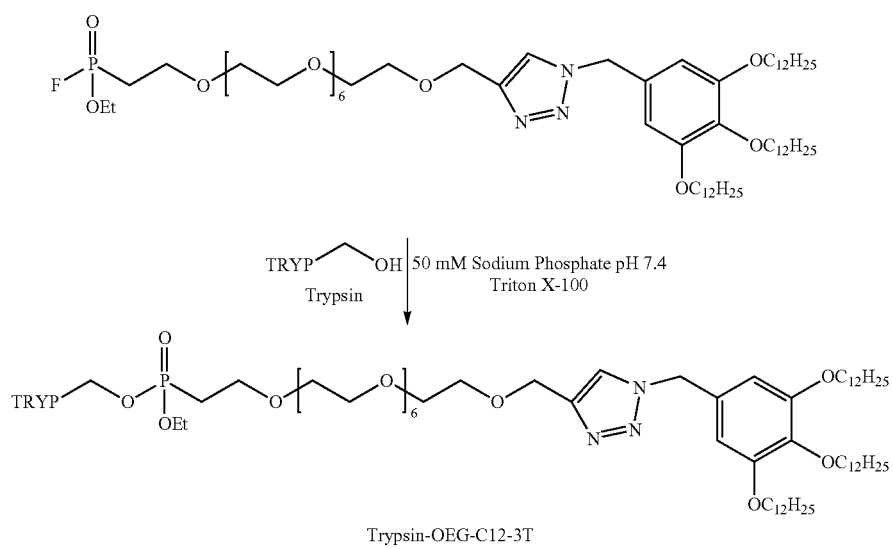

Trypsin-OEG-C12-3T

TABLE 1

MALDI-TOF MS data of serine protease-OEG-C12-3T hydrophobin mimics

| Mw of native protein (Da) | Mw of AABP-OEG-C12-3T (Da) | Mw of hydrophobin mimics calculated (Da) | Mw of hydrophobin mimics obtained (Da)[#] |
|---|---|---|---|
| Proteinase K (28,909) | 1,188.64 | 30,097 | 30,068 ± 10.54 |
| Subtilisin (27,294) | 1,188.64 | 28,482 | 28,425 ± 8.96 |

TABLE 1-continued

MALDI-TOF MS data of serine protease-OEG-C12-3T hydrophobin mimics

| Mw of native protein (Da) | Mw of AABP-OEG-C12-3T (Da) | Mw of hydrophobin mimics calculated (Da) | Mw of hydrophobin mimics obtained (Da)[#] |
|---|---|---|---|
| Chymotrypsin (25,425) | 1,188.64 | 26,613 | 26,579 ± 21.95 |
| Trypsin (23,272) | 1,188.64 | 24,483 | 24,453 ± 13.91 |

[#]Average of >10 individual recording

Example 12: Synthesis of Trypsin-OEG-1/2/3-Tail Hydrophobin Mimics (Varying Tails)

Trypsin was weighed in micro centrifuge tube and 50 mM sodium phosphate pH 7.4 was added quickly and mixed gently with pipette to make 200 µM solutions. Then AABPs were weighed in another micro centrifuge tube, triton X-100 and 50 mM sodium phosphate were added and vortexed for 15 minutes to make a clear solution. Then protein solution was added to this clear AABP solution to get a 100 µM protein solution. The reaction mixture was then kept on rotospin and allowed to react at 20 rpm at 25° C. as explained above. In order to vary the hydrophobic tails of the hydrophobin mimics systematically, we modified trypsin with different hydrophobicities like 2-tails or 3-tails of C6, C12, C18 alkyl chain lengths so as to explore the effect of length as well as volume of the hydrophobic tail.

i. Synthesis of Trypsin-OEG-C12-1T Hydrophobin Mimic 2.3 mg of trypsin was weighed in a micro centrifuge tube and mixed gently with 500 μL of 50 mM sodium phosphate pH 7.4 for 10 minutes to get 200 μM solution. 10 equivalents of AABP-OEG-C12-1T (14c) was weighed in a centrifuge tube and 20 μL of triton X-100 was added first followed by 500 μL of 50 mM sodium phosphate pH 7.4 and vertexed for 15 minutes. Now to the AABP mixture, protein solution was added and allowed to react on rotospin. The formation of corresponding hydrophobin mimic can be seen as a new peak in MALDI-TOF MS spectrum (FIG. 2.2A). The process is depicted in Scheme 9 below, where a trypsin moiety is depicted as TRYP.

Scheme 9

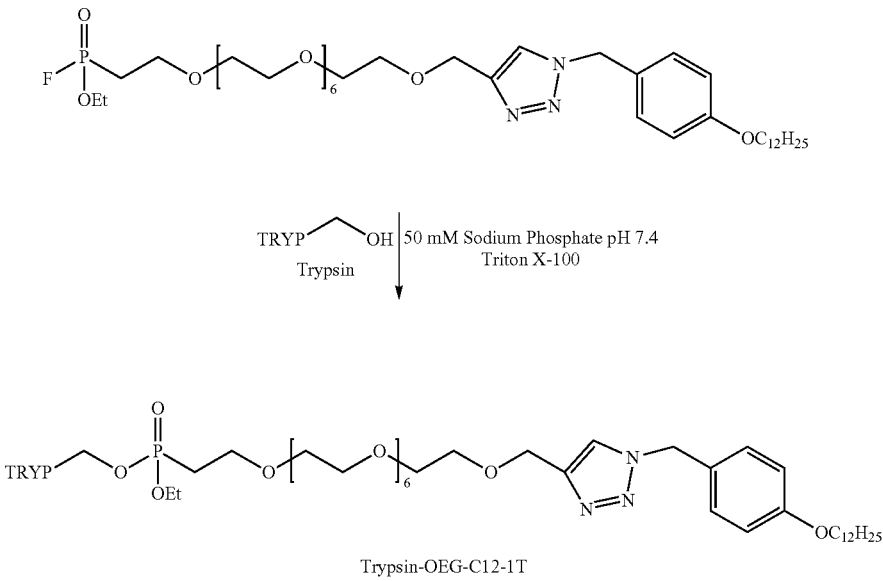

ii. Synthesis of Trypsin-OEG-C18-1T Hydrophobin Mimic 2.3 mg of trypsin was weighed in a micro centrifuge tube and mixed gently with 500 μL of 50 mM sodium phosphate pH 7.4 for 10 minutes to get 200 μM solution. 10 equivalents of AABP-OEG-C18-1T (15c) was weighed in a centrifuge tube and 20 μL of triton X-100 was added first followed by 500 μL of 50 mM sodium phosphate pH 7.4 and vertexed for 15 minutes. Now to the AABP mixture, protein solution was added and allowed to react on rotospin. The formation of corresponding hydrophobin mimic can be seen as a new peak in MALDI-TOF MS spectrum (FIG. 2.2B). The process is depicted in Scheme 10 below, where a trypsin moiety is depicted as TRYP.

Scheme 10

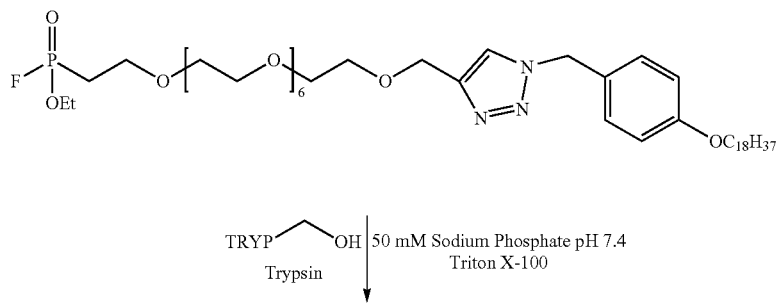

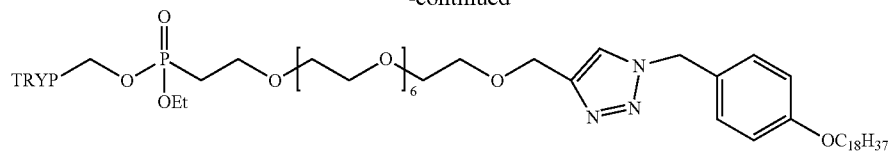

Trypsin-OEG-C18-1T iii. Synthesis of Trypsin-OEG-C6-2T Hydrophobin Mimic 2.3 mg of trypsin was weighed in a micro centrifuge tube and mixed gently with 500 μL of 50 mM sodium phosphate pH 7.4 for 10 minutes to get 200 μM solution. 10 equivalents of AABP-OEG-C6-2T (16c) was weighed in a centrifuge tube and 20 μL of triton X-100 was added first followed by 500 μL of 50 mM sodium phosphate pH 7.4 and vertexed for 15 minutes. Now to the AABP mixture, protein solution was added and allowed to react on rotospin. Monitoring the extent of modification was done by removing aliquots The formation of corresponding hydrophobin mimic can be seen as a new peak in MALDI-TOF MS spectrum (FIG. 2.2C). The process is depicted in Scheme 11 below, where a trypsin moiety is depicted as TRYP.

Scheme 11

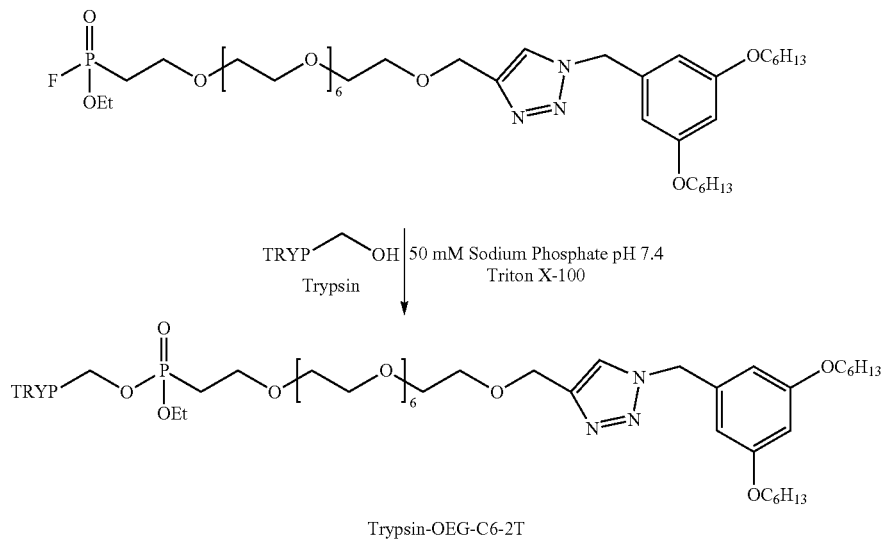

Trypsin-OEG-C6-2T iv. Synthesis of Trypsin-OEG-C12-2T Hydrophobin Mimic 2.3 mg of trypsin was weighed in a micro centrifuge tube and mixed gently with 500 μL of 50 mM sodium phosphate pH 7.4 for 10 minutes to get 200 μM solution. 10 equivalents of AABP-OEG-C12-2T (17c) was weighed in a centrifuge tube and 20 μL of triton X-100 was added first followed by 500 μL of 50 mM sodium phosphate pH 7.4. Then the mixture was vertexed for 15 minutes. Now to the AABP mixture, protein solution was added and allowed to react on rotospin. Monitoring the extent of modification was done by removing aliquots The formation of corresponding hydrophobin mimic can be seen as a new peak in MALDI-TOF MS spectrum (FIG. 2.2D). The process is depicted in Scheme 12 below, where a trypsin moiety is depicted as TRYP.

Scheme 12

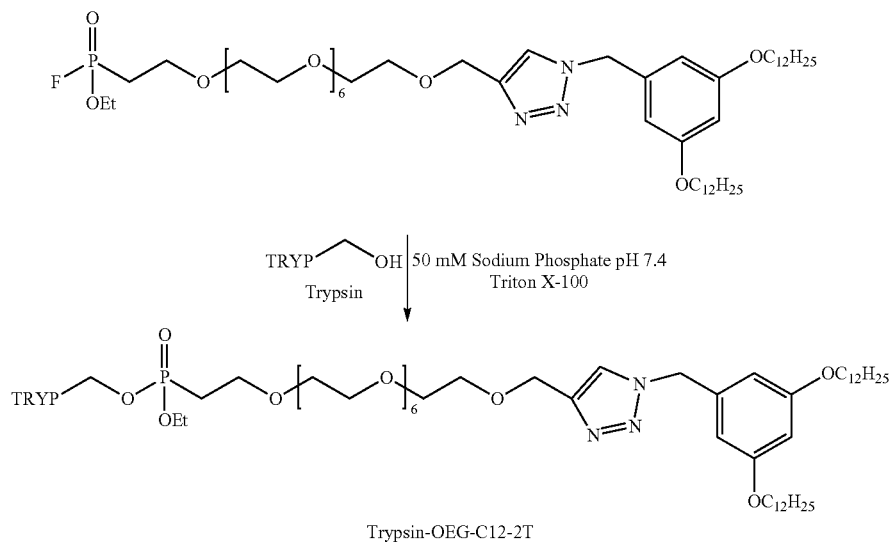

Trypsin-OEG-C12-2T v. Synthesis of Trypsin-OEG-C18-2T Hydrophobin Mimic 2.3 mg of trypsin was weighed in a micro centrifuge tube and mixed gently with 500 µL of 50 mM sodium phosphate pH 7.4 for 10 minutes to get 200 µM solution. 10 equivalents of AABP-OEG-C18-2T (1.1 mg of 18c) was weighed in a centrifuge tube and 20 µL of triton X-100 was added first followed by 500 µL of 50 mM sodium phosphate pH 7.4 and vertexed for 15 minutes. Now to the AABP mixture, protein solution was added and allowed to react on rotospin. Monitoring the extent of modification was done by removing aliquots The formation of corresponding hydrophobin mimic can be seen as a new peak in MALDI-TOF MS spectrum (FIG. 2.3C). The process is shown in Scheme 13 below, where a trypsin moiety is depicted as TRYP.

vi. Synthesis of Trypsin-OEG-C6-3T Hydrophobin Mimic 2.3 mg of trypsin was weighed in a micro centrifuge tube and mixed gently with 500 µL of 50 mM sodium phosphate pH 7.4 for 10 minutes to get 200 µM solution. 10 equivalents of AABP-OEG-C6-3T (0.9 mg of 19c) was weighed in a centrifuge tube and 20 µL of triton X-100 was added first followed by 500 µL of 50 mM sodium phosphate pH 7.4. Then the mixture was vertexed for 15 minutes. Now to the AABP mixture, protein solution was added and allowed to react on rotospin. Monitoring the extent of modification was done by removing aliquots. The formation of corresponding hydrophobin mimic can be seen as a new peak in MALDI- Scheme 13

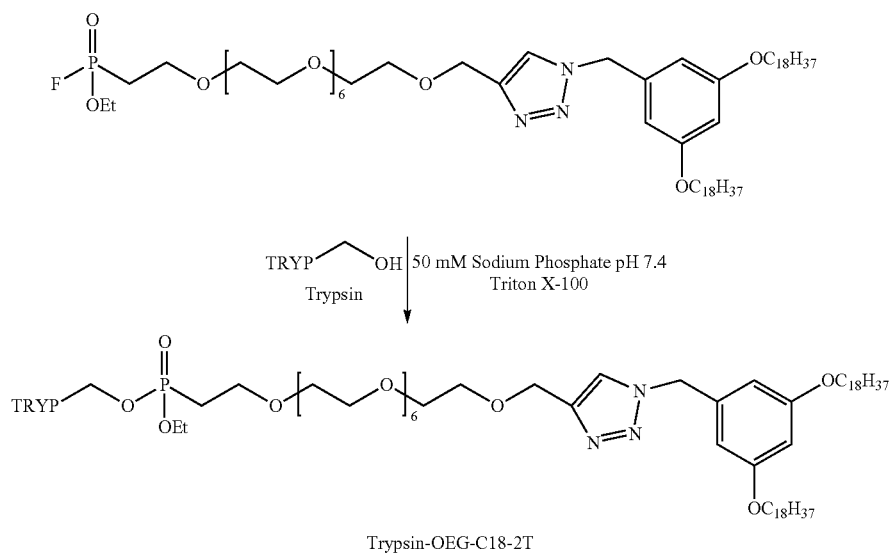

Trypsin-OEG-C18-2T

TOF MS spectrum (FIG. 2.3A). The process is shown in Scheme 14 below, where a trypsin moiety is depicted as TRYP.

clear solution obtained and then vertexed as usual. Now to the AABP mixture, protein solution was added and allowed to react on rotospin. Monitoring the extent of modification Scheme 14

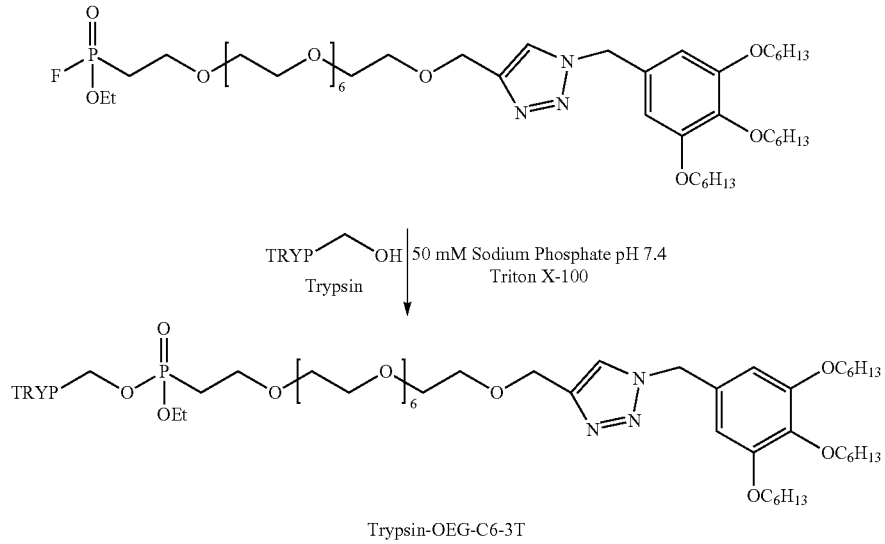

vii. Synthesis of Trypsin-OEG-C18-3T Hydrophobin Mimic

Overall procedure remained same even here for making protein solution. But for AABP-OEG-C18-3T, 10 equivalents (1.4 mg, of 21c) was weighed in a micro centrifuge tube and 20 µL of triton X-100 was added and sonicated till the mixture becomes homogenous (please note that this is the only AABP we sonicated to solubilize). 500 µL of 50 mM sodium phosphate pH 7.4 was added to this only after was done by removing aliquots the formation of corresponding hydrophobin mimic can be seen as a new peak in MALDI-TOF MS spectrum (FIG. 2.3D). The process is shown in Scheme 15 below, where a trypsin moiety is depicted as TRYP.

Scheme 15

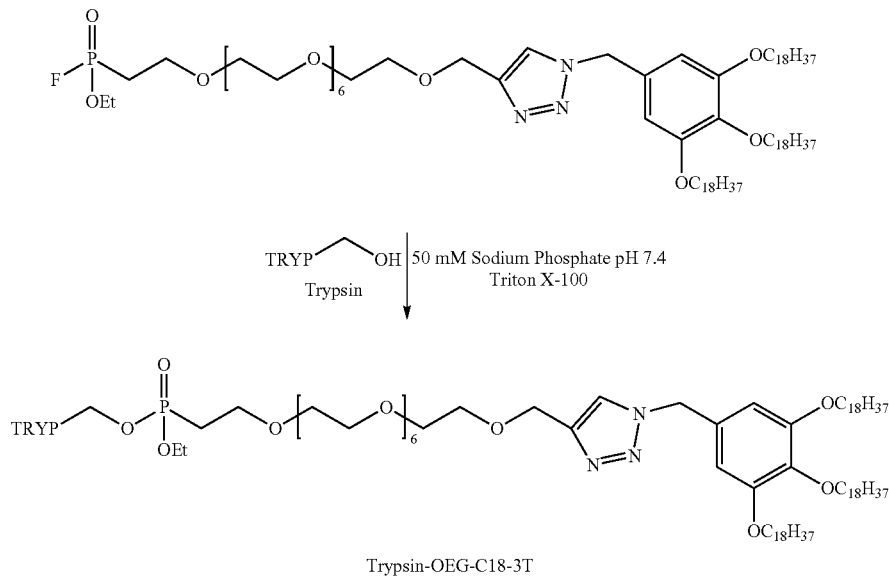

Synthesis of a trypsin-OEG-C12-3T hydrophobin mimic was achieved by a similar process, using AABP-OEG-C12-3T. The formation of a trypsin-OEG-C12-3T hydrophobin mimic was seen as a new peak in MALDI-TOF MS spectrum (FIG. 2.3B).

TABLE 2

MALDI-TOF MS data of trypsin hydrophobin mimics (varying tails).

| Mw of AABPs (Da) | Mw of native trypsin (Da) | Mw of trypsin hydrophobin mimics calculated (Da) | Mw of trypsin hydrophobin mimics obtained[#] (Da) |
|---|---|---|---|
| AABP-OEG-C12-1T (819.99) | 23,272 | 24091 | 24101 ± 22.20 |
| AABP-OEG-C18-1T (904.15) | 23,272 | 24176 | 24187 ± 19.15 |
| AABP-OEG-C6-2T (835.99) | 23,272 | 24,107 | 24,146 ± 20.43 |
| AABP-OEG-C12-2T (1,004.31) | 23,272 | 24,276 | 24,280 ± 15.28 |
| AABP-OEG-C18-2T (1,172.64) | 23,272 | 24,444 | 24,456 ± 12.61 |
| AABP-OEG-C6-3T (936.15) | 23,272 | 24,208 | 24,219 ± 18.96 |
| AABP-OEG-C12-3T (1,188.64) | 23,272 | 24,460 | 24,453 ± 13.19 |
| AABP-OEG-C18-3T (1441.12) | 23,272 | 24,713 | 24,698 ± 11.13 |

[#]Average of >10 individual recording

Example 15: Synthesis of Trypsin-C12-3T Hydrophobin Mimics (Varying Spacers)

i. Synthesis of Trypsin-DEG-C12-3T Hydrophobin Mimic 2.3 mg of trypsin was weighed in a micro centrifuge tube and mixed gently with 500 µL of 50 mM sodium phosphate pH 7.4 for 10 minutes to get 200 µM solution. 10 equivalents of AABP-DEG-C12-3T (1 mg, 22c) was weighed in a centrifuge tube and 20 µL of triton X-100 was added first followed by 500 µL of 50 mM sodium phosphate pH 7.4. This mixture was then vortexed for 15 minutes. To the AABP mixture, protein solution was added to get 100 µM protein solution and allowed to react on rotospin. Monitoring the extent of modification was done by removing aliquots. This AABP did not react up to 40 equivalents. The process is shown in Scheme 16 below, where a trypsin moiety is depicted as TRYP.

Scheme 16

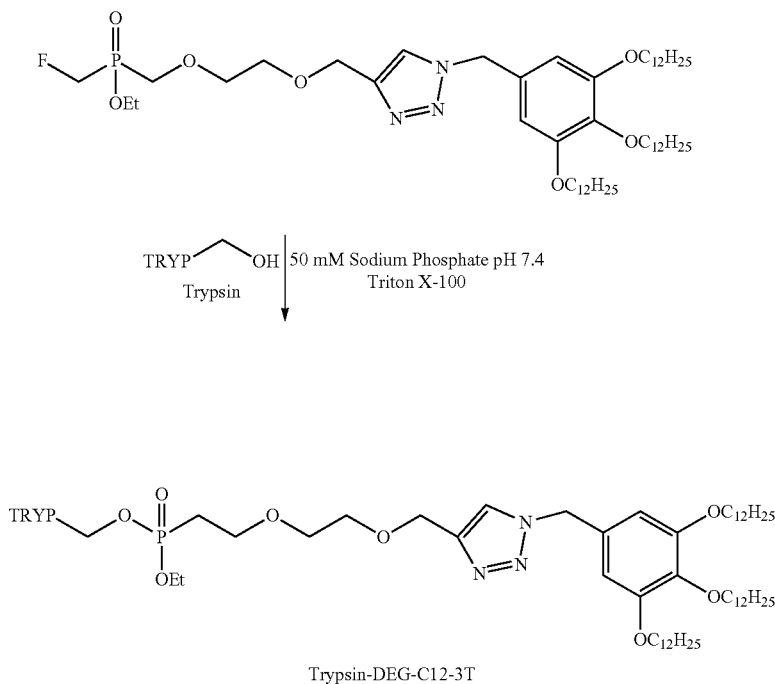

Trypsin-DEG-C12-3T ii. Synthesis of Trypsin-TEG-C12-3T Hydrophobin Mimic 2.3 mg of trypsin was weighed in a micro centrifuge tube and mixed gently with 500 µL of 50 mM sodium phosphate pH 7.4 for 10 minutes to get 200 µM solution. 10 equivalents of AABP-TEG-C12-3T (1 mg of 23c) was weighed in a centrifuge tube and 20 µL of triton X-100 was added first followed by 500 µL of 50 mM sodium phosphate pH 7.4. This mixture was then vertexed for 15 minutes. Now to the AABP mixture, protein solution was added to get 100 µM protein solution and allowed to react on rotospin. Monitoring the extent of modification was done by removing aliquots. The formation of corresponding hydrophobin mimic can be seen as a new peak in MALDI-TOF MS spectrum (FIG. 2.1A). The process is shown in Scheme 17 below, where a trypsin moiety is depicted as TRYP.

Scheme 17

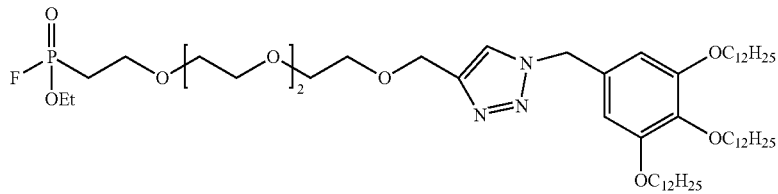

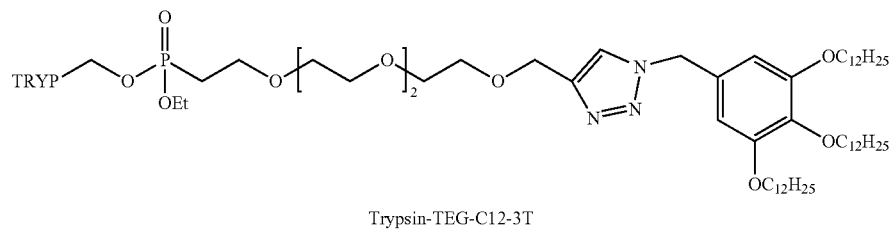

Trypsin-TEG-C12-3T iii. Synthesis of Trypsin-DDEG-C12-3T Hydrophobin Mimic 2.3 mg of trypsin was weighed in a micro centrifuge tube and mixed gently with 500 μL of 50 mM sodium phosphate pH 7.4 for 10 minutes to get 200 μM solution. 10 equivalents of AABP-DDEG-C12-3T (1.3 mg of 24c) was weighed in a centrifuge tube and 20 μL of triton X-100 was added first followed by 500 μL of 50 mM sodium phosphate pH 7.4. This mixture was then vertexed for 15 minutes. Now to the AABP mixture, protein solution was added to get 100 μM protein solution and allowed to react on rotospin. Monitoring the extent of modification was done by removing aliquots. The formation of corresponding hydrophobin mimic can be seen as a new peak in MALDI-TOF MS spectrum (FIG. 2.1C). The process is shown in Scheme 18 below, where a trypsin moiety is depicted as TRYP.

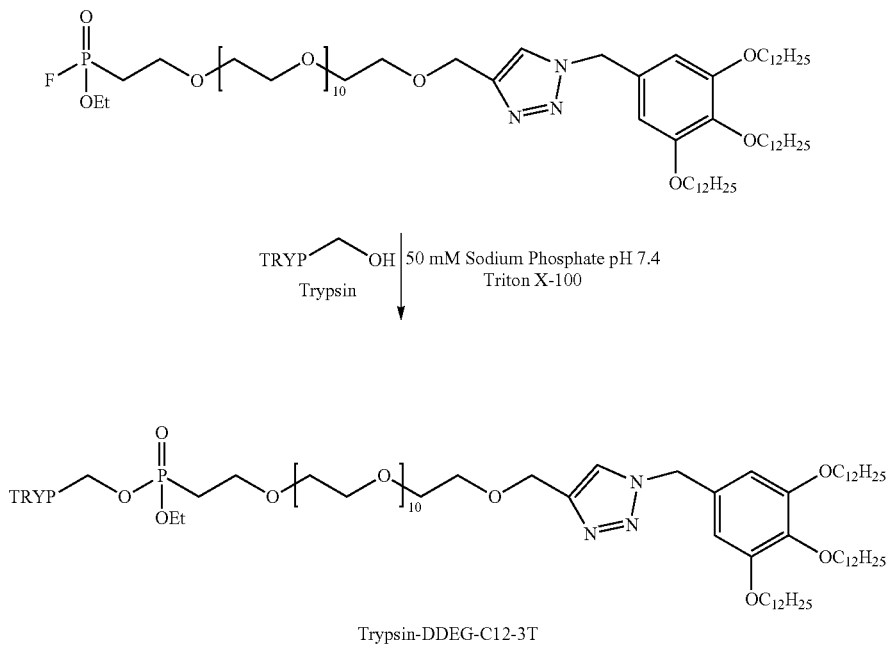

Figure 3A:
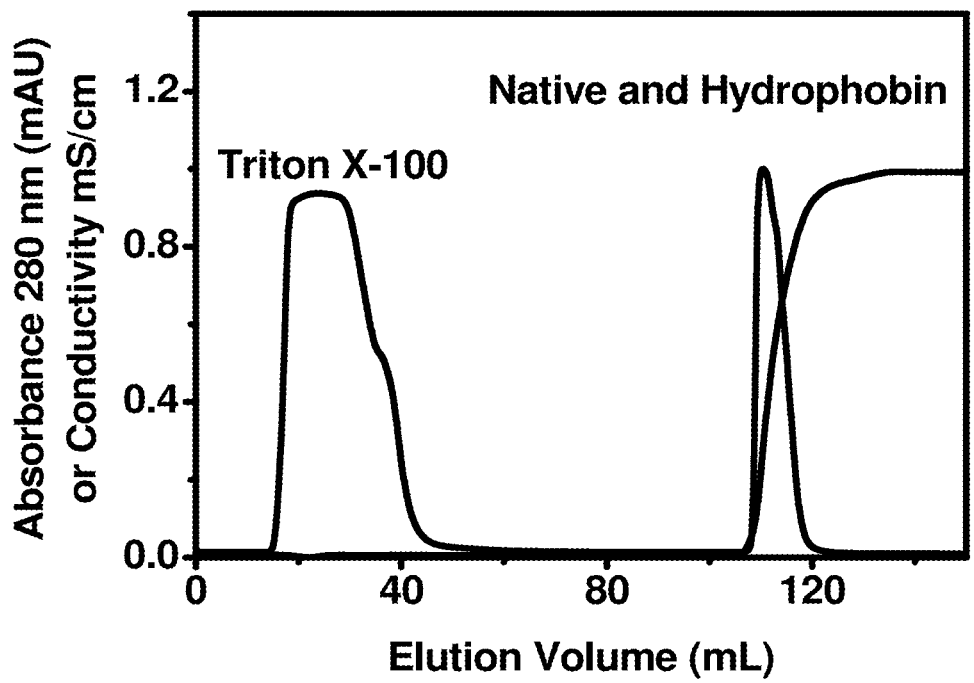
FIGS. 3A, 3B, and 3C depict purification of hydrophobin mimics FIGS. 4.1A to 4.1D and 4.2A to 4.2F depict MALDI-TOF spectra of purified trypsin hydrophobin mimics

Trypsin-DDEG-C12-3T iv. Synthesis of Trypsin-CEG(Cetyl Ethylene Glycol)-C12-3T Hydrophobin Mimic 2.3 mg of trypsin was weighed in a micro centrifuge tube and mixed gently with 500 µL of 50 mM sodium phosphate pH 7.4 for 10 minutes to get 200 µM solution. 10 equivalents of AABP-CEG-C12-3T (1.5 mg, 25c) was weighed in a centrifuge tube and 20 µL of triton X-100 was added first followed by 500 µL of 50 mM sodium phosphate pH 7.4. This mixture was then vertexed for 15 minutes. Now to the AABP mixture, protein solution was added to get 100 µM protein solution and allowed to react on rotospin. Monitoring the extent of modification was done by removing aliquots. The formation of corresponding hydrophobin mimic can be seen as a new peak in MALDI-TOF MS spectrum (FIG. 2.1D). The process is shown in scheme 19 below, where a trypsin moiety is depicted as TRYP.

surface charges of proteins. For example, to purify the reaction mixture of trypsin or chymotrypsin, we used SP sepharose, a cation exchange resin. The FPLC was performed using either Aktaprime or Aktaprime plus or Akta Explorer or Akta Pure. The column was pre-equilibrated using same buffer (50 mM sodium phosphate pH 7.4) which was used for modification and then sample was injected followed by post injection equilibration for at least 2 Column Volumes (CVs) or until the complete removal of triton X-100 for large scale reactions. The elution of the protein and its corresponding hydrophobin mimic together as mixture was later achieved using 50 mM sodium phosphate pH 7.4, 1 M NaCl as elution buffer (FIG. 3A).

Analysis of FPLC Fractions Using MALDI-TOF MS

Monitoring the fractions was done using previously stated 2% triton X-100 addition method. These protein fractions

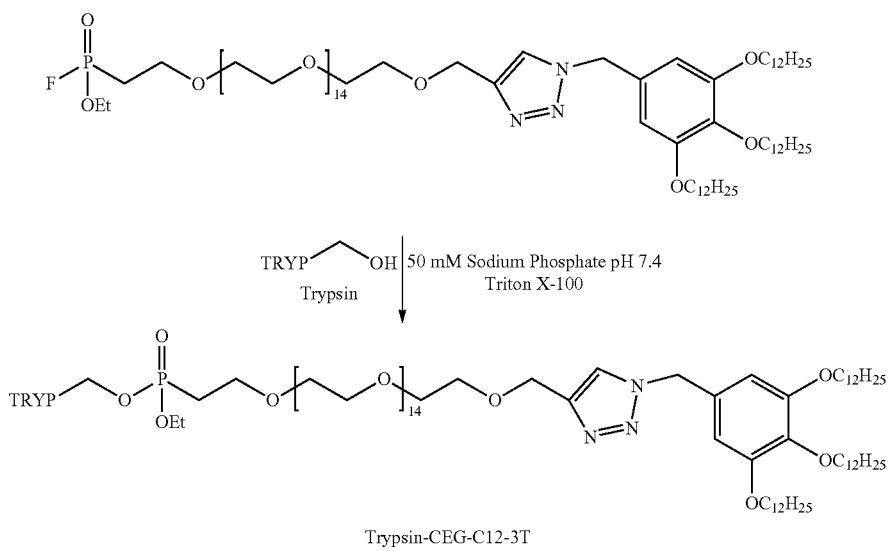

Scheme 19

TABLE 3

MALDI-TOF MS data of trypsin-C12-3T hydrophobin mimics (varying spacers).

| Mw of AABPs (Da) | Mw of native trypsin (Da) | Mw of trypsin hydrophobin mimics calculated (Da) | Mw of trypsin hydrophobin mimics obtained (Da)# |
|---|---|---|---|
| AABP-EDG-C12-3T (923) | 23,272 | 24,195 | — |
| AABP-TEG-C12-3T (1,011) | 23,272 | 24,283 | 24282 ± 14.93 |
| AABP-OEG-C12-3T (1,188) | 23,272 | 24,444 | 24,445 ± 18.96 |
| AABP-DDEG-C12-3T (1,363) | 23,272 | 24,635 | 24648 ± 20.77 |
| AABP-CEG-C12-3T (1,541) | 23,272 | 24,813 | 24824 ± 18.97 |

Average of >10 individual recording

Example 15: Purification of Hydrophobin Mimics

15.1 General Strategy

15.1.1 Ion Exchange Chromatography for Removal of Triton X-100

IEX was performed using either SP sepharose or Q sepharose resins depending on isoelectric point (PI) and showed both native and its hydrophobin mimic together as mixture in the same intensities as obtained in the reaction mixture.

15.1.2 Size Exclusion Chromatography for Removal of Native Protein

Figure 3B:
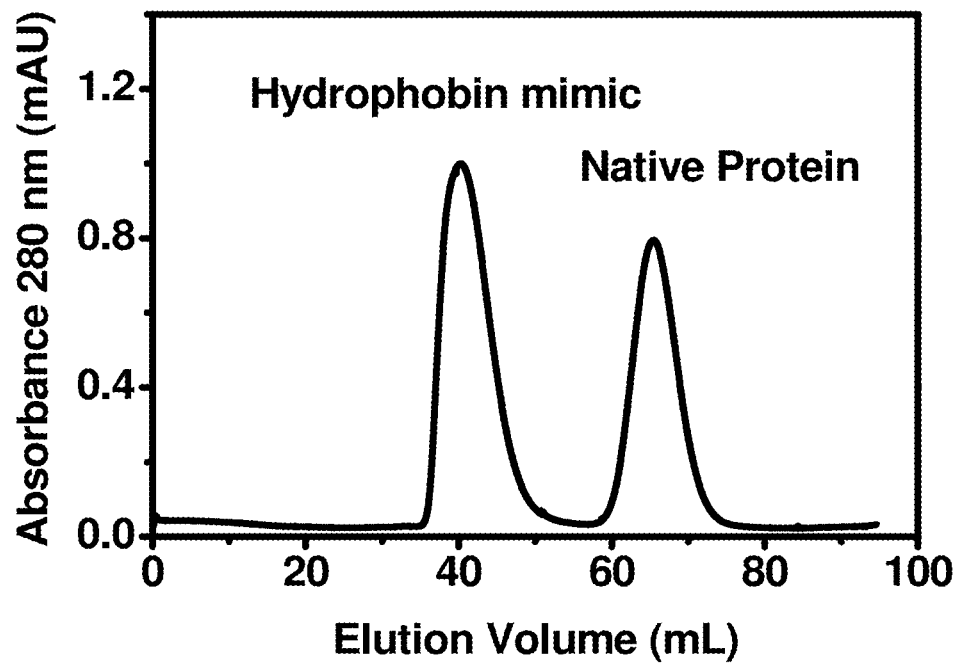

The obtained IEX fractions were lyophilized quickly and then redissolved in minimum quantity of 50 mM sodium phosphate pH 7.4, 1 M NaCl just before performing SEC. Alternately the obtained fractions were used directly for SEC immediately. The removal of native protein from the hydrophobin mimic was later achieved based on the fact that hydrophobin mimics are capable of self-assembling either alone or in high salt concentrations. For the separation of native trypsin from trypsin-OEG-C12-3Thydrophobin mimic, 50 mM sodium phosphate pH 7.4, 1 M NaCl was used as solvent. Sephacryl-100 HR 16/60 was used to separate the hydrophobin mimic from native proteins. The SEC column was equilibrated with 50 mM sodium phosphate pH 7.4, 1 M NaCl followed by injection of the sample which was free of triton X-100 and then eluted using same 50 mM sodium phosphate pH 7.4, 1 M NaCl resulting in separation of hydrophobin mimic (eluted first) from unreacted native (eluted later) (FIG. 3B).

Analysis of FPLC Fractions Using Monitoring in MALDI-TOF MS

By using the previously stated 2% triton X-100 addition method of MALDI-TOF MS analysis, the obtained fractions were monitored. The first peak was of the hydrophobin mimic and the second one was the native protein.

15.1.3 Desalting

Figure 3C:
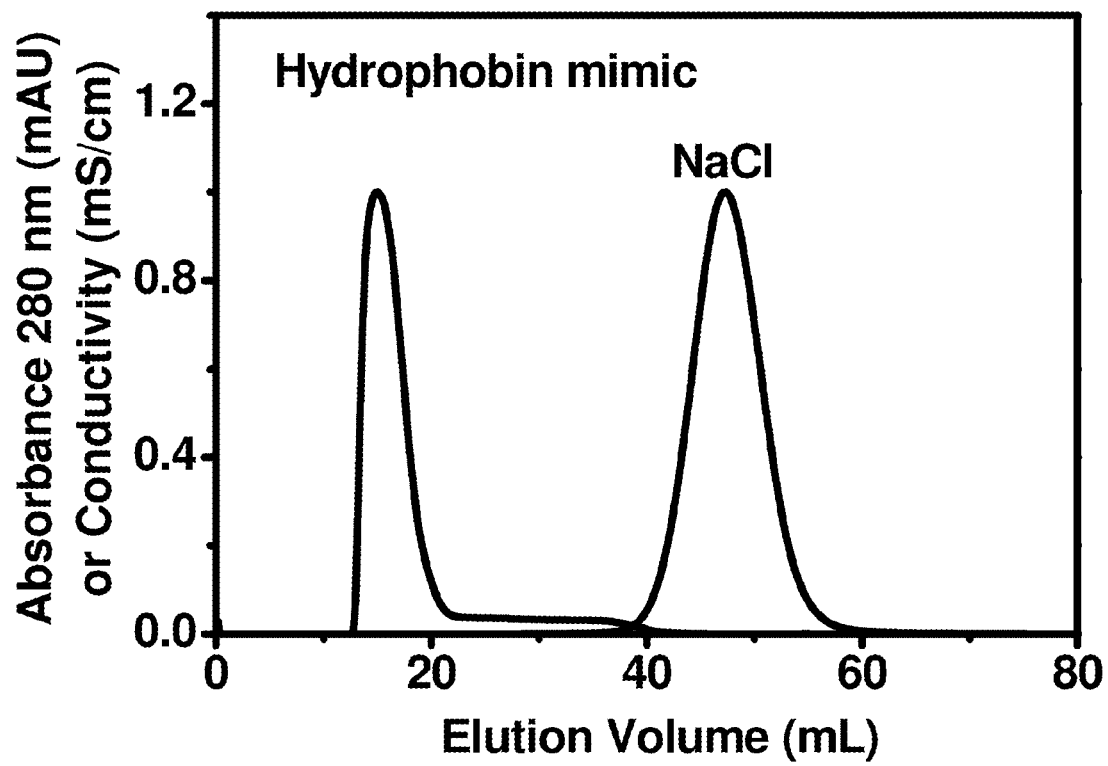

In order to perform the self assembling studies of hydrophobin mimics, it is essential that the hydrophobin mimics are free of salt, as the unknown ionic strength affects such study. The salt content from the hydrophobin mimic was removed by using Sephadex-G25 desalting column (FIG. 3C). The desalted fractions were quickly lyophilized and later dissolved in buffer when needed. The complete purification protocol is shown in the FIGS. 3A-3C.

The MALDI-TOF MS spectra of purified trypsin hydrophobin mimics are shown as follows:
Trypsin-TEG-C12-3T: FIG. 4.1A;
Trypsin-OEG-C12-3T: FIG. 4.1B;
Trypsin-DDEG-C12-3T: FIG. 4.1C;
Trypsin-CEG-C12-3T: FIG. 4.1D;
Trypsin-OEG-C12-1T: FIG. 4.2A;
Trypsin-OEG-C18-1T: FIG. 4.2B;
Trypsin-OEG-C12-2T: FIG. 4.2C;
Trypsin-OEG-C18-2T: FIG. 4.2D;
Trypsin-OEG-C6-2T: FIG. 4.2E; and
Trypsin-OEG-C12-3T: FIG. 4.2F.

Example 16: SEC Based Size Characterization of Trypsin-Hydrophobin Mimics 16.1 SEC Runs for Standard Proteins To characterize the size of soluble protein assemblies of our hydrophobin mimics, we performed size exclusion chromatography in Superdex-200 10/300 GL (GE healthcare). For this purpose, we chose standard proteins (GE Healthcare) i.e. thyroglobulin (660 kDa), ferritin (440 kDa), aldolase (158 kDa), conalbumin (75 kDa), ovalbumin (44 kDa), carbonic anhydrase (29 kDa), trypsin (23 kDa) and blue dextran (2000 kDa, to determine the void volume) in this column. A series of size exclusion runs were performed for these proteins in 50 mM sodium phosphate pH 7.4, 1 M NaCl with 0.25 mL/min as the flow rate. All the proteins were dissolved individually in milli Q water at 3 mg/mL concentration and 0.5 mL was injected. To estimate the molecular weights of the protein assemblies of hydrophobin mimics, the partition coefficients ($K_{av}$) for standard proteins were calculated. Calibration curve was plotted for $K_{av}$ of standards against relative molecular weights ($M_r$) of standard proteins.

16.2 Size Determination of Trypsin-C12-3T Hydrophobin Mimics

To determine sizes of the soluble protein assemblies of the trypsin hydrophobin mimics, SEC runs were performed in Superdex-200 10/300 GL under the same conditions with the same flow rate as standard protein runs. The elution volumes are really spectacular and we found the size of these particles is just around the size of ferritin. All the hydrophobin mimics (purified and lyophilized) were dissolved individually in milli Q water at 3 mg/mL concentration and 0.5 mL was injected. The obtained elution volumes and chromatograms are shown below. The relative molecular weights were obtained from calibration curve.

Figure 7:
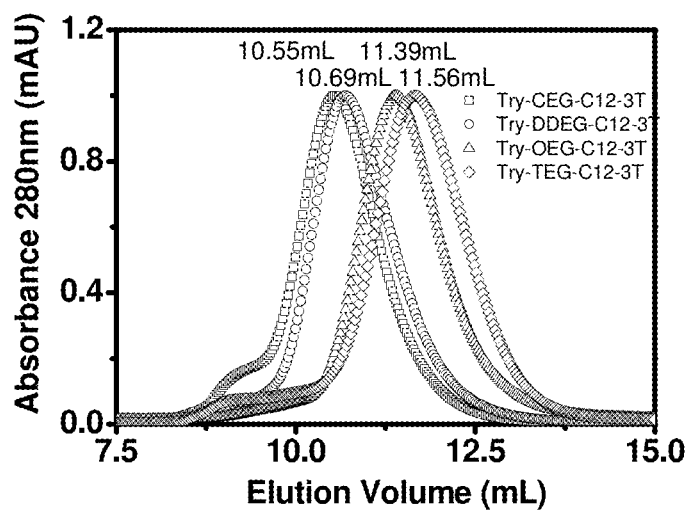
FIG. 7 depicts Size exclusion chromatograms of spacer variant trypsin hydrophobin mimics
Figure 8:
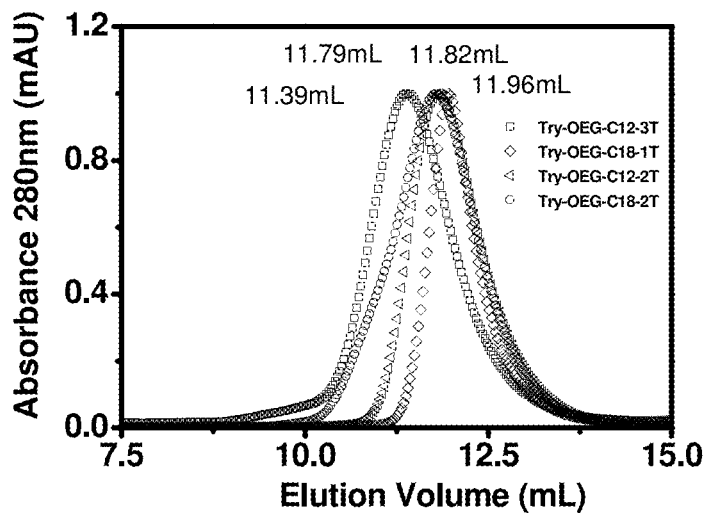
FIG. 8 depicts Size exclusion chromatograms of tail variant trypsin hydrophobin mimics.

FIG. 7 shows size exclusion chromatography of trypsin-C12-3T spacer variant hydrophobin mimics. FIG. 8 shows size exclusion chromatography of selected trypsin-OEG tail variant hydrophobin mimics.

TABLE 4

Summary of elution volumes and relative molecular weights of hydrophobin mimics.

| S.no | Hydrophobin Mimic | Elution Volume | Partition Coefficients ($K_{av}$) | Relative Mol. Wt ($M_r$) |
|---|---|---|---|---|
| 1 | Try-CEG-C12-3T | 10.55 mL | 0.136 | 400 KDa |
| 2 | Try-DDEG-C12-3T | 10.69 mL | 0.146 | 375 KDa |
| 3 | Try-OEG-C12-3T | 11.39 mL | 0.192 | 275 KDa |
| 4 | Try-TEG-C12-3T | 11.56 mL | 0.204 | 250 KDa |
| 5 | Try-OEG-C12-2T | 11.82 mL | 0.221 | 225 KDa |
| 6 | Try-OEG-C12-8T | 11.80 mL | 0.221 | 225 KDa |
| 7 | Try-OEG-C18-1T | 11.96 mL | 0.230 | 210 KDa |
| 8 | Try-OEG-C6-3T | 17.30 mL | 0.586 | ~23 KDa |
| 9 | Try-OEG-C12-1T | 18.90 mL | 0.693 | ~23 KDa |

Note.
The C12-1T, C6-3T hydrophobin mimics did not form higher aggregate in 1M NaCl, eluted at volumes corresponding to the native protein or lesser molecular weight.

Example 17: Biophysical Studies 17.1 Dynamic Light Scattering Studies

Figure 5:
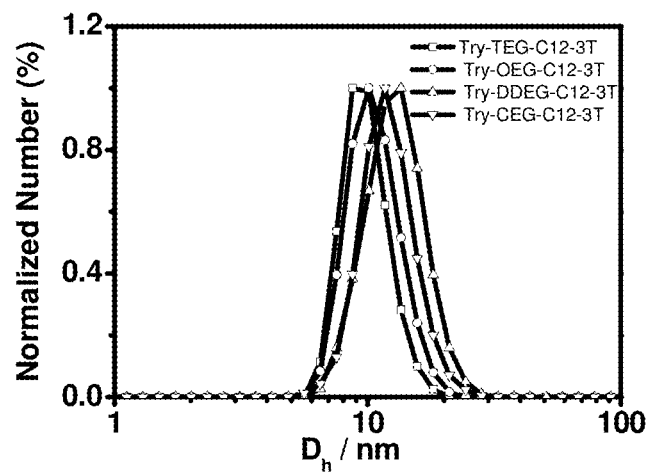
FIG. 5 depicts DLS measurements of trypsin-C12-3T spacer variant hydrophobin mimics.
Figure 6:
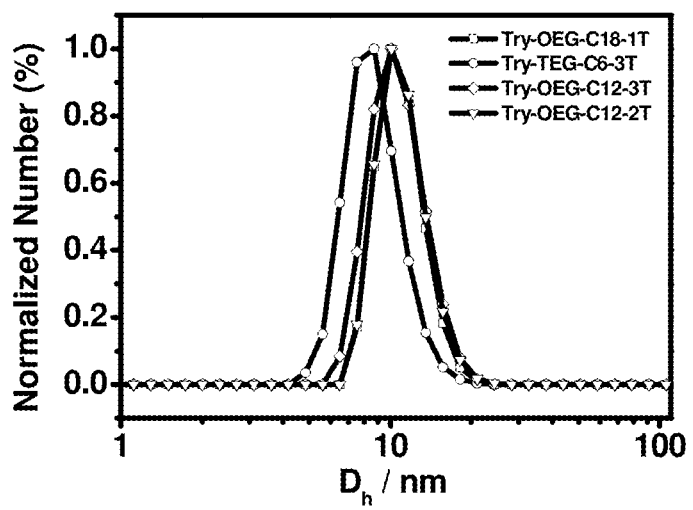
FIG. 6 depicts DLS measurements of trypsin-OEG tail variant hydrophobin mimics.

Analysis of trypsin-C12-3T spacer variant hydrophobin mimic particles and trypsin-OEG tail variant hydrophobin mimic particles was done in solution state using Dynamic Light Scattering (DLS) using Zetasizer Nano2590 (Malvern, UK). Protein samples (2 mg/mL) were prepared in 50 mM sodium phosphate pH 7.4. 1 mL of sample was taken in disposable polystyrene cells and then the mean particle size of the particles was measured at 90° scattering angle. Diameters of trypsin-C12-3T spacer variant hydrophobin mimic particles obtained as per DLS are shown in FIG. 5. Measurements reported in FIG. 5 were obtained on trypsin-TEG-C12-3T, trypsin-OEG-C12-3T, trypsin-DDEG-C12-3T, and trypsin-CEG-C12-3T. Diameters of trypsin-OEG tail variant hydrophobin mimic particles obtained as per DLS are shown in FIG. 6. Measurements reported in FIG. 6 were recorded on trypsin-OEG-C18-1T, trypsin-TEG-C6-3T, trypsin-OEG-C12-3T, and trypsin-OEG-C12-2T.

17.2 Fluorescence Spectroscopy

Figure 9:
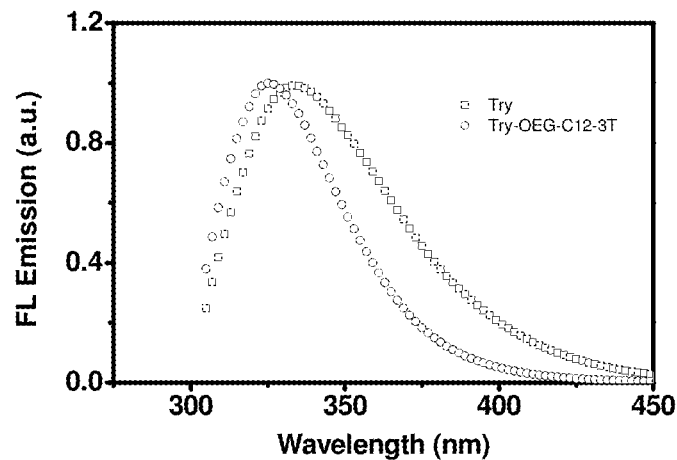
FIG. 9 depicts Fluorescence measurements of native trypsin and trypsin-OEG-C12-3T hydrophobin mimic.

The fluorescence measurements of native protein and hydrophobin mimic was carried using Xenon arc lamp on Fluorolog spectrofluorimeter (HORIBA, Jobin-Yvon). Protein samples (1 mg/mL) were prepared in 50 mM sodium phosphate pH 7.4. Measurements were carried out at tryptophan specific excitation wavelength of 295 nm in a 10 mm path length cuvette (FIG. 9). Fluorescence studies revealed tryptophan emission was blue shifted about 10 nm with respect to wild type trypsin.

17.3 Circular Dichroism (CD) Spectroscopy

Figure 10:
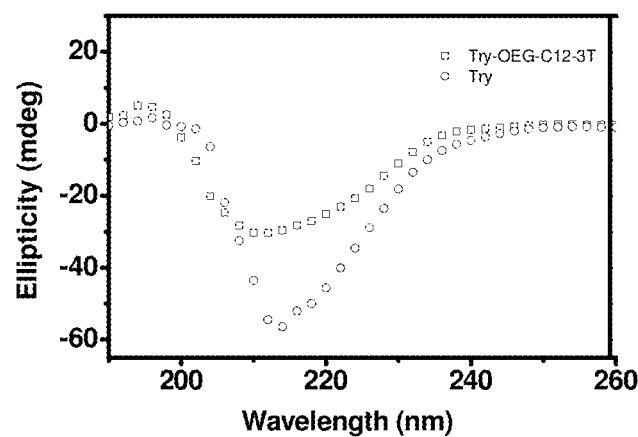
FIG. 10 depicts CD measurements of native trypsin and trypsin-OEG-C12-3T hydrophobin mimic

The CD spectra of native trypsin and trypsin-OEG-C12-3T hydrophobin mimic were recorded on Jasco J-815 spectrometer. Protein samples (1 mg/mL) were prepared in 50 mM sodium phosphate pH 7.4 and measurements were performed in a 1 mm path length cuvette. The spectra were obtained at scanning speed of 50 nm/minute within range of 195-250 nm. Mean residue elasticity was converted from accumulated spectra of five measurements for each sample (FIG. 10). Similarly, CD results revealed the overall structure of Trypsin-OEG-C12-3T is slightly different compared to native trypsin.

17.4 Zeta Potential Measurement

Figure 11:
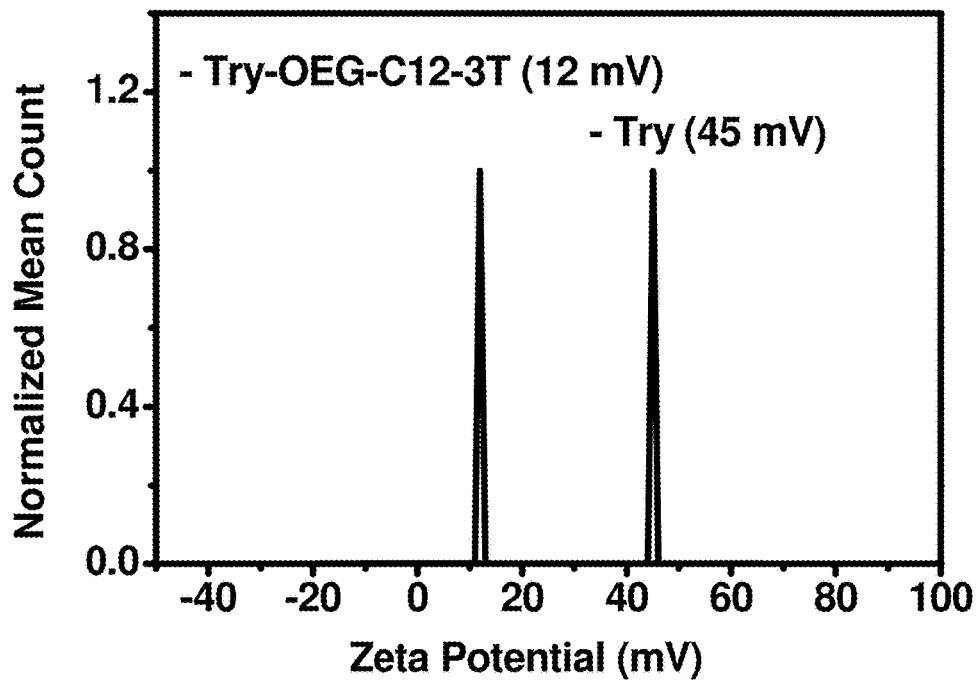
FIG. 11 depicts Zeta potential measurements of native trypsin and trypsin-OEG-C12-3T hydrophobin.

The comparison of zeta potential for native trypsin and trypsin-OEG-C12-3T hydrophobin mimic particles was done in solution state using Zetasizer Nano2590 (Malvern, UK). Protein samples (1 mg/mL) were prepared in milli-Q water. 1 mL of sample was taken in disposable cells and measured (FIG. 11). The surface charge of Trypsin-OEG-C12-3T was found to be +12 mV considerable lower than native trypsin +45 mV.

Any patents or publications mentioned in this specification are indicative of the levels of those skilled in the art to which the invention pertains. Further, these patents and publications are incorporated by reference herein to the same extent as if each individual publication was specifically and individually incorporated by reference. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

We claim:

1. A hydrophobin mimic of Formula I for use in bio-nano technology:

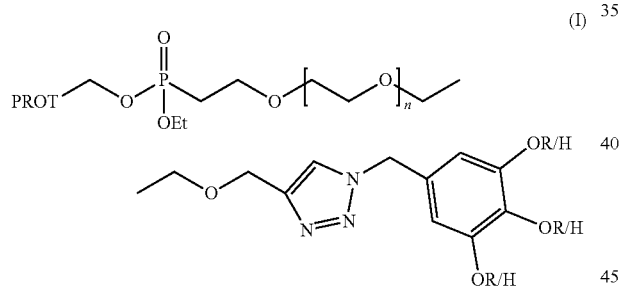

comprising;
a hydrophilic protein head group PROT having a length of up to 500 amino acids, selected from the group consisting of serine proteases, cysteine proteases, aspartic proteases, metalloproteases, trypsin, chymotrypsin, subtilisin, proteinase K, and mixtures thereof;
a hydrophilic spacer comprising a phosphonate ester of an ethylene glycol oligomer, wherein 'n' is an integer 1-30; and
a hydrophobic tail of formula II,

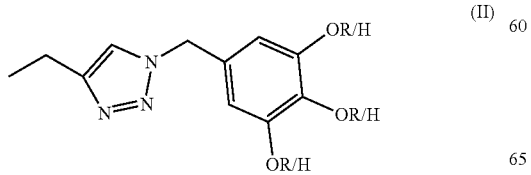

wherein "R/H" represents either H or a $C_4$-$C_{20}$ (un)substituted or substituted straight, branched, cyclic, or acyclic aliphatic moiety; an aromatic moiety; or an alkylphenyl moiety, wherein at least one R/H is not H.

2. A hydrophobin mimic, selected from the group consisting of;
   i. a conjugate of serine protease and ethyl (1-(1-(3,4,5-tris(dodecyloxy)benzyl)-1H-1,2,3-triazol-4-yl)-2,5,8,11,14,17,20,23-octaoxapentacosan-25-yl) phosphono fluoridate (serine protease-C12-3T);
   ii. a conjugate of trypsin and ethyl (1-(1-(4-(dodecyloxy)benzyl)-1H-1,2,3-triazol-4-yl)-2,5,8,11,14,17,20,23-octaoxapentacosan-25-yl)phosphonofluoridate (trypsin-OEG-C12-1T);
   iii. a conjugate of trypsin and ethyl (1-(1-(4-(octadecyloxy)benzyl)-1H-1,2,3-triazol-4-yl)-2,5,8,11,14,17,20,23-octaoxapentacosan-25-yl)phosphonofluoridate (trypsin-OEG-C18-1T);
   iv. a conjugate of trypsin and ethyl (1-(1-(3,5-bis(hexyloxy)benzyl)-1H-1,2,3-triazol-4-yl)-2,5,8,11,14,17,20,23-octaoxapentacosan-25-yl) phosphono fluoridate (Trypsin-OEG-C6-2T);
   v. a conjugate of trypsin and ethyl (1-(1-(3,5-bis(dodecyloxy)benzyl)-1H-1,2,3-triazol-4-yl)-2,5,8,11,14,17,20,23-octaoxapentacosan-25-yl)phosphonofluoridate (trypsin-OEG-C12-2T);
   vi. a conjugate of trypsin and ethyl (1-(1-(3,5-bis(octadecyloxy)benzyl)-1H-1,2,3-triazol-4-yl)-2,5,8,11,14,17,20,23-octaoxapentacosan-25-yl) phosphonofluoridate (trypsin-OEG-C18-2T);
   vii. a conjugate of trypsin and ethyl (1-(1-(3,4,5-tris(hexyloxy)benzyl)-1H-1,2,3-triazol-4-yl)-2,5,8,11,14,17,20,23-octaoxapentacosan-25-yl)phosphonofluoridate(trypsin-OEG-C6-3T);
   viii. a conjugate of trypsin and ethyl (1-(1-(3,4,5-tris(dodecyloxy)benzyl)-1H-1,2,3-triazol-4-yl)-2,5,8,11,14,17,20,23-octaoxapentacosan-25-yl)phosphonofluoridate(trypsin-OEG-C12-3T);
   ix. a conjugate of trypsin and ethyl (1-(1-(3,4,5-tris(octadecyloxy)benzyl)-1H-1,2,3-triazol-4-yl)-2,5,8,11,14,17,20,23-octaoxapentacosan-25-yl)phosphonofluoridate(trypsin-OEG-C18-3T);
   x. a conjugate of trypsin and Ethyl (2-(2-((1-(3,4,5-tris(dodecyloxy)benzyl)-1H-1,2,3-triazol-4-yl)methoxy)ethoxy)ethyl)phosphonofluoridate (trypsin-DEG-C12-3T);
   xi. a conjugate of trypsin and ethyl (1-(1-(3,4,5-tris(dodecyloxy)benzyl)-1H-1,2,3-triazol-4-yl)-2,5,8,11-tetraoxatridecan-13-yl) phosphonofluoridate (trypsin-TEG-C12-3T);
   xii. a conjugate of trypsin and ethyl (1-(1-(3,4,5-tris(dodecyloxy)benzyl)-1H-1,2,3-triazol-4-yl) 2,5,8,11,14,17,20,23,26,29,32,35-dodecaoxaheptatriacontan-37-yl)phosphonofluoridate (trypsin-DDEG-C12-3T);
   xiii. a conjugate of trypsin and ethyl (1-(1-(3,4,5-tris(dodecyloxy)benzyl)-1H-1,2,3-triazol-4-yl)-2,5,8,11,14,17,20,23,26,29,32,35,38,41,44,47-hexadecaoxanonatetracontan-49-yl)phosphonofluoridate(trypsin-CEG-C12-3T); and
   xiv. mixtures thereof.

3. A self-assembled protein nanocontainer, prepared from the hydrophobin mimic according to claim 1.

4. The hydrophobin mimic according to claim 1, wherein the hydrophobin mimic has a particle size in range of 1-10 nm.

5. The self-assembled protein nanocontainer according to claim 3, wherein the size of the protein nanocontainer is in the range of 8-100 nm.

6. A process for synthesis of a pure hydrophobin mimic of formula (I) according to claim 1, comprising;
   i. Self-assembling the hydrophobin mimic of formula (I) obtained by coupling the pre-weighed protein with the amphiphilic activity based probes (AABPs), homogenized in triton-X-100 at pH in the range 7.0-7.5, either alone or in high salt concentrations;
   ii. Removing triton X-100 from the protein mixture using Ion exchange chromatography and eluting the native and hydrophobin mimic using eluting buffer solution;
   iii. Removing the native protein from the hydrophobin mimic in high salt concentrations using size exclusion chromatography followed by desalting or dialyzing to obtain pure hydrophobin mimic.

7. The process according to claim 6, wherein the synthesis of amphiphilic activity based probes (AABPs) comprises reacting a phosphonate ester of an ethylene glycol oligomer with 1T or 2T or 3T hydrophobic azides using click chemistry followed by deprotection using oxalyl chloride to obtain mono phosphonate ester intermediate; which is treated with diethyl amino sulfur trifluoride (DAST) to obtain amphiphilic activity based probes (AABPs).

8. The process according to claim 7, wherein the synthesis of 1T or 2T or 3T hydrophobic azide comprises;
   i. Refluxing mixture of 4-hydroxybenzyl alcohol (in the case of 1T) or di/tri hydroxy ester with alkyl bromide (in the case of 2T or 3T), base and potassium iodide in a solvent to obtain mono or di or tri-O-alkyl protected alcohol or esters;
   ii. Reducing di or tri-O-alkyl protected esters using reducing agent in a solvent to obtain the alcohol derivative;
   iii. Halogenating the alcohol derivative to obtain the halo derivative;
   iv. Reacting the halo derivative with sodium azide in a solvent to yield 1T or 2T or 3T hydrophobic azides.

9. The process according to claim 8, wherein the solvent is selected from group consisting of polar protic solvents, polar protic solvents, and non-polar solvents.

10. A composition comprising:
    a hydrophobin mimic of formula (I) according to claim 1; and
    at least one component selected from from the group consisting of an excipient, a surfactant, an acid, a base, a buffer system, an inorganic particle, a UV absorber, and a mixture thereof.

11. The hydrophobin mimics of formula (I) according to claim 1 for use in bio-nanotechnology, in drug delivery system, in vaccine development, for diagnostic and theranostics applications, as spreading agent, surfactants, as tags to purify proteins from complex mixtures and as biosensors, to provide antibody drug conjugate or as antimicrobial agents.

12. A hydrophobin mimic of Formula I for use in bio-nano technology:

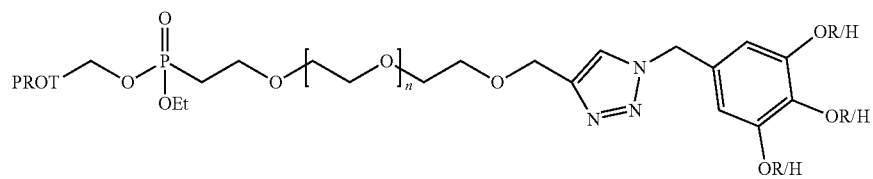

(I)

comprising;
   a hydrophilic protein head group PROT having a length of up to 500 amino acids, selected from the group consisting of serine proteases, cysteine proteases, aspartic proteases, metalloproteases, trypsin, chymotrypsin, subtilisin, proteinase K, and mixtures thereof;
   a hydrophilic spacer comprising a phosphonate ester of an ethylene glycol oligomer, wherein 'n' is an integer 1-30; and
   a hydrophobic tail of formula II,

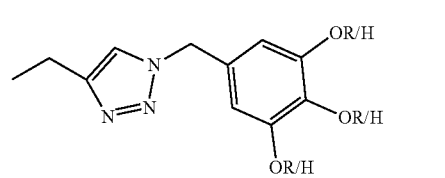

(II)

wherein "OR/H" represents either:
   H; or
   an alkoxy group having a C4-C30 (un)substituted or substituted straight, branched, cyclic or acyclic aliphatic, aromatic or alkyl phenyl moiety, wherein at least one OR/H is not H.

13. The hydrophobin mimic according to claim 12, wherein the hydrophobin mimic has a particle size in range of 1-10 nm.

* * * * *